US007846949B2

(12) United States Patent
Molteni et al.

(10) Patent No.: US 7,846,949 B2
(45) Date of Patent: Dec. 7, 2010

(54) COMPOUNDS AND COMPOSITIONS AS LXR MODULATORS

(75) Inventors: Valentina Molteni, San Diego, CA (US); Xiaolin Li, Del Mar, CA (US); Fang Liang, Carlsbad, CA (US); Juliet Nabakka, Santee, CA (US); Enrique Saez, San Diego, CA (US); John Wityak, Carlsbad, CA (US)

(73) Assignee: IRM LLC, Hamilton (BM)

( * ) Notice: Subject to any disclaimer, the term of this patent is extended or adjusted under 35 U.S.C. 154(b) by 853 days.

(21) Appl. No.: 10/589,410

(22) PCT Filed: Feb. 11, 2005

(86) PCT No.: PCT/US2005/004652

§ 371 (c)(1), (2), (4) Date: Jun. 4, 2007

(87) PCT Pub. No.: WO2005/077122

PCT Pub. Date: Aug. 25, 2005

(65) Prior Publication Data

US 2007/0293547 A1  Dec. 20, 2007

Related U.S. Application Data

(60) Provisional application No. 60/544,149, filed on Feb. 11, 2004.

(51) Int. Cl.
*A61K 31/44* (2006.01)
*A61K 31/42* (2006.01)
*A61K 31/41* (2006.01)
*C07D 213/55* (2006.01)
*C07D 498/00* (2006.01)
*C07D 231/12* (2006.01)
*C07C 229/00* (2006.01)

(52) U.S. Cl. ................... 514/357; 514/378; 514/406; 514/359; 546/335; 548/242; 548/373.1; 560/41

(58) Field of Classification Search ............... None
See application file for complete search history.

(56) References Cited

U.S. PATENT DOCUMENTS 5,110,348 A   5/1992  Hopwood

FOREIGN PATENT DOCUMENTS

| CH | 516523 | * | 11/1969 |
|---|---|---|---|
| CH | 516523 | A | 12/1971 |
| DE | 1185194 | | 1/1965 |
| EP | 1340750 | A1 | 9/2003 |
| GB | 1236091 | A | 6/1971 |
| JP | 56083458 | A | 7/1981 |
| JP | 07258224 | A | 10/1995 |
| JP | 11001456 | A | 1/1999 |

OTHER PUBLICATIONS

Greene, Protective Groups in Organic Chemistry, 1981, John Wiley & Sons, Inc., pp. 158-169.*
Evans et al., "Some substituted phenylalkanoic acids and N-substituted malonailic, succinanillic, and anilinoalkanoic acids as potential antiinflammatory agents.", Journal of Medicinal Chemistry, vol. 12, No. 6, pp. 1006-1010, 1969.
Larizza A., "N-aryl-N-aroylamino acid derivatives.", Journal of Medicinal Chemistry, vol. 13, No. 5, pp. 1019-1020, 1970.
Cao et al., "Antidiabetic Action of a Liver X Receptor Agonist Mediated by Inhibition of Hepatic Gluconeogenesis", Journal of Biological Chemistry, vol. 278, pp. 1131-1136, 2003.
Cao et al., "Liver X Receptors as Potential Therapeutic Targets for Multiple Diseases", Drug News Perspect., vol. 17, pp. 35-41, 2004.
Chin et al., "Miniaturization of Cell-Based b-Lactamase-Dependent FRET Assays to Ultra-High Throughput Formats to Identify Agonists of Human Liver X Receptors", Assay and Drug Development Technologies, vol. 1, pp. 777-787, 2003.
Collins et al., "Identification of a Nonsteroidal Liver X Receptor Agonist through Parallel Array Synthesis of Tertiary Amines", Journal of Medicinal Chemistry, vol. 45, pp. 1963-1966, 2002.
Fowler et al., "Liver X Receptor Activators Display Anti-Inflammatory Activity in Irritant and Allergic Contact Dermatitis Models: Liver-X-Receptor-Specific Inhibition of Inflammation and Primary Cytokine Production", J Invest Dermatol., vol. 120, pp. 246-255, 2003.
Jaye, Micheal, "LXR agonists for the treatment of atherosclerosis", Current Opinion in Investigational Drugs, vol. 4, pp. 1053-1058, 2003.
Joseph et al., "Synthetic LXR ligand inhibits the development of atherosclerosis in mice", PNAS, vol. 99, pp. 7604-7609, 2002.
Josepg et al., "Reciprocal regulation of inflammation and lipid metabolism by liver X receptors", Nature Medicine, vol. 9, pp. 213-219, 2003.
Joseph et al., "LXRs: new therapeutic targets in atherosclerosis?", Current Opinion in Pharmacology, vol. 3, pp. 192-197, 2003.
Lafitte et al., "Activation of liver X receptor improves glucose tolerance through coordinate regulation of glucose metabolism in liver and adipose tissue", PNAS, vol. 100, pp. 5419-5424, 2003.
Lehmann et al., "Activation of the Nuclear Receptor LXR by Oxysterols Defines a New Hormone Response Pathway", Journal of Biological Chemistry, vol. 272, pp. 3137-3140, 1997.
Repa et al., "Regulation of mouse sterol regulatory element-binding protein-1c gene (SREBP-1c) by oxysterol receptors, LXRalpha and LXRbeta", Genes & Development, vol. 14, pp. 2819-2830, 2000.
Schultz et al., "Role of LXRs in control of lipogenesis", Genes & Development, vol. 14, pp. 2831-2838, 2000.

(Continued)

*Primary Examiner*—Paul A Zucker
(74) *Attorney, Agent, or Firm*—Daniel E. Raymond; Genomics Institute of the Novartis Research Foundation

(57) ABSTRACT

The invention provides compounds, pharmaceutical compositions comprising such compounds and methods of using such compounds to treat or prevent diseases or disorders associated with the activity of liver X receptors (LXRs).

3 Claims, No Drawings

OTHER PUBLICATIONS

Spencer et al., "Pharmacophore Analysis of the Nuclear Oxysterol Receptor LXRalpha", Journal of Medicinal Chemistry, vol. 44, pp. 886-897, 2001.

Tangiralla et al., "Identification of macrophage liver X receptors as inhibitors of atherosclerosis", PNAS, vol. 99, pp. 11896-11901, 2002.

Terasaka et al., "T-0901317, a synthetic liver X receptor ligand, inhibits development of atherosclerosis in LDL receptor-deficient mice", FEBS Letters, vol. 536, pp. 6-11, 2003.

Tontonoz et al., "Liver X Receptor Signaling Pathways in Cardiovascular Disease", Mol. Endocrinol., vol. 17, pp. 985-993, 2003.

* cited by examiner

COMPOUNDS AND COMPOSITIONS AS LXR MODULATORS

CROSS-REFERENCE TO RELATED APPLICATIONS

This application is a 371 U.S. national phase application of international application No. PCT/US2005/004652 filed on 11 Feb. 2005, which application claims priority to U.S. provisional patent application No. 60/544,149, filed on 11 Feb. 2004. The present application claims priority to and benefit of these applications, the disclosure of which is incorporated herein by reference for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of liver X receptors (LXRs).

2. Background

Liver X receptors (LXRs), LXRα and LXRβ, are nuclear receptors that regulate the metabolism of several important lipids, including cholesterol and bile acids. While LXRβ is expressed ubiquitously in the body, LXRα is expressed in the liver and to a smaller degree in the kidneys, small intestine, adipose tissue, spleen and adrenal glands.

LXRs bind to the ATP binding cassette transporter-1 (ABCA1) promoter and increase expression of the gene to produce ABCA1 protein. ABCA1 is a membrane bound transport protein that is involved in the regulation of cholesterol efflux from extra-hepatic cells onto nascent high-density lipoprotein (HDL) particles. Mutations in the ABCA1 gene result in low levels of HDL and an accompanying increased risk of cardiovascular diseases such as atherosclerosis, myocardial infarction and ischemic stroke. LXRα and β agonists have been shown to increase ABCA1 gene expression thereby increasing HDL cholesterol and, as a consequence, decreasing both the net absorption of cholesterol and the risk of cardiovascular disease. LXR agonists also upregulate macrophage expression of apolipoprotein E (apoE) and ABCG1, both of which contribute to the efflux of cellular cholesterol. By stimulating macrophage cholesterol efflux through upregulation of ABCA1, ABCG1 and/or apoE expression, as well as increasing the expression of other target genes including cholesterol ester transfer protein and lipoprotein lipase, LXR agonists influence plasma lipoproteins.

The novel compounds of this invention modulate the activity of LXRs and are, therefore, expected to be useful in the treatment of LXR-associated diseases such as cardiovascular diseases, inflammation and disorders of glucose metabolism such as insulin resistance and obesity.

SUMMARY OF THE INVENTION

In one aspect, the present invention provides compounds of Formula I:

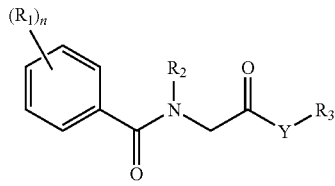

in which:

Y is selected from O, $NR_4$ and S; wherein $R_4$ is selected from hydrogen, $C_{1-6}$alkyl, $C_{1-6}$alkoxy, halo-substituted-$C_{1-6}$alkyl, halo-substituted-$C_{1-6}$alkoxy, $C_{6-10}$aryl-$C_{0-4}$alkyl, $C_{3-8}$heteroaryl-$C_{0-4}$alkyl, $C_{3-12}$cycloalkyl-$C_{0-4}$alkyl and $C_{3-8}$heterocycloalkyl-$C_{0-4}$alkyl;

n is selected from 0, 1, 2, 3 and 4;

$R_1$ is selected from halo, hydroxy, nitro, cyano, $C_{1-6}$alkyl, $C_{1-6}$alkoxy, halo-substituted-$C_{1-6}$alkyl and halo-substituted-$C_{1-6}$alkoxy, —$XC(O)R_4$, —$XOC(O)R_4$, —$XC(O)OR_4$, —$XOR_4$, —$XS(O)_2R_4$, —$XS(O)R_4$, —$XSR_4$, —$XNR_4R_8$, —$XC(O)NR_4R_8$, —$XNR_4C(O)R_4$, —$XNR_4C(O)OR_4$, —$XNR_4C(O)NP_4R_8$, —$XNR_4C(NR_4R_4)NR_4R_8$, —$XP(O)(OR_4)OR_4$, —$XOP(O)(OR_4)OR_4$, —$XS(O)_2NR_4R_8$, —$XS(O)NR_4R_8$, —$XSNR_4R_8$, —$XNR_4S(O)_2R_4$, —$XNR_4S(O)R_4$, —$XSR_4$, —$XNR_4C(O)NR_4R_8$, - and —$XC(O)SR_4$; wherein X is a bond or $C_{1-6}$alkylene; and R and $R_8$ are independently selected from hydrogen, $C_{1-6}$alkyl, $C_{1-6}$alkoxy, halo-substituted-$C_{1-6}$alkyl, halo-substituted-$C_{1-6}$alkoxy, $C_{6-10}$aryl-$C_{0-4}$alkyl, $C_{3-5}$heteroaryl-$C_{0-4}$alkyl, $C_{3-12}$cycloalkyl-$C_{0-4}$alkyl and $C_{3-8}$heterocycloalkyl-$C_{0-4}$alkyl; or $R_4$ and $R_8$ together with the nitrogen atom to which $R_4$ and $R_9$ are attached form $C_{5-10}$heteroaryl or $C_{3-8}$heterocycloalkyl; wherein any aryl, heteroaryl, cycloalkyl or heterocycloalkyl of $R_4$ or the combination of $R_4$ and $R_8$ is optionally substituted with 1 to 4 radicals independently selected from the group consisting of halo, hydroxy, cyano, nitro, $C_{1-6}$alkyl, $C_{1-6}$alkoxy, halo-substituted-$C_{1-6}$alkyl and halo-substituted-$C_{1-6}$alkoxy;

$R_2$ is selected from $C_{6-10}$aryl-$C_{0-4}$alkyl, $C_{3-8}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any aryl-alkyl, heteroaryl-alkyl, cycloallyl-alkyl or heterocycloalkyl-alkyl of $R_2$ is optionally substituted by 1 to 5 radicals independently selected from halo, cyano-$C_{0-6}$alkyl, $C_{1-6}$alkoxy, halo-substituted-$C_{1-6}$alkyl, halo-substituted-$C_{1-6}$alkoxy, —$OXR_7$, —$OXC(O)NR_7R_8$, —$OXC(O)NR_7XC(O)OR_8$, —$OXC(O)NR_7XOR_8$, —$OXC(O)NR_7XNR_7R_8$, —$OXC(O)NR_7XS(O)_{0-2}R_9$, —$OXC(O)NR_7XNR_7C(O)R_8$, —$OXC(O)NR_7XC(O)XC(O)OR_8$, —$OXC(O)NR_7R_9$, —$OXC(O)OR_7$, —$OXOR_7$, —$OXR_9$, —$XR_9$, —$OXC(O)R_9$, —$OXS(O)_{0-2}R_9$ and —$OXC(O)NR_7CR_7[C(O)R_8]_2$; wherein X is a selected from a bond and $C_{1-6}$allylene wherein any methylene of X can optionally be replaced with a divalent radical selected from C(O), $NR_7$, $S(O)_2$ and O; $R_7$ and $R_8$ are independently selected from hydrogen, $C_{1-6}$alkyl, $C_{1-6}$alkoxy, halo-substituted-$C_{1-6}$alkyl, halo-substituted-$C_{1-6}$alkoxy, $C_{6-10}$aryl-$C_{0-4}$alkyl, $C_{3-8}$heteroaryl-$C_{0-4}$alkyl, $C_{3-12}$cycloalkyl-$C_{0-4}$alkyl and $C_{3-8}$heterocycloallyl-$C_{0-4}$alkyl; $R_9$ is selected from $C_{6-10}$aryl-$C_{0-4}$alkyl, $C_{5-12}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any alkyl of $R_9$ can have a hydrogen replaced with —$C(O)OR_{10}$; and any aryl, heteroaryl, cycloalkyl or heterocycloalkyl of $R_7$, $R_8$ or $R_9$ is optionally substituted with 1 to 4 radicals independently selected from halo, cyano, hydroxy, $C_{1-6}$alkyl, $C_{3-12}$cycloalkyl, halo-substituted-$C_{1-6}$alkyl, $C_{1-6}$alkoxy, halo-substituted-$C_{1-6}$alkoxy, —$XC(O)OR_{10}$, —$XOR_{10}$, —$XR_{11}$, —$XOR_{11}$, —$XC(O)R_{11}$, —$XNR_{10}C(O)OR_{10}$, —$XNR_{10}C(O)R_{10}$, —$XNR_{10}S(O)_{0-2}R_{10}$, —$XS(O)_{0-2}R_{11}$, —$XC(O)R_{10}$, —$XC(O)NR_{10}R_{11}$, —$XC(O)NR_{10}R_{10}$, —$XC(O)NR_{10}R_{10}$, —$XS(O)_{0-2}NR_{10}R_{10}$ and —$XS(O)_{0-2}R_{10}$; wherein $R_{10}$ is independently selected from hydrogen, $C_{1-6}$alkyl and halo-substituted-$C_{1-6}$alkyl; and $R_{11}$, is independently selected from $C_{6-10}$aryl, $C_{3-8}$heteroaryl, $C_{3-12}$cycloalkyl and $C_{3-8}$heterocycloalkyl;

$R_3$ is selected from $C_{1-10}$alkyl, $C_{1-10}$alkoxy, halo-substituted-$C_{1-10}$alkyl, halo-substituted-$C_{1-10}$alkoxy and $C_{3-12}$cycloalkyl optionally substituted with 1 to 3 $C_{1-6}$alkyl radicals; and the N-oxide derivatives, S-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients. In a third aspect, the present invention provides a method of treating a disease in an animal in which modulation of LXR activity can prevent, inhibit or ameliorate the pathology and/or symptomatology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which LXR activity contributes to the pathology and/or symptomatology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc. "$C_{6-10}$aryl$C_{0-4}$alkyl" means an aryl as described above connected via a alkylene grouping. For example, $C_{6-10}$aryl$C_{0-4}$ alkyl includes phenethyl, benzyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4,5]dec-8-yl, etc.

"Halogen" (or halo) preferably represents chloro or fluoro, but can also be bromo or iodo The term "modulate" with respect to an LXR receptor refers to activation of the LXR receptor and its biological activities associated with the LXR pathway (e.g., transcription regulation of a target gene). Modulation of LXR receptor can be up-regulation (i.e., agonizing, activation or stimulation) or down-regulation (i.e. antagonizing, inhibition or suppression). The mode of action of an LXR modulator can be direct, e.g., through binding to the LXR receptor as a ligand. The modulation can also be indirect, e.g., through binding to and/or modifying another molecule which otherwise binds to and activates the LXR receptor. Thus, modulation of LXR includes a change in the bioactivities of an LXR agonist ligand (i.e., its activity in binding to and/or activating an LXR receptor) or a change in the cellular level of the ligand.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which modulation of LXR activity can prevent, inhibit or ameliorate the pathology and/or symptomatology of the diseases, which method, comprises administering to the animal a therapeutically effective amount of a compound of Formula I.

In one embodiment, with reference to compounds of Formula I, n is selected from 0, 1, 2 and 3.

In another embodiment, $R_1$ is selected from halo, $C_{1-6}$alkyl and halo-substituted-$C_{1-6}$alkyl.

In another embodiment, $R_2$ is selected from $C_{6-10}$aryl-$C_{0-4}$alkyl, $C_{3-8}$heteroaryl-$C_{0-4}$alkyl and $C_{3-12}$cycloalkyl-$C_{0-4}$alkyl; wherein any aryl-alkyl, heteroaryl-alkyl or cycloalkyl-alkyl of $R_2$ is optionally substituted by 1 to 3 radicals independently selected from halo, hydroxyl, $C_{1-6}$alkoxy, halo-substituted-$C_{1-6}$alkyl, halo-substituted-$C_{1-6}$alkoxy, —OXR$_7$, —OXC(O)NR$_7$R$_8$, —OXC(O)NR$_7$XC(O)OR$_8$, —OXC(O)NR$_7$XOR$_8$, —OXC(O)NR$_7$XNR$_7$R$_8$, —OXC(O)NR$_7$XS(O)$_{0-2}$R$_8$, —OXC(O)NR$_7$XNR$_7$C(O)R$_9$, —OXC(O)NR$_7$XC(O)XC(O)OR$_9$, —OXC(O)NR$_7$R$_9$, —OXC(O)OR$_7$, —OXOR$_7$, —OXR$_9$, —XR$_9$, —OXC(O)R$_9$ and —OXC(O)NR$_7$CR$_7$[C(O)R$_5$]$_2$; wherein X is a selected from a bond and $C_{1-6}$alkylene; $R_7$ and $R_8$ are independently selected from hydrogen, cyano, $C_{1-6}$alkyl, halo-substituted-$C_{1-6}$alkyl, $C_{2-6}$alkenyl and $C_{3-12}$cycloalkyl-$C_{0-4}$alkyl; $R_9$ is selected from $C_{6-10}$aryl-$C_{0-4}$alkyl, $C_{5-10}$heteroaryl-$C_{0-4}$-alkyl, $C_{3-12}$cycloalkyl-$C_{0-4}$alkyl and $C_{3-8}$heterocycloalkyl-$C_{0-4}$alkyl; wherein any alkyl of $R_9$ can have a hydrogen replaced with C(O)OR$_{10}$; and any aryl, heteroaryl, cycloalkyl or heterocycloalkyl of $R_9$ is optionally substituted with 1 to 4 radicals independently selected from halo, $C_{1-6}$alkyl, $C_{3-12}$cycloalkyl, halo-substituted-$C_{1-6}$alkyl, $C_{1-6}$alkoxy, halo-substituted-$C_{1-6}$alkoxy, —XC(O)OR$_{10}$, —XC(O)R$_{10}$, —XC(O)NR$_{10}$R$_{10}$, —XS(O)$_{0-2}$NR$_{10}$R$_{10}$ and —XS(O)$_{0-2}$R$_{10}$; wherein $R_{10}$ is independently selected from hydrogen and $C_{1-6}$alkyl; and $R_3$ is selected from $C_{1-10}$alkyl and $C_{3-12}$cycloalkyl optionally substituted with 1 to 3 $C_{1-6}$alkyl radicals.

In another embodiment, $R_1$ is selected from halo, methyl, ethyl and trifluoromethyl; and $R_3$ is selected from t-butyl, methyl-cyclopentyl, 1,1-dimethyl-propyl, 1-ethyl-1-methyl-propyl and methyl-cyclohexyl.

In a further embodiment, $R_2$ is selected from phenyl, benzo[1,3]dioxolyl, cyclopentyl, benzoxazolyl, benzthiazolyl, 2,3- dihydro-benzo[1,4]dioxinyl, 2,3-dihydro-benzofuran, 1H-indazolyl, 1H-indolyl, naphthyl and 2-oxo-2,3-dihydro-1H-indol-5-yl; wherein any aryl-alkyl, heteroaryl-alkyl or cycloalkyl-alkyl of $R_2$ is optionally substituted by 1 to 3 radicals selected from halo, hydroxy, methoxy, trifluoro-methoxy, difluoro-methoxy, ethenyl, methyl-sulfanyl, methyl-carbonyl-amino, formamidyl, trifluoro-methyl, methyl, phenyl, oxazolyl, pyrazolyl, pyrrolidinyl-carbonyl, phenoxy, phenyl-carbonyl, pyridinyl, 1H-indolyl, pyrimidi-nyl, amino-carbonyl, dimethyl-amino, thiophenyl, methyl-sulphanyl, methyl-formamidyl, methyl-carbonyl, ethenyl, phenoxy, methoxy-carbonyl, benzoxy, isopropyl, furanyl, isopropyloxy, [1,3]dioxolanyl and cyano-methyl; wherein any aryl, heteroaryl or heterocycloalkyl substituent of $R_2$ is optionally substituted by 1 to 3 radicals selected from halo, methyl, cyano, carboxy, carboxy-methyl, cyano-methyl, methoxy, carbonyl-methyl, ethyl, trifluoro-methyl, hydroxy, isopropyl, methyl-sulfonyl-amino, dimethyl-amino-carbo-nyl, dimethyl-amino, amino-sulfonyl, chloro-methyl-carbo-nyl-amino, diethyl-amino-carbonyl, 1-oxo-1,3-dihydro-isobenzofuran-5-yl, 4-oxo-piperidin-1-yl-carbonyl, benzyl-formamidyl, morpholino-carbonyl, cyclopropyl-formamidyl, isobutyl-formamidyl, ethyl-formamidyl, butoxy, ethoxy, benzyl, cyclopentyl-formamidyl, 2-methoxy-propionyl, methoxy-methyl-amino-carbonyl, methyl-carbo-nyl-amino, 2-oxo-piperidin-1-yl butyl, t-butyl, methyl-sulfo-nyl-amino, methoxy-methyl, benzo-amino-carbonyl, methoxy-carbonyl, methoxy-carbonyl-ethyl, ethoxy-carbo-nyl, ethoxy-carbonyl-methyl, phenoxy, hydroxy-methyl, t-butoxy-carbonyl, t-butoxy-carbonyl-amino, phenyl-sulfo-nyl, phenyl, acetyl-amino, methyl-sulfonyl, methoxy-carbo-nyl-amino, 1-carboxy-ethyl and trifluoro-methoxy.

Preferred compounds of Formula I are detailed in the Examples and Table I, infra.

Pharmacology and Utility

Compounds of the invention modulate the activity of LXRs and, as such, are useful for treating diseases or disorders in which LXRs contribute to the pathology and/or symptoma-tology of the disease. This invention further provides com-pounds of this invention for use in the preparation of medi-caments for the treatment of diseases or disorders in which LXRs contribute to the pathology and/or symptomatology of the disease. LXR mediated diseases or conditions include inflammation, cardiovascular disease including atherosclero-sis, arteriosclerosis, hypercholesteremia, hyperlipidemia and disorders of glucose homeostasis, including insulin resis-tance, type II diabetes, and obesity.

Lipoprotein metabolism is a dynamic process comprised of the production of triglyceride and cholesterol rich particles from the liver as very low-density lipoprotein (VLDL), modi-fication of these lipoprotein particles within the plasma (VLDL to intermediate density (IDL) to low-density lipopro-tein (LDL)) and clearance of the particles from the plasma, again by the liver. This process provides the transport of triglycerides and free cholesterol to cells of the body. Reverse cholesterol transport is the proposed mechanism by which excess cholesterol is returned to the liver from extra-hepatic tissue.

The process is carried out by high-density lipoprotein (HDL) cholesterol. The combination of lipoprotein produc-tion (VLDL, HDL) from the liver, modification of particles (all) within the plasma and subsequent clearance back to the liver, accounts for the steady state cholesterol concentration in plasma. Compounds of this invention increase reverse cho-lesterol transport by increasing cholesterol efflux from the arteries. This invention includes the use of compounds of this invention for the preparation of a medicament for increasing reverse cholesterol transport. Additionally, this invention pro-vides compounds for inhibiting cholesterol absorption and the use of compounds of this invention for the preparation of a medicament for inhibiting net cholesterol absorption.

The compounds of this invention can also be useful for the prevention or treatment of inflammation and neurodegenera-tive diseases or neurological disorders. Accordingly, this invention also provides a method for preventing or treating inflammation and a method for preventing or treating neuro-degenerative diseases or neurological disorders, particularly neurodegenerative diseases or disorders characterized by neuron degeneration, neuron injury or impaired plasticity or inflammation in the CNS. Particular diseases or conditions that are characterized by neuron degeneration, inflammation, cholesterol and lipid abnormalities in the brain and thus ben-efiting from the growth and/or repair of neurons include stroke, Alzheimer's disease, fronto-temporal dementias (tauopathies), peripheral neuropathy, Parkinson's disease, dementia with Lewy bodies, Huntington's disease, amyo-trophic lateral sclerosis and multiple sclerosis and Niemann-Pick disease. Diseases or conditions that are characterized by neuron degeneration and/or impaired plasticity include psy-chiatric disorders such as schizophrenia and depression. Par-ticular diseases or conditions that are characterized by neu-ronal injury include those conditions associated with brain and/or spinal cord injury, including trauma. In addition, the compounds of this invention can be used to treat or prevent various diseases with an inflammatory component, such as rheumatoid arthritis, osteoarthritis, psoriasis, asthma, etc.

LXR agonists improve glucose tolerance and enhance glut4 expression (U.S. Provisional Patent Application 60/436,112, filed Dec. 23, 2002; U.S. patent application Ser. No. 10/745,334, filed Dec. 22, 2003). There is a coordinated regulation of genes involved in glucose metabolism in liver and adipose tissue. In the liver, LXR agonists inhibit expres-sion of several genes that are important for hepatic gluconeo-genesis, e.g., PGC-1α, phosphoenolpyruvate carboxykinase (PEPCK), and glucose-6-phosphatase expression. Inhibition of these gluconeogenic genes is accompanied by an induction in expression of glucokinase, which promotes hepatic glu-cose utilization. It was also found that glut4 mRNA levels were upregulated by LXR agonists in adipose tissue, and that glucose uptake in 3T3-L1 adipocytes was enhanced in vitro.

In accordance with these discoveries, the present invention provides methods for enhancing glut4 expression in cells in a subject by administering a compound of the invention to the subject. The present invention also provides methods for treating diabetes mellitus and related disorders, such as obe-sity or hyperglycemia, by administering to a subject an effec-tive amount of a compound of the invention to ameliorate the symptoms of the disease. For example, type II diabetes is amenable to treatment with methods of the present invention. By enhancing sensitivity to insulin and glucose uptake by cells, administration with a compound of the invention can also treat other diseases characterized by insulin dysfunction (e.g., resistance, inactivity or deficiency) and/or insufficient glucose transport into cells.

Compounds of the present invention also regulate expres-sion levels of a number of genes that play important roles in liver gluconeogenesis. Accordingly, the present invention fur-ther provides methods for reducing gluconeogenesis in a subject by modulating expression of such genes (e.g., PGC-1 and PEPCK).

In the pancreas, LXR activation stimulates insulin secre-tion via modulation of glucose and lipid metabolism in pan-creatic β-cells, suggesting another mechanism for LXR's anti-diabetic effects. LXR modulators can thus also regulate glucose tolerance by enhancing insulin secretion from the pancreas.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other substances used in the treatment of cardiovascular, inflammatory and/or neurodegenerative diseases. Examples of such compounds include fibrates, TZDs, metformin, etc. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

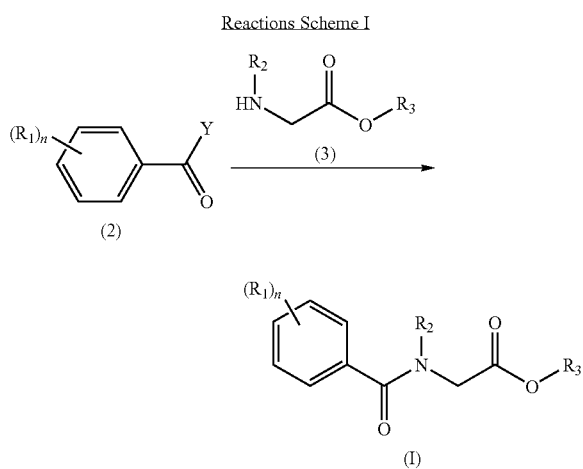

Reaction Scheme I in which N, $R_1$, $R_2$ and $R_3$ are as defined for Formula I in the Summary of the Invention. Compounds of Formula I are prepared by reacting a compound of formula 2 with a compound of formula 3 in the presence of a suitable solvent (e.g., dichloromethane, or the like) and a suitable base (e.g., diisopropylethylamine, or the like). The reaction is carried out in the temperature range of 10 to 40° C. and takes up to 20 hours to complete.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. Resolution of the racemic mixture may be carried out using chiral HPLC. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme 1;

(b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative;

(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

Tert-butyl 2-(2,4,6-trifluoro-N-(3-hydroxyphenyl benzamido)acetate

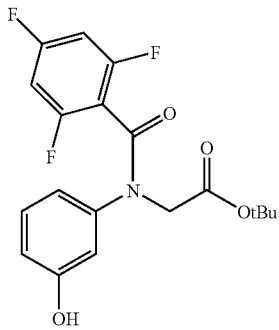

To a solution of 3-aminophenol (4.58 mmol) in DMF (15 mL) is added N,N-diisopropylethyl amine (4.58 mmol) and tert-butylbromoacetate (4.58 mmol) and the reaction mixture is stirred at 50° C. for 2 hours. Ethyl acetate and water are added to the reaction mixture and the phases are separated. The organic phase is dried on sodium sulfate, filtered and the solvent evaporated. The tert-butyl 2-(3-hydroxyphenylamino) acetate obtained is used as such in the next step without further purification.

To a solution in $CH_2Cl_2$ (15 mL) of tert-butyl 2-(3-hydroxyphenylamino)acetate obtained in the previous step, is added N,N-diisopropylethyl amine (9.16 mmol) followed by dropwise addition of 2,4,6-trifluorobenzoyl chloride (9.16 mmol). The reaction mixture is stirred for 12 hours at room temperature. After concentration and redissolution in DMSO, the residue is purified by preparative LCMS (10 to 90% $CH_3CN$) to give tert-butyl 2-(2,4,6-trifluoro-N-(3-hydroxyphenyl) benzamido)acetate: $^1H$ NMR (400 MHz, $CDCl_3$) δ 7.06 (t, J=8.4 Hz, 1H), 6.78 (s, 2H), 6.69 (d, J=8 Hz, 1H), 6.48 (t, J=8 Hz, 2H), 5.85 (bs, 1H), 4.42 (s, 2H), 1.49 (s, 9H);
MS: $(ES^+)$ 382.1 $(M+1)^+$.

Example 2

Tert butyl 2-(N-(3-(2,6-dimethoxyphenyl phenol)-2,6-difluorobenzamido)acetate

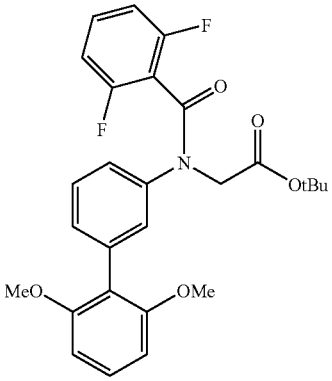

To a solution of 3-bromoaniline (69.8 mmol) in 200 mL of $CH_2Cl_2$ under nitrogen atmosphere, is added N,N-diisopropylethyl amine (69.8 mmol) followed by dropwise addition of 2,6-difluorobenzoylchloride (69.8 mmol). The reaction mixture is stirred at room temperature for hours. TLC (hexanes: ethyl acetate=8:2) and analytical LCMS (20 to 100% $CH_3CN$) reveal the complete conversion of the starting material to the product. Water is added to the reaction mixture and the phases are separated. The organic layer is dried on sodium sulfate, filtered and the solvent is evaporated. The product, N-(3-bromophenyl)-2,6-difluorobenzamide, is used without further purification in the next step.

To a solution of N-(3-bromophenyl)-2,6-difluorobenzamide in 200 mL of DMF at room temperature and under nitrogen atmosphere, NaH 60% in oil dispersion (104.7 mmol) is slowly added and the reaction mixture is stirred for 30 minutes. Tert-butylbromoacetate (104.7 mmol) is added and the reaction stirred at room temperature. After 12 hours the reaction is complete by TLC (hexanes:ethyl acetate=8:2) and analytical LCMS (20 to 100% $CH_3CN$). Ethyl acetate and water are added to the reaction mixture and the phases are separated. The organic phase is dried on sodium sulfate, filtered and the solvent is evaporated. The crude is purified by automated column chromatography (gradient of hexanes and ethyl acetate) to give tert-butyl 2-(N-(3-bromophenyl)-2,6-difluorobenzamido)acetate: $^1H$ NMR (400 MHz, $CDCl_3$) δ 7.36 (bs, 1H), 7.20 (m, 1H), 7.07 (m, 2H), 6.96 (t, J=8 Hz, 1H), 6.62 (td, J=8 Hz, $J_2$=1.2 Hz), 4.32 (s, 2H), 1.39 (s, 9H);
MS: $(ES^+)$ 448.0 $(M+23)^+$.

Tert-butyl 2-(N-(3-bromophenyl)-2,6-difluorobenzamido)acetate (0.55 mmol) is mixed with 2,6-dimethoxyphenyl boronic acid (6.13 mmol) and $Pd(Ph_3P)_4$ (0.024 mmol). To the solid mixture under nitrogen, $Na_2CO_3$ 2M (0.83 mL) is added followed by DMF (5.6 mL). The reaction mixture is stirred at room temperature for 1 hour and then heated at 85° C. for 12 hours. The reaction mixture is purified by automated column chromatography (gradient of hexanes and ethyl acetate) to give tert-butyl 2-(N-(3-(2,6-dimethoxyphenyl) phenyl)-2,6-difluorobenzamido)acetate: $^1H$ NMR (400 MHz, $CDCl_3$) δ7.19 (m, 6H), 6.69 (t, J=7.2 Hz, 2H), 6.58 (d. J=8.4 Hz, 2H), 4.46 (s, 2H), 3.64 (s, 6H), 1.48 (s, 9H); MS: $(ES^+)$ 484.1 $(M+23)^+$.

Example 3

Tert-butyl 2-(2,6-difluoro-N-(3-(4-carboxybenzyloxyphenyl)benzamido)acetate

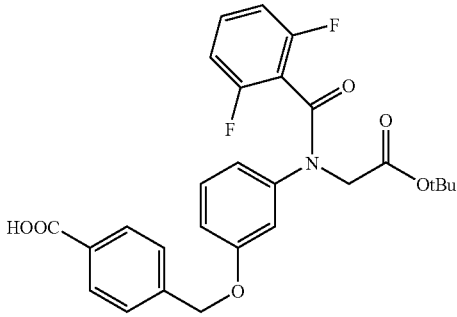

To a solution of 3-aminophenol (6.98 mmol) in 20 mL of $CH_2Cl_2$ under nitrogen atmosphere, is added N,N-diisopropylethyl amine (6.98 mmol) followed by dropwise addition of 2,6-difluorobenzoylchloride (6.98 mmol). The reaction mixture is stirred at room temperature for 5 hours and the product 2,6-difluoro-N-(3-hydroxyphenyl)benzamide is purified by preparative HPLC: $^1H$ NMR (400 MHz, DMSO) δ 10.68 (s, 1H), 9.55 (bs, 1H), 7.57 (m, 1H), 7.28 (m, 1H), 7.23 (m, 2H), 7.12 (t, J=8 Hz, 1H), 7.05 (m, 1H), 6.54 (m, 1H).

A solution of 2,6-difluoro-N-(3-hydroxyphenyl)benzamide (0.9 mmol) in 4 mL of CH$_3$CN is treated with potassium carbonate (1.36 mmol) and methyl 4-(bromomethyl)benzoate. The reaction mixture is heated at 80° C. for 48 hours. The solvent is evaporated and the O-alkylated product 2,6-difluoro-N-(3-(4-carbomethoxybenzyloxyphenyl)benzamide is obtained after purification with automated column chromatography (gradient of hexanes and ethyl acetate).

To a solution of 2,6-difluoro-N-(3-(4-carbomethoxybenzyloxyphenyl)benzamide (0.61 mmol) in 4 mL of DMF, first NaH 60% in oil dispersion (0.73 mmol) and after 30 minutes tert-butylbromoacetate (0.67 mmol) are added. The reaction is stirred at room temperature for 12 hours. LCMS analysis (10 to 90% CH$_3$CN) of the reaction mixture reveals that the reaction is complete. DMF is evaporated and the crude tert-butyl 2-(2,6-difluoro-N-(3-(4-carbomethoxybenzyloxy)phenyl)benzamido)acetate is finally dissolved in 4 mL of MeOH and treated with LiOH 3M (1.95 mmol). The reaction mixture is purified by preparative LCMS (10 to 90% CH$_3$CN) to give tert-butyl 2-(2,6-difluoro-N-(3-(4-carboxybenzloxy)phenyl)-benzamido)acetate: $^1$H NMR (400 MHz, CDCl$_3$) δ 8.12 (d, J=8.4 Hz, 2H), 7.46 (d, J=8.4 Hz, 2H), 7.13 (m, 2H), 6.91 (m, 2H), 6.81 (m, 1H), 6.70 (m, 2H), 5.05 (s, 2H), 4.45 (s, 2H), 1.51 (s, 9H); MS: (ES$^+$) 498.1 (M+1)$^+$.

By repeating the procedures described in the above examples, using appropriate starting materials, the following compounds of Formula I, as identified in Table 1 and Table 2, are obtained.

TABLE 1

| Compound number | Structure | MS (m/z) (M + 1)$^+$ | NMR |
| --- | --- | --- | --- |
| 4 | 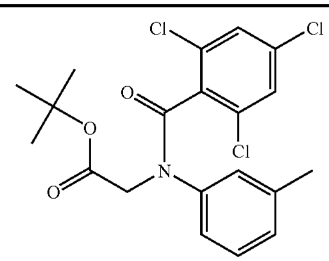 | 428.0 | $^1$H NMR (400 MHz, CDCl$_3$) δ 6.88 (m, 6H), 4.23 (s, 2H), 2.02 (s, 3H), 1.26 (s, 9H). |
| 5 | 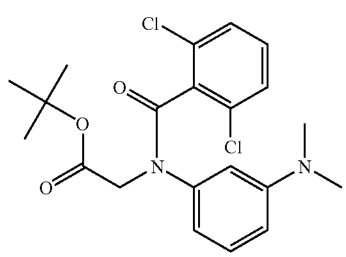 | 423.1 | $^1$H NMR (400 MHz, CDCl$_3$) δ 6.93 (d, J=1.6 Hz, 2H), 6.85 (m, 2H), 6.61 (m, 2H), 6.32 (m, 1H), 4.29 (s, 2H), 2.65 (s, 6H), 1.31 (s, 9H). |
| 6 | 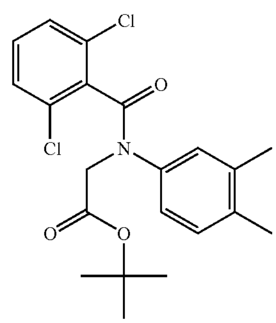 | 408.1 | $^1$H NMR (400 MHz, CDCl$_3$) δ 7.05 (m, 5H), 6.84 (d, J=8 Hz, 1H), 4.39 (s, 2H), 2.05 (s, 6H), 1.42 (s, 9H). |
| 7 | 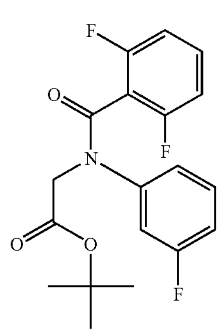 | 366.1 | $^1$H NMR (400 MHz, CDCl$_3$) δ 7.05 (m, 6H), 6.73 (m, 1H), 4.45 (s, 2H), 1.56 (s, 9H). |

TABLE 1-continued

| Compound number | Structure | MS (m/z) (M + 1)+ | NMR |
|---|---|---|---|
| 8 | 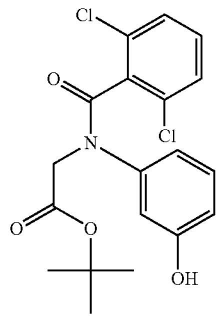 | 396.1 | $^1$H NMR (400 MHz, CDCl$_3$) δ 7.06 (m, 6H), 6.6 (m, 1H), 4.48 (s, 2H), 1.50 (s, 9H). |
| 9 | 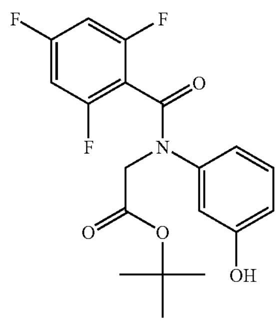 | 382.1 | $^1$H NMR (400 MHz, CDCl$_3$) δ 7.06 (t, J=8.4 Hz, 1H), 6.78 (s, 2H), 6.69 (d, J=8 Hz, 1H), 6.48 (t, J=8 Hz, 2H), 5.85 (bs, 1H), 4.42 (s, 2H), 1.49 (s, 9H). |
| 10 | 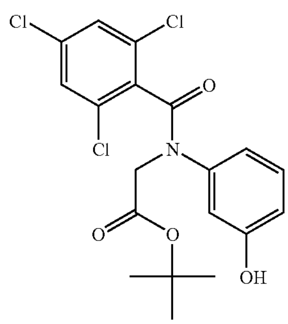 | 430.0 | $^1$H NMR (400 MHz, CDCl$_3$) δ 7.07 (s, 2H), 6.95 (m, 3H), 6.62 (m, 1H), 4.37 (s, 2H), 1.42 (s, 9H). |
| 11 | 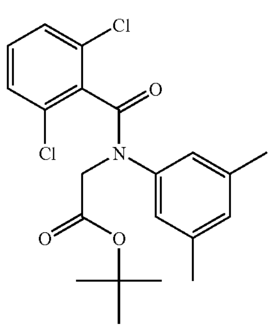 | 408.1 | $^1$H NMR (400 MHz, CDCl$_3$) δ 7.18 (s, 1H), 7.04 (d, J=1.6 Hz, 1H), 6.98 (s, 2H), 6.96 (d, J=2.4 Hz, 1H), 6.71 (s, 1H), 4.40 (s, 2H), 2.10 (s, 6H), 1.43 (s, 9H). |
| 12 | 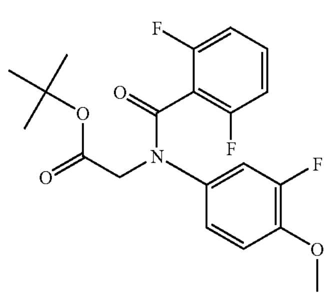 | 418.1 (M + 23)+ | $^1$H NMR (400 MHz, CDCl$_3$) δ 7.19 (m, 1H), 7.1 (m, 2H), 6.78 (m, 3H), 4.41 (s, 2H), 3.81 (s, 3H), 1.51 (s, 9H). |

TABLE 1-continued
| Compound number | Structure | MS (m/z) (M + 1)+ | NMR |
|---|---|---|---|
| 13 | 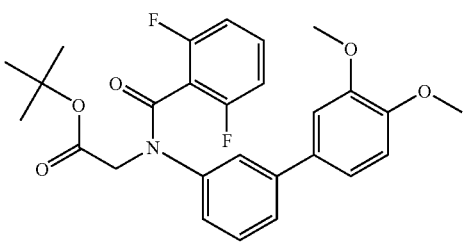 | 484.1 | ¹H NMR (400 MHz, CDCl$_3$) δ 7.19 (m, 6H), 6.69 (t, J=7.2 Hz, 2H), 6.58 (d, J=8.4 Hz, 2H), 4.46 (s, 2H), 3.64 (s, 6H), 1.48 (s, 9H). |
| 14 | 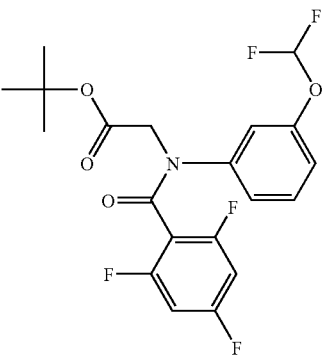 | 454.1 (M + 23)+ | ¹H NMR (400 MHz, CDCl$_3$) δ 7.25 (t, J=8.4 Hz, 1H), 7.14 (m, 2H), 6.99 (dd, J$_1$=1.6 Hz, J$_2$=8.4 Hz, 1H), 6.53 (m, 2H), 6.41 (t, J$_1$=73.2 Hz, 1H), 4.44 (s, 2H), 1.52 (s, 9H). |
| 15 | 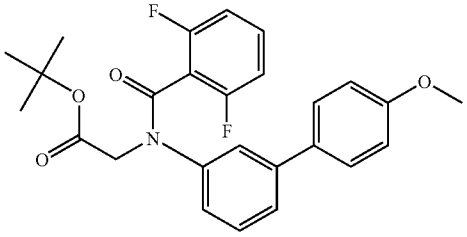 | 454.1 | ¹H NMR (400 MHz, CDCl$_3$) δ 7.36 (s, 1H), 7.23 (m, 3H), 7.11 (m, 3H), 6.82 (d, J=8.8 Hz, 2H), 6.59 (t, J=7.2 Hz, 2H), 4.38 (s, 2H), 3.72 (s, 3H), 1.39 (s, 9H). |
| 16 | 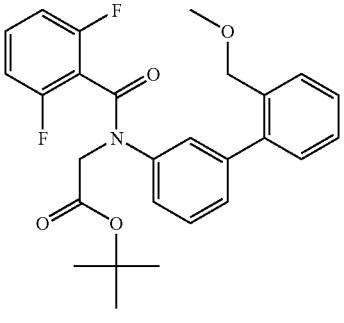 | 490.1 (M + 23)+ | ¹H NMR (400 MHz, CDCl$_3$) δ 7.39 (d, J=7.6 Hz, 1H), 7.27 (t, J=7.6 Hz, 1H), 7.23 (m, 4H), 7.13 (m, 2H), 6.94 (d, J=7.6 Hz, 1H), 6.65 (t, J=7.6 Hz, 2H), 4.41 (s, 2H), 4.04 (s, 2H), 3.15 (s, 3H), 1.4 (s, 9H). |
| 17 | 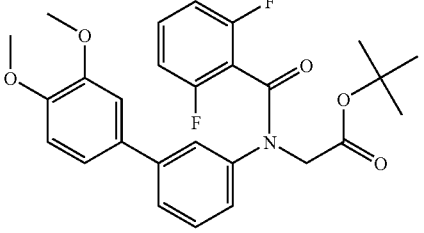 | 484.1 | ¹H NMR (400 MHz, CDCl$_3$) δ 7.49 (s, 1H), 7.36 (m, 1H), 7.26 (m, 3H), 6.98 (dd, J=2 Hz, 1H), 6.91 (m, 2H), 6.72 (m, 2H), 4.51 (s, 2H), 3.94 (s, 3H), 3.92 (s, 3H), 1.52 (s, 9H). |

TABLE 1-continued

| Compound number | Structure | MS (m/z) (M + 1)+ | NMR |
|---|---|---|---|
| 18 | 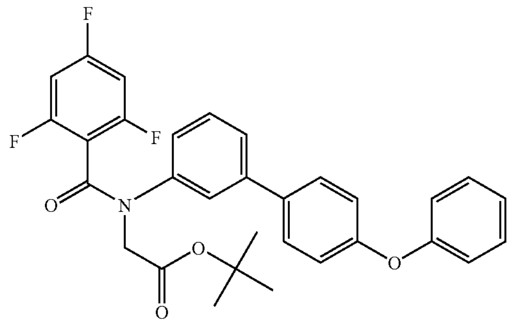 | 556.2 (M + 23)+ | ¹H NMR (400 MHz, CDCl₃) δ 7.49 (s, 1H), 7.43 (m, 5H), 7.29 (t, J=7.6 Hz, 1H), 7.23 (m, 1H), 7.15 (t, J=7.6 Hz, 1H), 7.07 (m, 4H), 6.52 (m, 2H), 4.49 (s, 2H), 1.52 (s, 9H). |
| 19 | 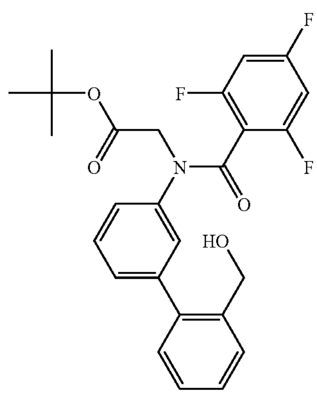 | 494.1 (M + 23)+ | ¹H NMR (400 MHz, CDCl₃) δ 7.53 (d, J=5.6 Hz, 1H), 7.22 (m, 6H), 6.89 (dd, J₁=7.6 Hz, J₂=1.2 Hz, 1H), 6.31 (m, 2H), 4.29 (s, 2H), 4.2 (s, 2H), 1.29 (s, 9H). |
| 20 | 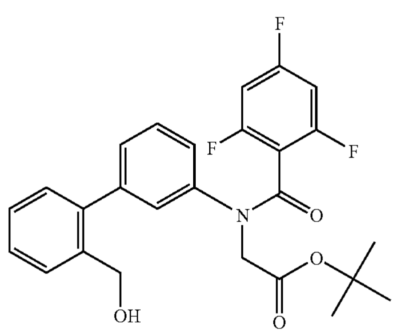 | 494.1 (M + 23)+ | ¹H NMR (400 MHz, CDCl₃) δ 7.53 (d, J=7.2 Hz, 1H), 7.40 (t, J=7.6 Hz, 1H), 7.36 (m, 5H), 6.53 (t, J=8.8 Hz, 2H), 4.49 (s, 2H), 4.40 (s, 2H), 1.49 (s, 9H). |
| 21 | 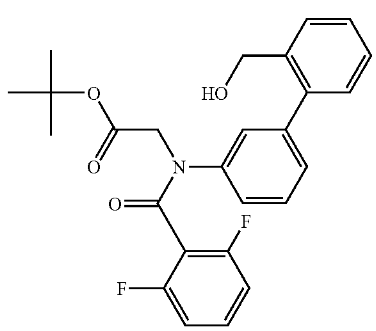 | 476.1 (M + 23)+ | ¹H NMR (400 MHz, CDCl₃) δ 7.53 (d, J=7.6 Hz, 1H), 7.39 (t, J=7.6 Hz, 1H), 7.35 (m, 4H), 7.22 (m, 2H), 7.07 (d, J=7.6 Hz, 1H), 6.76 (t, J=7.6 Hz, 2H), 4.51 (s, 2H), 4.36 (s, 2H), 1.5 (s, 9H). |

TABLE 1-continued

| Compound number | Structure | MS (m/z) (M + 1)+ | NMR |
|---|---|---|---|
| 22 | 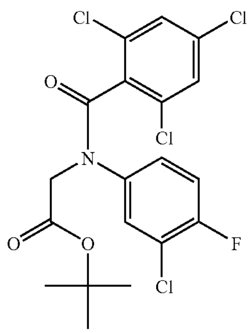 | 466.0 | ¹H NMR (400 MHz, CDCl₃) δ 7.59 (m, 1H), 7.37 (m, 1H), 7.19 (s, 2H), 6.99 (t, J=8.8 Hz, 1H), 4.44 (s, 2H), 1.49 (s, 9H). |
| 23 | 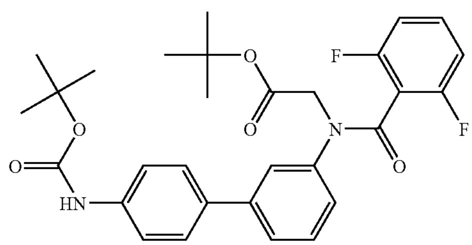 | 539.2 | ¹H NMR (400 MHz, CDCl₃) δ 7.63 (s, 1H), 7.4 (m, 8H), 6.87 (m, 2H), 6.70 (s, 1H), 4.66 (s, 2H), 1.68 (s, 9H), 1.67 (s, 9H). |
| 24 | 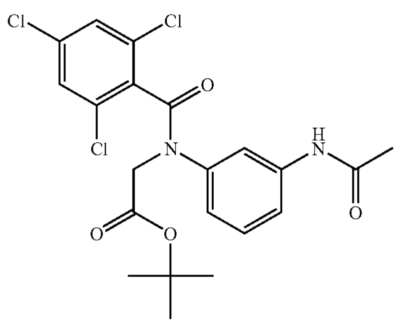 | 471.0 | ¹H NMR (400 MHz, CDCl₃) δ 7.66 (s, 1H), 7.40 (m, 1H), 7.33 (s, 1H), 7.15 (m, 1H), 7.14 (s, 2H), 4.47 (s, 2H), 2.15 (s, 3H), 1.49 (s, 9H). |
| 25 | 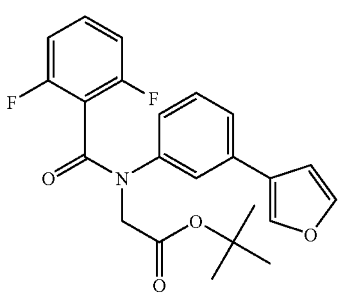 | 414.1 | ¹H NMR (400 MHz, CDCl₃) δ 7.71 (s, 1H), 7.53 (t, J=1.6 Hz, 1H), 7.36 (s, 1H), 7.33 (m, 4H), 6.79 (m, 2H), 6.65 (m, 1H), 4.57 (s, 2H), 1.59 (s, 9H). |
| 26 | 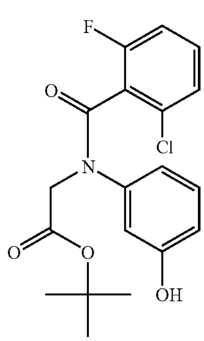 | 380.1 | ¹H NMR (400 MHz, CDCl₃) δ 7.81 (m, 1H), 7.68 (m, 1H), 7.55 (m, 2H), 7.42 (m, 2H), 7.20 (m, 1H), 5.04 (d, J=16.8 Hz, 1H), 4.95 (d, J=16.8 Hz, 1H), 2.07 (s, 9H). |

TABLE 1-continued

| Compound number | Structure | MS (m/z) (M + 1)+ | NMR |
|---|---|---|---|
| 27 | 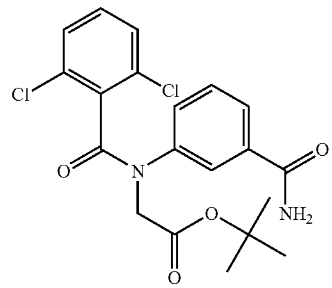 | 445 (M + 23)+ | ¹H NMR (400 MHz, CDCl₃) δ 7.86 (t, J=1.6 Hz, 1H), 7.58 (m, 2H), 7.23 (t, J=8 Hz, 1H), 7.01 (m, 3H), 5.95 (bs, 1H), 5.62 (bs, 1H), 4.46 (s, 2H), 1.41 (s, 9H). |
| 28 | 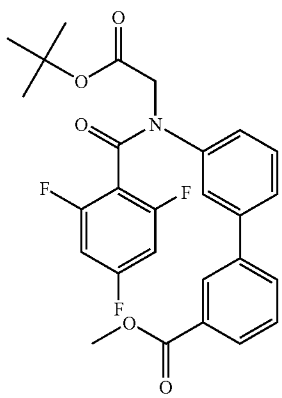 | 444.1 (M − 55)+ | ¹H NMR (400 MHz, CDCl₃) δ 8.09 (s, 1H), 8.07 (d, J=7.6 Hz, 1H), 7.63 (d, J=8 Hz, 1H), 7.53 (m, 3H), 7.34 (t, J=7.6 Hz, 1H), 7.27 (d, J=8 Hz, 2H), 6.52 (t, J=8 Hz, 2H), 4.51 (s, 2H), 3.96 (s, 3H), 1.51 (s, 9H). |
| 29 | 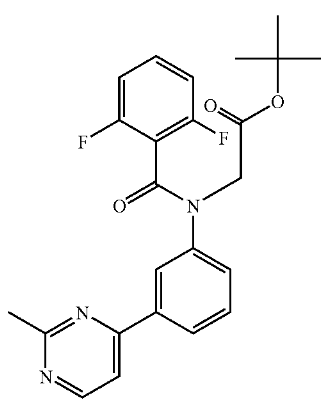 | 440.1 | ¹H NMR (400 MHz, CDCl₃) δ 8.82 (d, J=5.2 Hz, 1H), 8.20 (s, 1H), 8.09 (dd, J₁=1.2 Hz, J₂=6 Hz, 1H), 7.49 (m, 3H), 7.28 (m, 1H), 6.85 (m, 2H), 4.65 (s, 2H), 2.95 (s, 3H), 1.69 (s, 9H). |
| 30 | 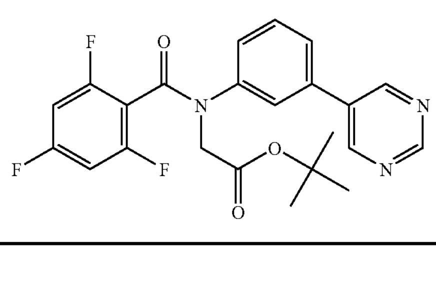 | 444.1 | ¹H NMR (400 MHz, CDCl₃) δ 9.24 (s, 1H), 8.84 (s, 2H), 7.55 (s, 1H), 7.47 (m, 3H), 6.52 (t, J=7.6 Hz, 2H), 4.50 (s, 2H), 1.51 (s, 9H). |

TABLE 2

| Compound number | Structure | MS (m/z) (M + 1)+ |
|---|---|---|
| 31 | 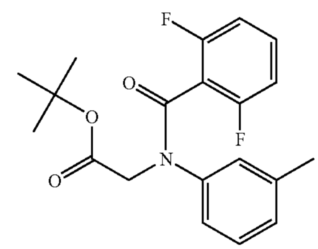 | 384.1 (M + 23)+ |
| 32 | 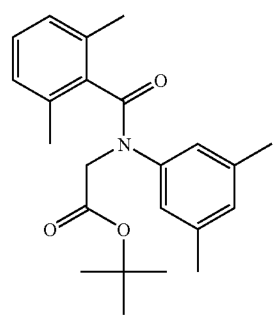 | 368.2 |
| 33 | 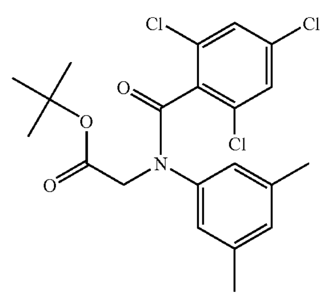 | 442.0 |
| 34 | 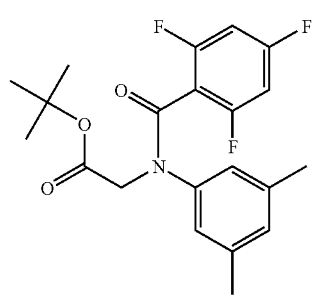 | 394.1 |
| 35 | 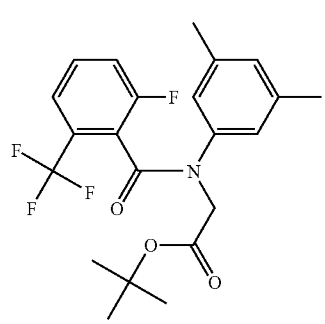 | 426.1 |

TABLE 2-continued

| Compound number | Structure | MS (m/z) (M + 1)+ |
|---|---|---|
| 36 | 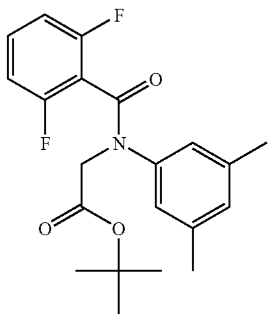 | 376.2 |
| 37 | 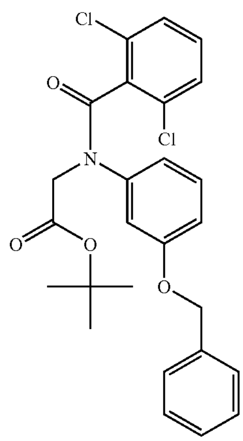 | 486.1 |
| 38 | 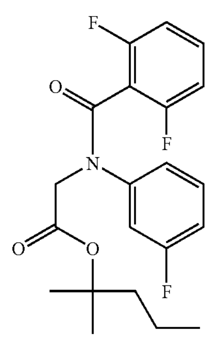 | 416.1 (M + 23)+ |
| 39 | 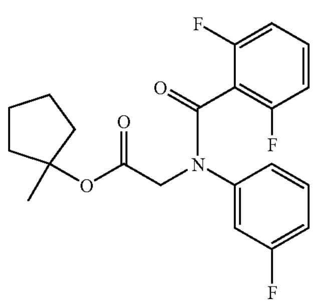 | 414.1 (M + 23)+ |

TABLE 2-continued

| Compound number | Structure | MS (m/z) (M + 1)+ |
|---|---|---|
| 40 | 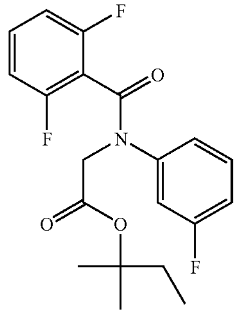 | 402.1 (M + 23)+ |
| 41 | 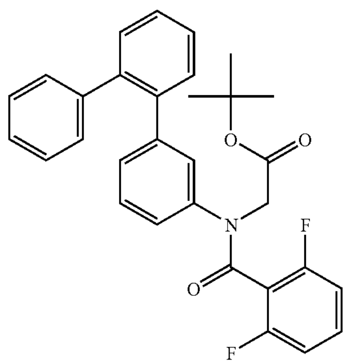 | 500.2 |
| 42 | 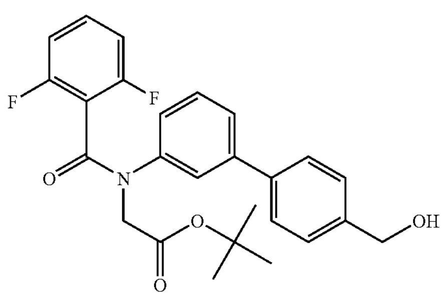 | 454.1 |
| 43 | 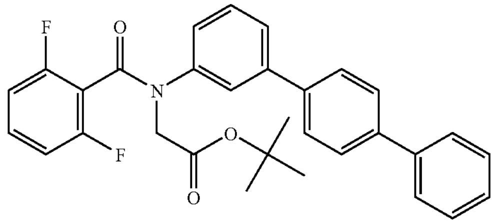 | 500.2 |
| 44 | 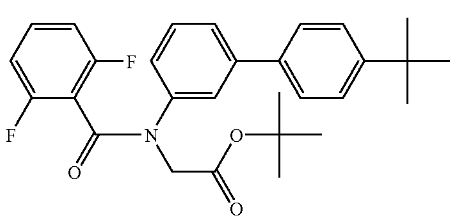 | 502.2 (M + 23)+ |

TABLE 2-continued

| Compound number | Structure | MS (m/z) (M + 1)+ |
|---|---|---|
| 45 | 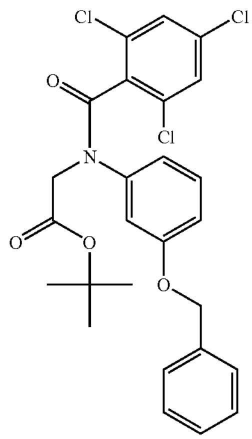 | 520.0 |
| 46 | 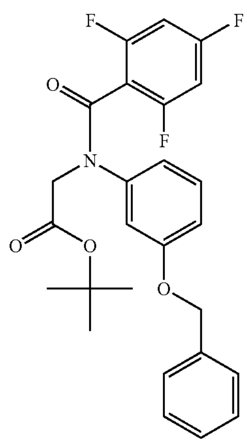 | 472.1 |
| 47 | 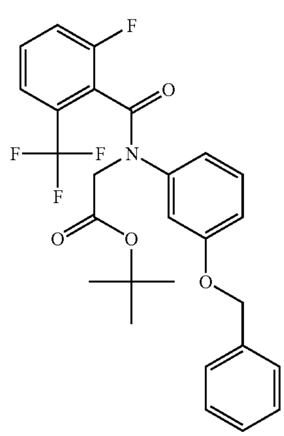 | 504.1 |

TABLE 2-continued

| Compound number | Structure | MS (m/z) (M + 1)+ |
|---|---|---|
| 48 | 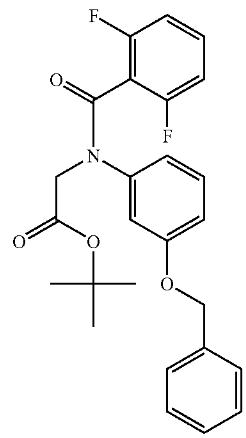 | 454.1 |
| 49 | 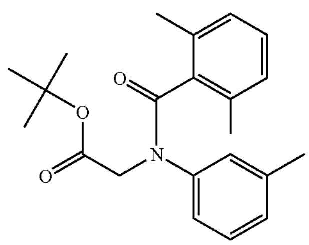 | 354.2 |
| 50 | 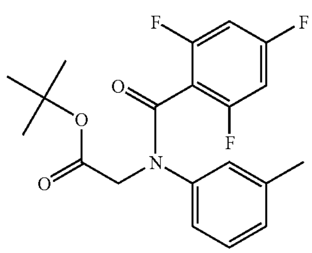 | 380.1 |
| 51 | 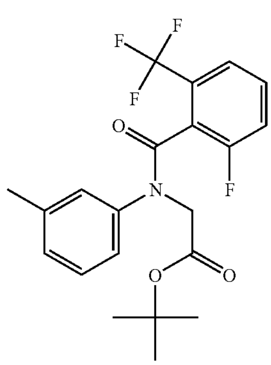 | 412.1 |
| 52 | 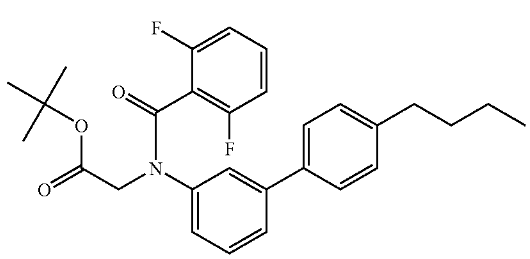 | 480.2 |

TABLE 2-continued

| Compound number | Structure | MS (m/z) (M + 1)+ |
|---|---|---|
| 53 | 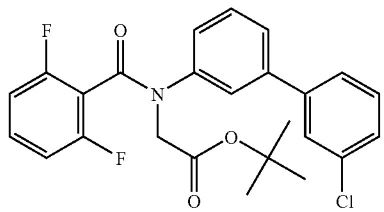 | 458.1 |
| 54 | 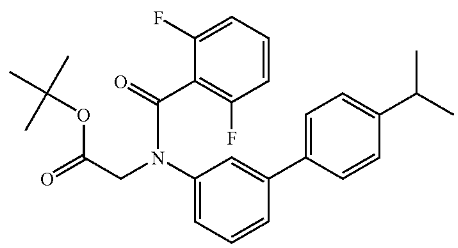 | 466.2 |
| 55 | 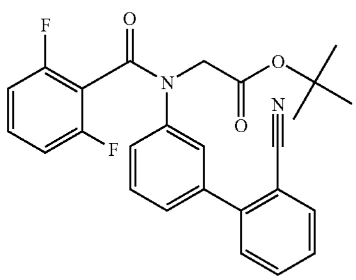 | 449.1 |
| 56 | 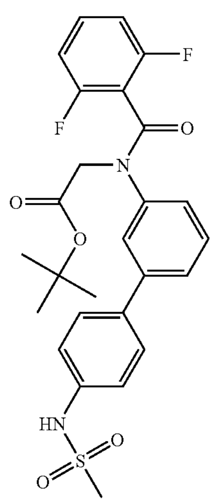 | 461.1 (M − 55)+ |
| 57 | 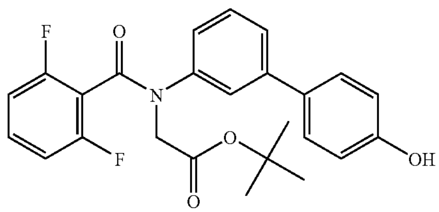 | 440.1 |

TABLE 2-continued

| Compound number | Structure | MS (m/z) (M + 1)+ |
|---|---|---|
| 58 | 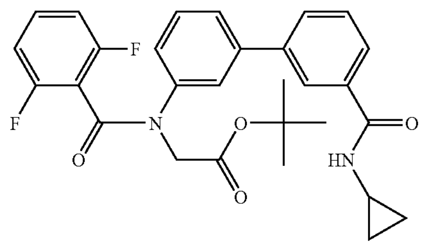 | 507.3 |
| 59 | 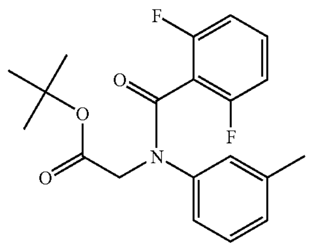 | 362.2 |
| 60 | 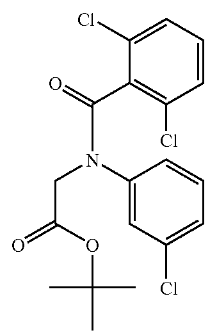 | 414.0 |
| 61 | 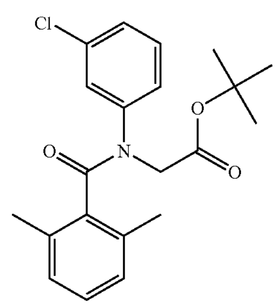 | 374.2 |
| 62 | 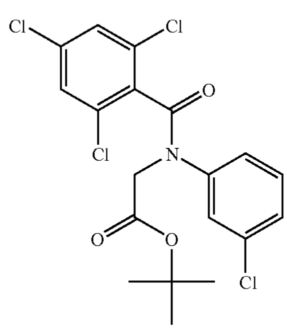 | 448.0 |

TABLE 2-continued
| Compound number | Structure | MS (m/z) (M + 1)+ |
|---|---|---|
| 63 | 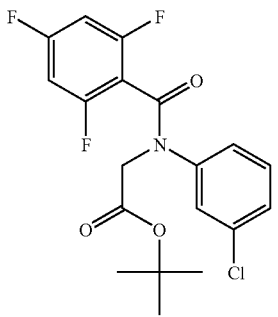 | 400.1 |
| 64 | 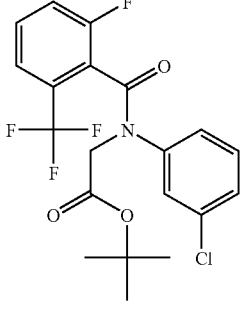 | 432.1 |
| 65 | 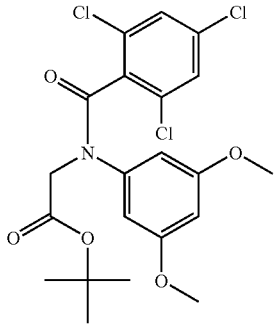 | 474.0 |
| 66 | 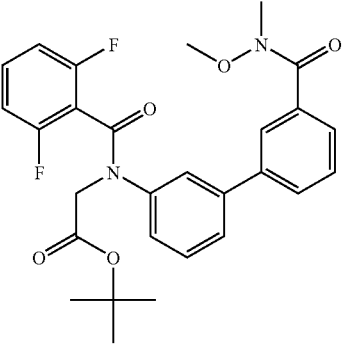 | 455.1 (M − 55)+ |

TABLE 2-continued

| Compound number | Structure | MS (m/z) (M + 1)+ |
|---|---|---|
| 67 | 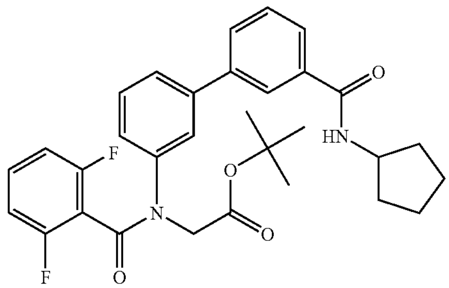 | 479.2 (M − 55)+ |
| 68 | 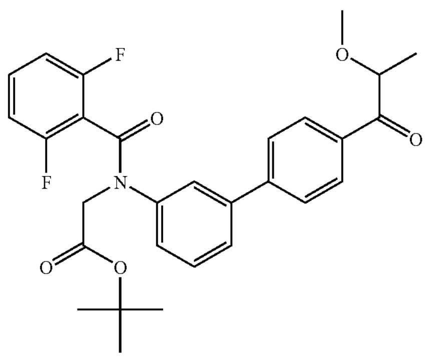 | 454.1 (M − 55)+ |
| 69 | 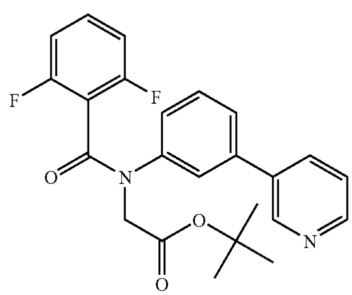 | 425.2 |
| 70 | 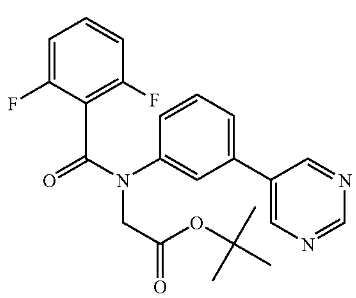 | 426.2 |
| 71 | 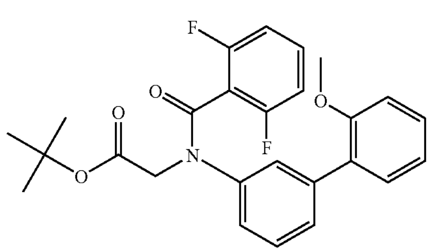 | 454.2 |

TABLE 2-continued

| Compound number | Structure | MS (m/z) (M + 1)+ |
| --- | --- | --- |
| 72 | 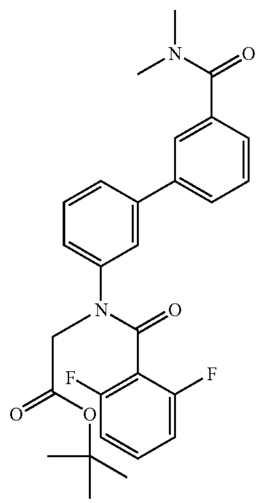 | 495.2 |
| 73 | 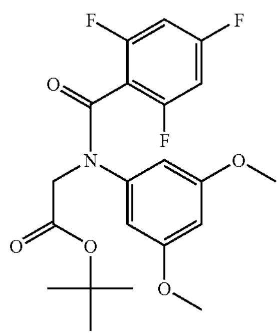 | 426.1 |
| 74 | 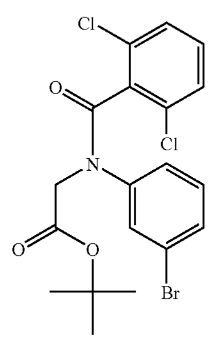 | 458.0 |
| 75 | 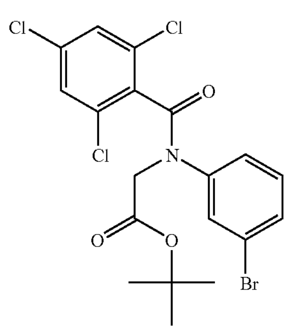 | 491.9 |

TABLE 2-continued

| Compound number | Structure | MS (m/z) (M + 1)+ |
|---|---|---|
| 76 | 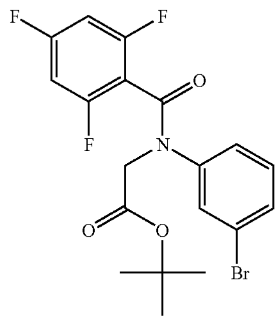 | 444.0 |
| 77 | 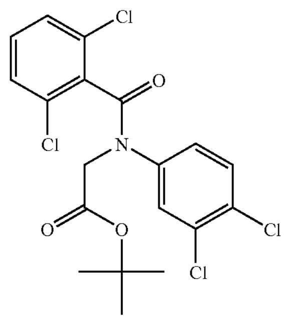 | 448.0 |
| 78 | 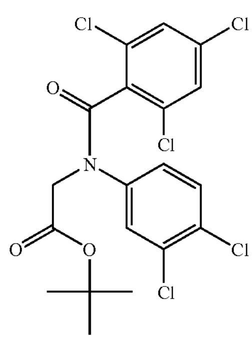 | 481.9 |
| 79 | 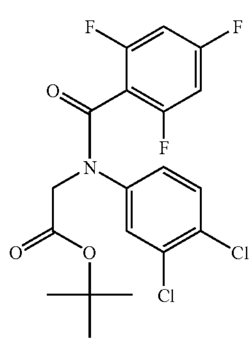 | 434.0 |

TABLE 2-continued

| Compound number | Structure | MS (m/z) (M + 1)+ |
|---|---|---|
| 80 | 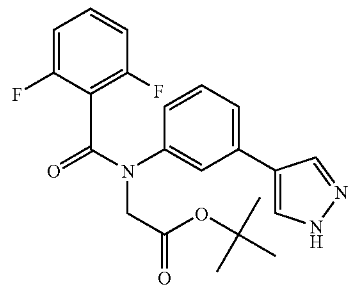 | 414.1 |
| 81 | 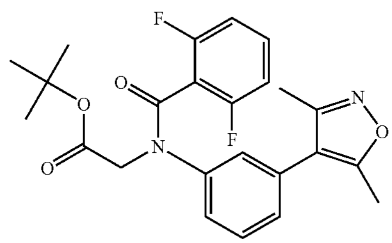 | 443.2 |
| 82 | 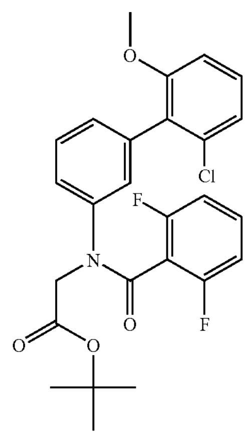 | 488.1 |
| 83 | 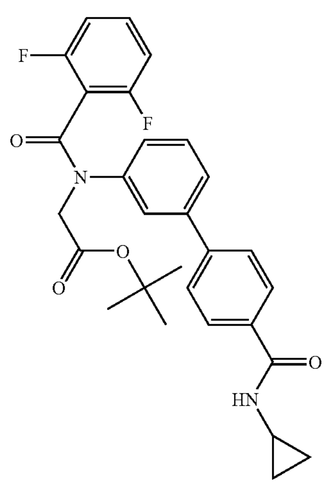 | 507.2 |

TABLE 2-continued

| Compound number | Structure | MS (m/z) (M + 1)+ |
|---|---|---|
| 84 | 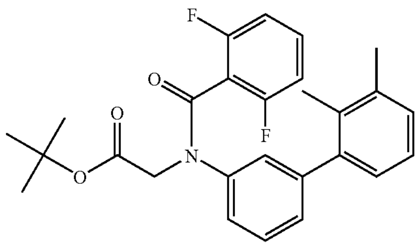 | 452.2 |
| 85 | 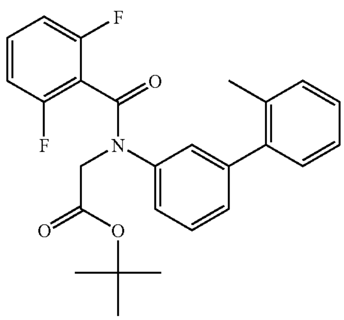 | 437.9 |
| 86 | 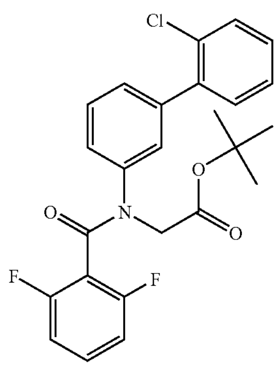 | 458.1 |
| 87 | 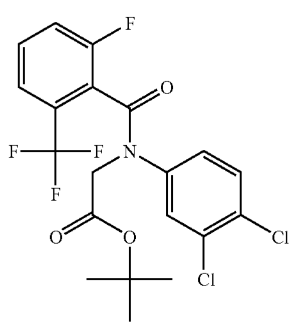 | 466.0 |
| 88 | 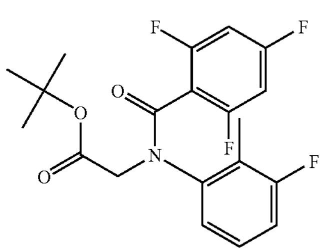 | 398.1 |

TABLE 2-continued

| Compound number | Structure | MS (m/z) (M + 1)+ |
|---|---|---|
| 89 | 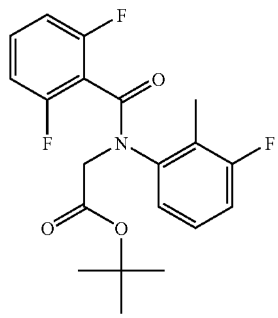 | 380.1 |
| 90 | 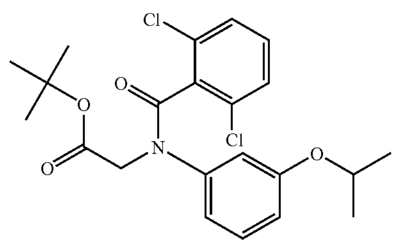 | 438.1 |
| 91 | 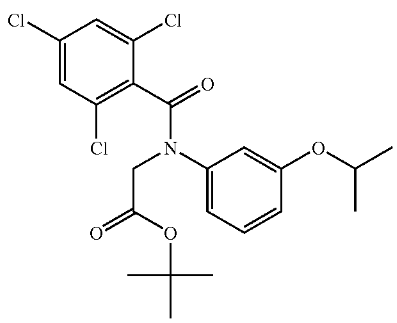 | 472.0 |
| 92 | 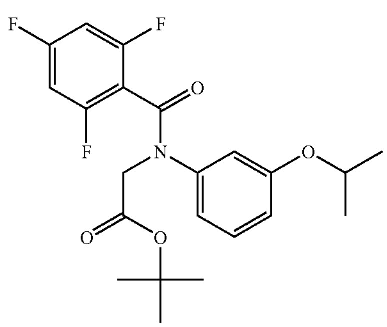 | 424.2 |

TABLE 2-continued

| Compound number | Structure | MS (m/z) (M + 1)+ |
|---|---|---|
| 93 | 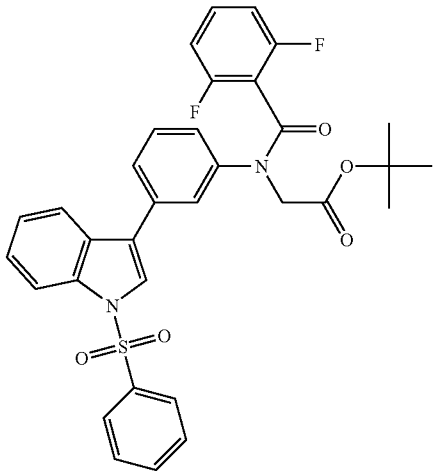 | 603.2 |
| 94 | 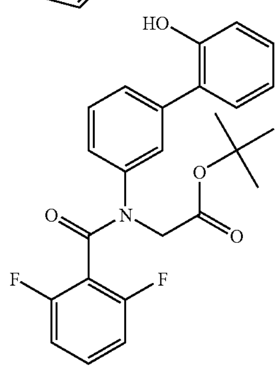 | 440.2 |
| 95 | 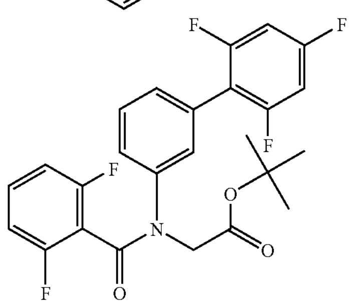 | 478.2 |
| 96 | 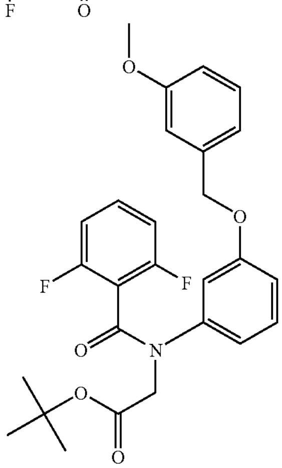 | 428.1 (M − 55)+ |

TABLE 2-continued
| Compound number | Structure | MS (m/z) (M + 1)+ |
|---|---|---|
| 97 | 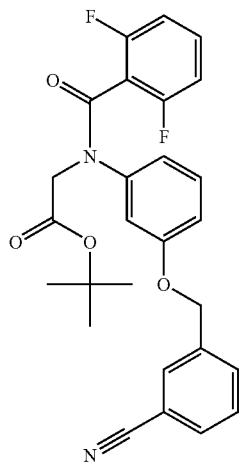 | 423.1 (M − 55)+ |
| 98 | 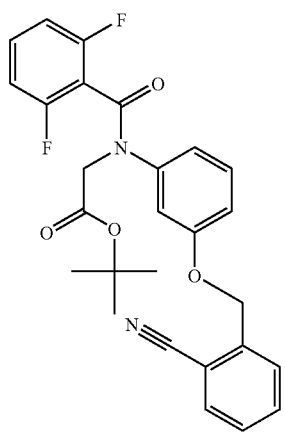 | 423.1 (M − 55)+ |
| 99 | 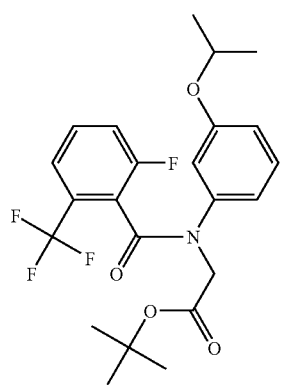 | 456.1 |

TABLE 2-continued

| Compound number | Structure | MS (m/z) (M + 1)+ |
|---|---|---|
| 100 | 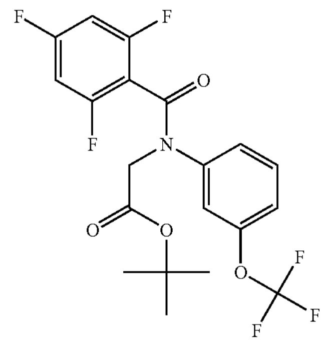 | 450.1 |
| 101 | 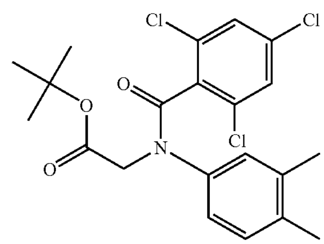 | 442.0 |
| 102 | 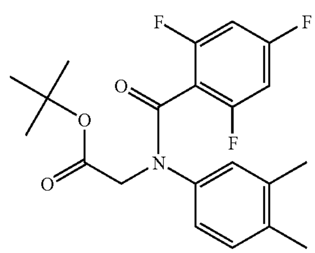 | 394.2 |
| 103 | 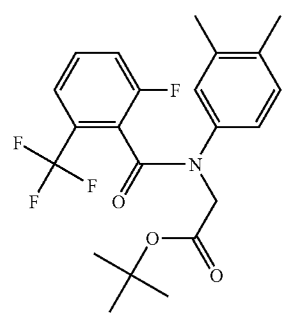 | 426.2 |
| 104 | 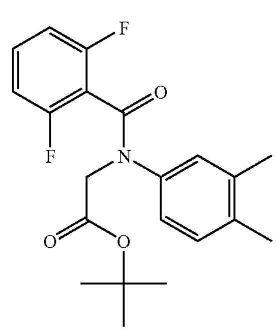 | 376.1 |

TABLE 2-continued

| Compound number | Structure | MS (m/z) (M + 1)+ |
|---|---|---|
| 105 | 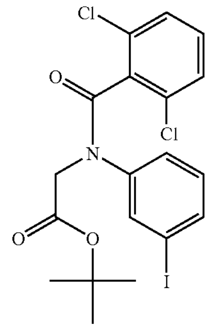 | 505.9 |
| 106 | 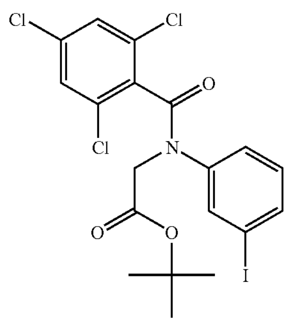 | 540.1 |
| 107 | 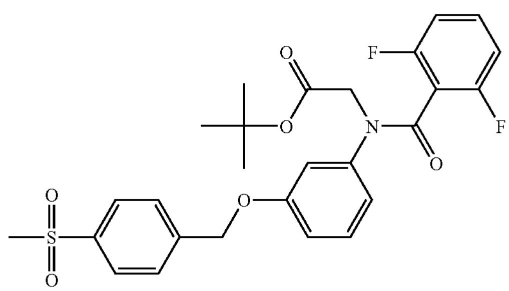 | 476.1 (M − 55)+ |
| 108 | 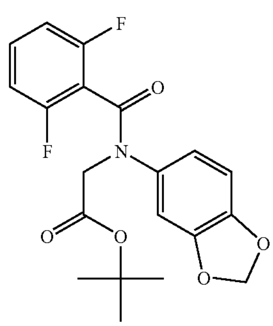 | 392.1 |

TABLE 2-continued
| Compound number | Structure | MS (m/z) (M + 1)+ |
|---|---|---|
| 109 | 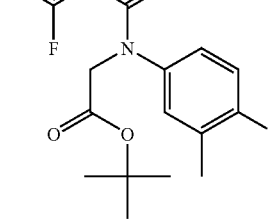 | 402.2 (M + 23)+ |
| 110 | 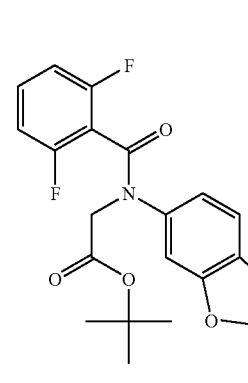 | 417.1 |
| 111 | 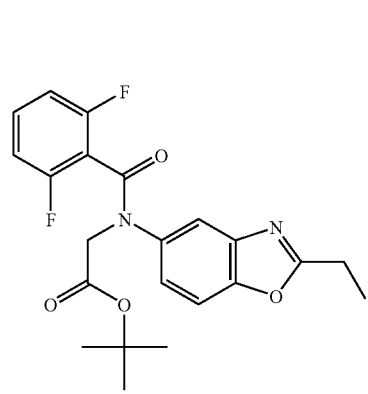 | 417.1 |
| 112 | 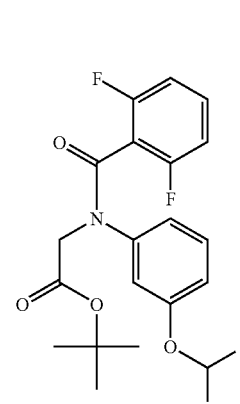 | 436.1 (M + 23)+ |

TABLE 2-continued

| Compound number | Structure | MS (m/z) (M + 1)+ |
|---|---|---|
| 113 | 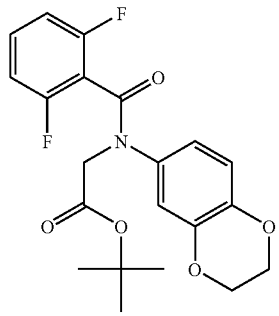 | 406.1 |
| 114 | 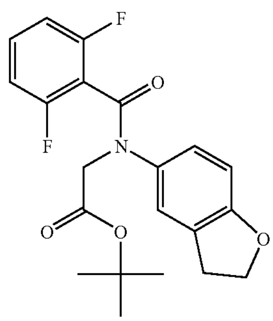 | 390.1 |
| 115 | 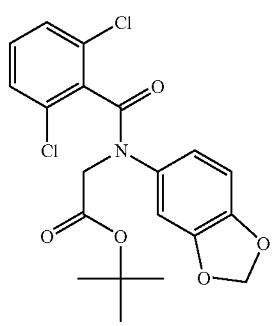 | 424.1 |
| 116 | 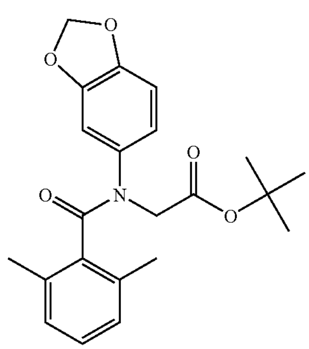 | 384.2 |

TABLE 2-continued
| Compound number | Structure | MS (m/z) (M + 1)+ |
| --- | --- | --- |
| 117 | 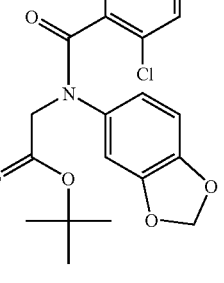 | 458.0 |
| 118 | 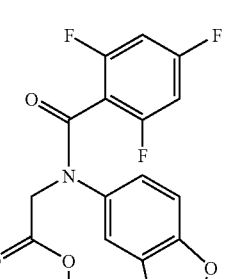 | 410.1 |
| 119 | 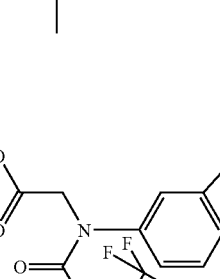 | 442.1 |
| 120 | 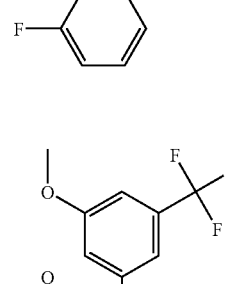 | 512.0 |

TABLE 2-continued

| Compound number | Structure | MS (m/z) (M + 1)+ |
|---|---|---|
| 121 | 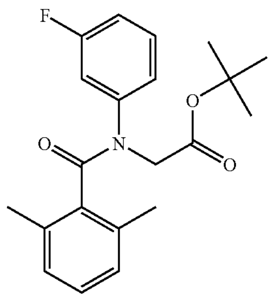 | 358.2 |
| 122 | 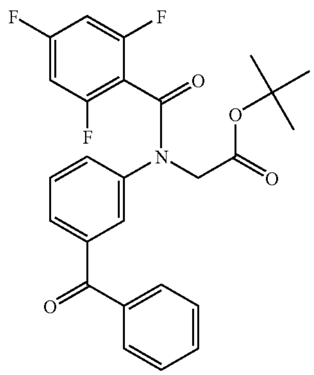 | 414.1 (M − 55)+ |
| 123 | 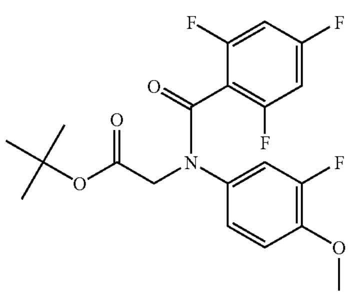 | 436.1 (M + 23)+ |
| 124 | 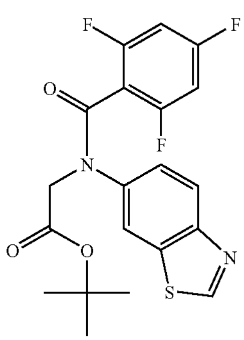 | 423.1 |
| 125 | 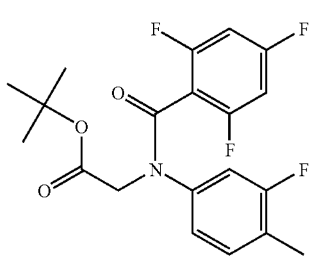 | 342.1 (M − 55)+ |

TABLE 2-continued

| Compound number | Structure | MS (m/z) (M + 1)+ |
|---|---|---|
| 126 | 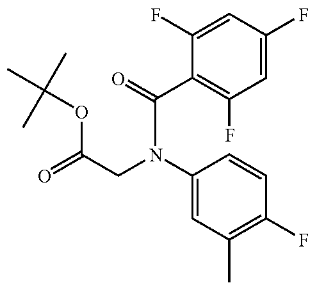 | 342.1 (M − 55)+ |
| 127 | 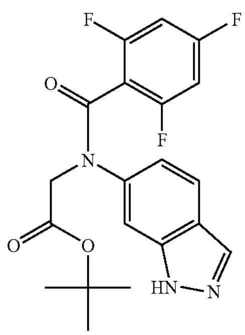 | 406.1 |
| 128 | 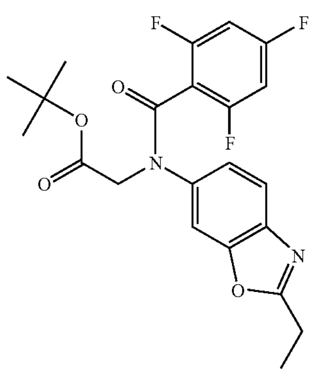 | 435.1 |
| 129 | 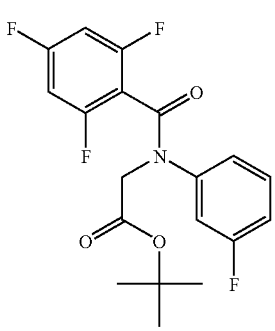 | 384.1 |

TABLE 2-continued

| Compound number | Structure | MS (m/z) (M + 1)+ |
|---|---|---|
| 130 | 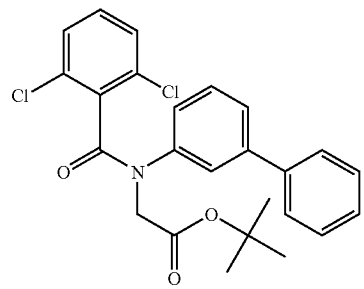 | 456.1 |
| 131 | 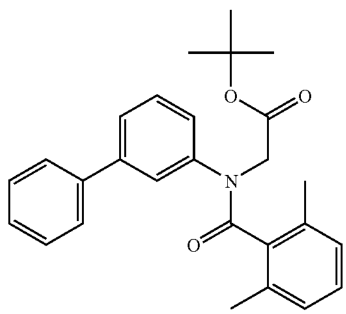 | 416.2 |
| 132 | 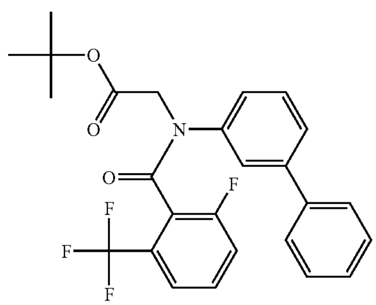 | 474.1 |
| 133 | 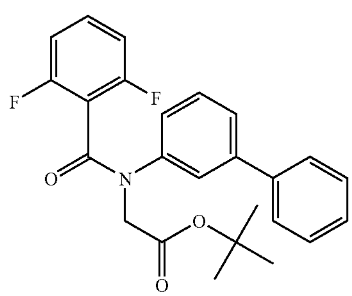 | 424.1 |
| 134 | 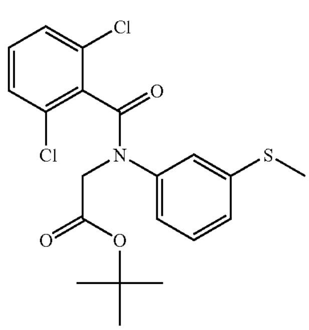 | 426.0 |

TABLE 2-continued

| Compound number | Structure | MS (m/z) (M + 1)+ |
| --- | --- | --- |
| 135 | 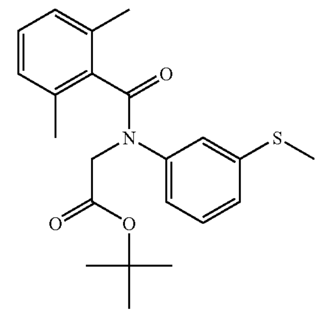 | 386.2 |
| 136 | 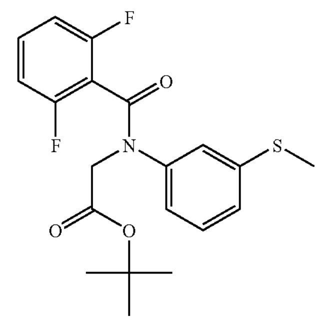 | 394.1 |
| 137 | 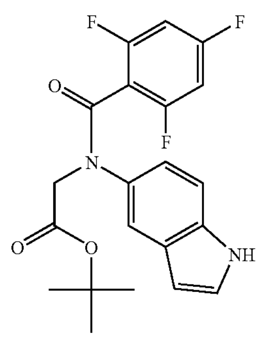 | 405.1 |
| 138 | 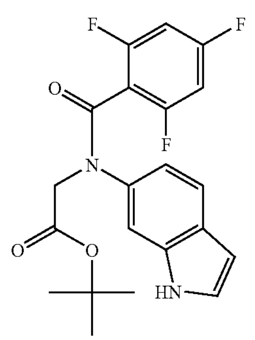 | 405.1 |

TABLE 2-continued

| Compound number | Structure | MS (m/z) (M + 1)+ |
|---|---|---|
| 139 | 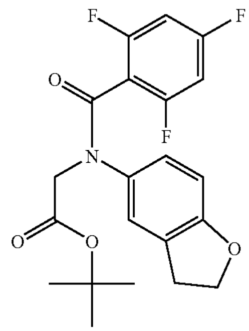 | 408.1 |
| 140 | 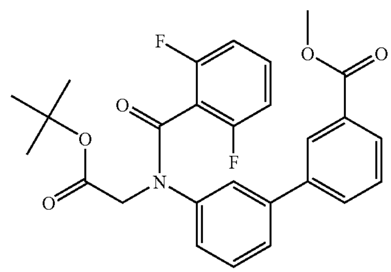 | 504.2 (M + 23)+ |
| 141 | 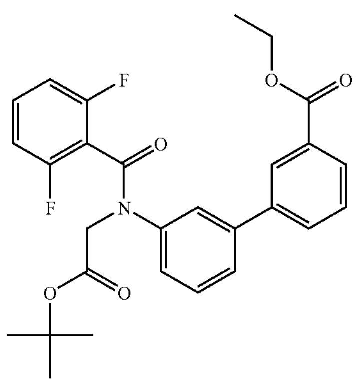 | 440.1 (M − 55)+ |
| 142 | 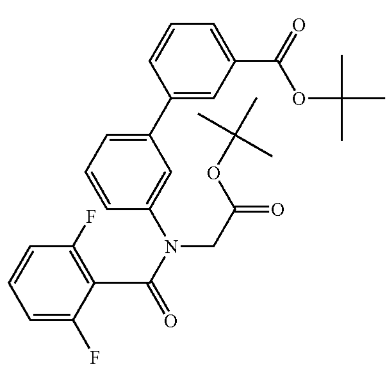 | 546.2 (M + 23)+ |
| 143 | 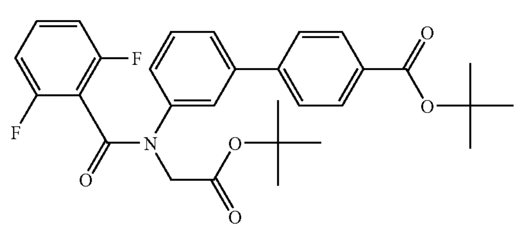 | 524.2 |

TABLE 2-continued

| Compound number | Structure | MS (m/z) (M + 1)+ |
|---|---|---|
| 144 | 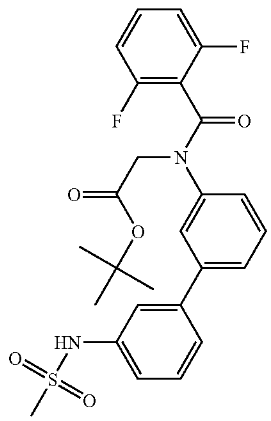 | 461.1 (M − 55)+ |
| 145 | 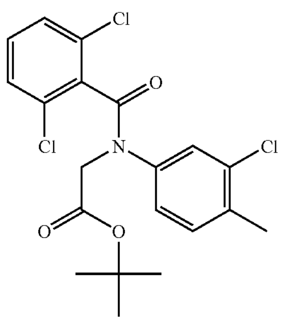 | 428.0 |
| 146 | 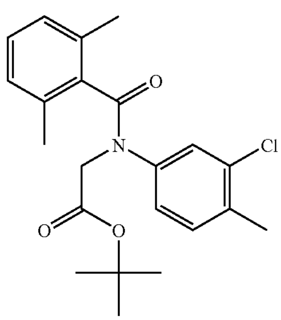 | 388.1 |
| 147 | 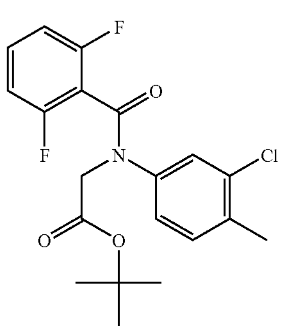 | 396.1 |

TABLE 2-continued

| Compound number | Structure | MS (m/z) (M + 1)+ |
|---|---|---|
| 148 | 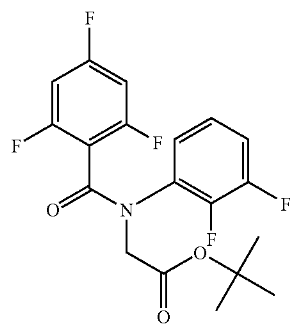 | 402.9 |
| 149 | 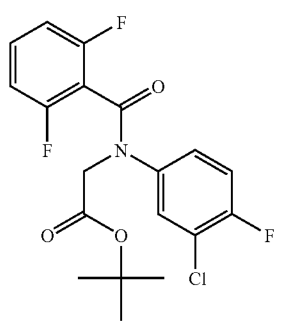 | 400.1 |
| 150 | 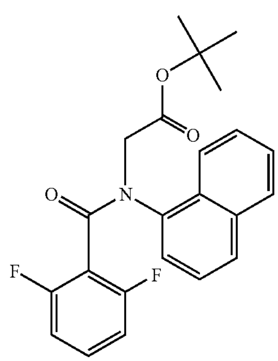 | 398.2 |
| 151 | 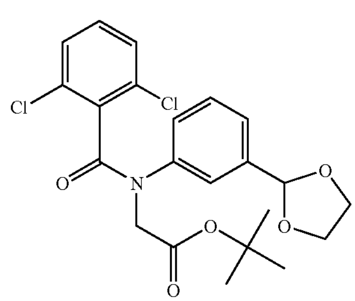 | 452.1 |

TABLE 2-continued

| Compound number | Structure | MS (m/z) (M + 1)+ |
|---|---|---|
| 152 | 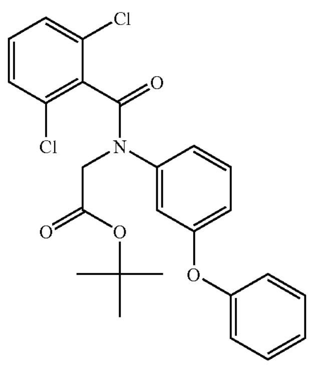 | 472.0 |
| 153 | 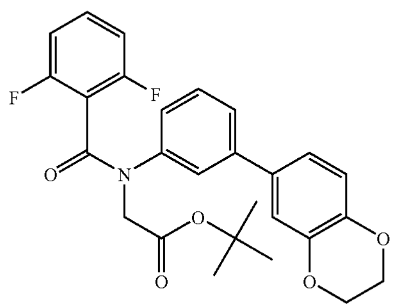 | 482.1 |
| 154 | 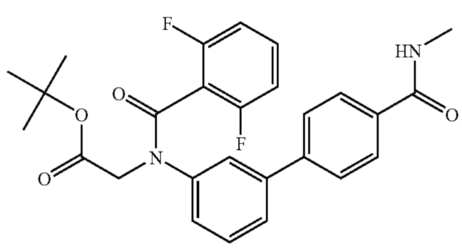 | 481.2 |
| 155 | 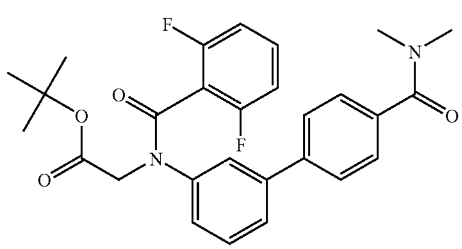 | 495.2 |
| 156 | 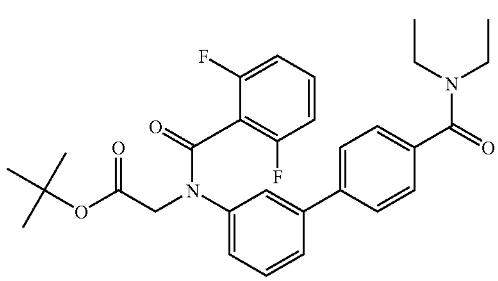 | 523.3 |

TABLE 2-continued

| Compound number | Structure | MS (m/z) (M + 1)+ |
|---|---|---|
| 157 | 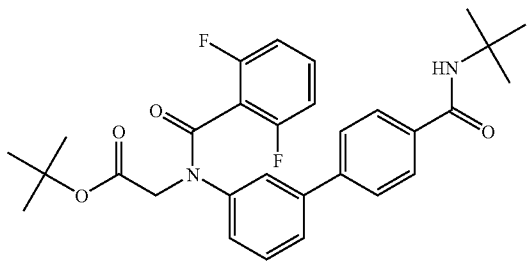 | 523.3 |
| 158 | 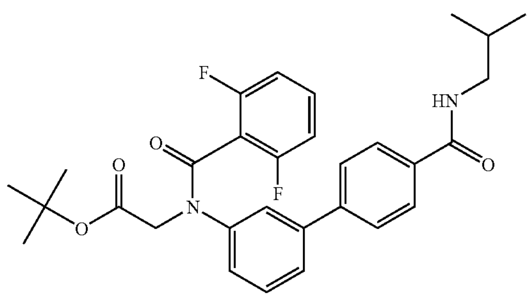 | 523.3 |
| 159 | 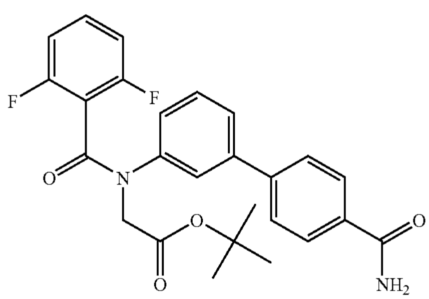 | 467.2 |
| 160 | 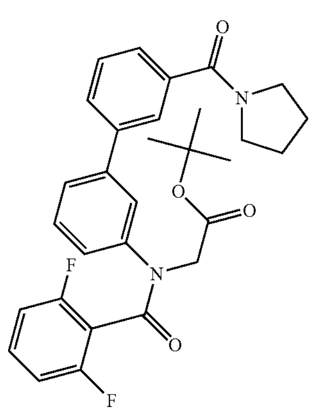 | 521.2 |

TABLE 2-continued

| Compound number | Structure | MS (m/z) (M + 1)+ |
|---|---|---|
| 161 | 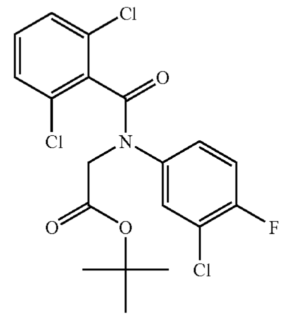 | 432.0 |
| 162 | 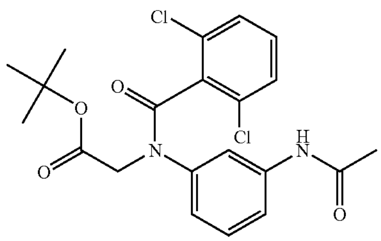 | 437.1 |
| 163 | 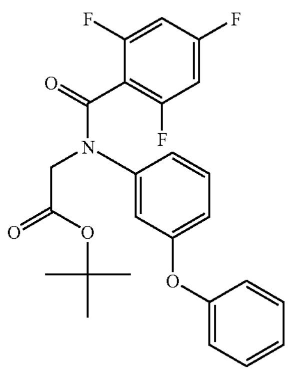 | 458.1 |
| 164 | 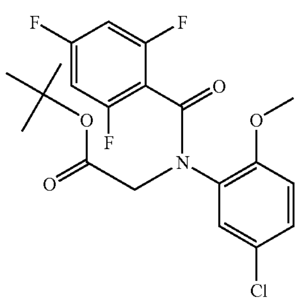 | 430.1 |
| 165 | 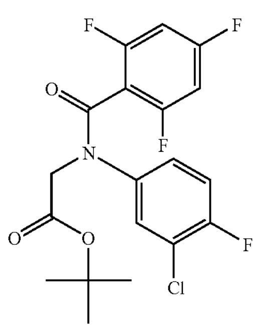 | 418.1 |

TABLE 2-continued

| Compound number | Structure | MS (m/z) (M + 1)+ |
|---|---|---|
| 166 | 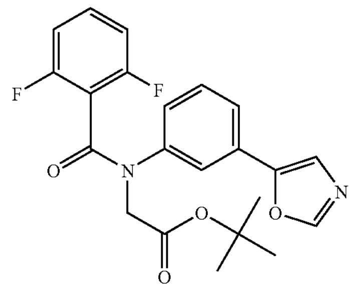 | 415.1 |
| 167 | 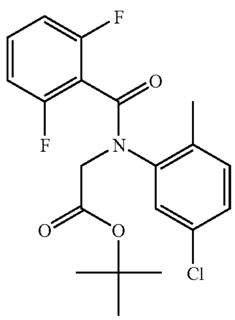 | 396.1 |
| 168 | 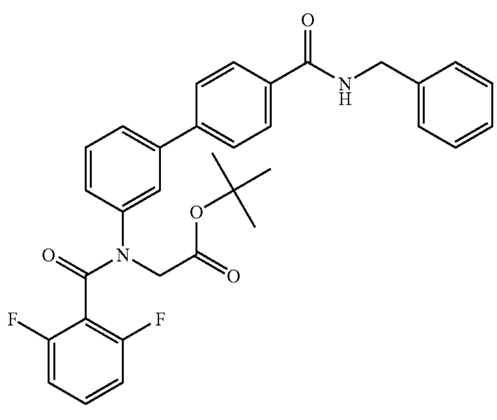 | 557.2 |
| 169 | 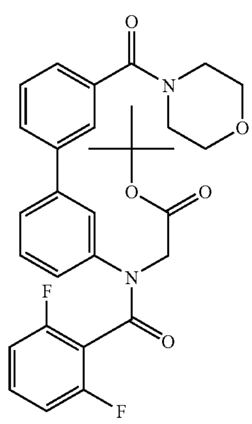 | 559.2 (M + 23)+ |

TABLE 2-continued

| Compound number | Structure | MS (m/z) (M + 1)+ |
|---|---|---|
| 170 | 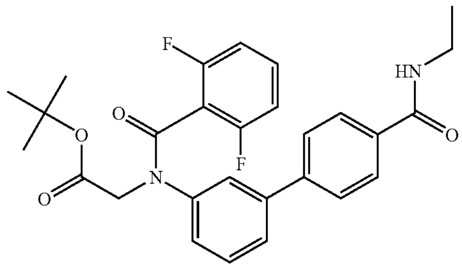 | 495.2 |
| 171 | 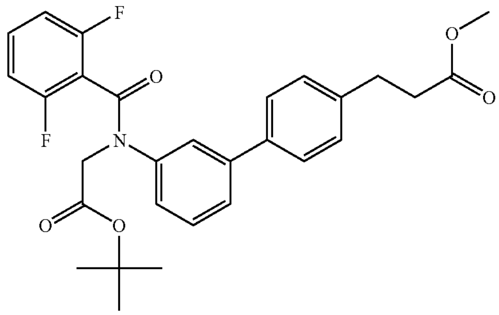 | 532.2 (M + 23)+ |
| 172 | 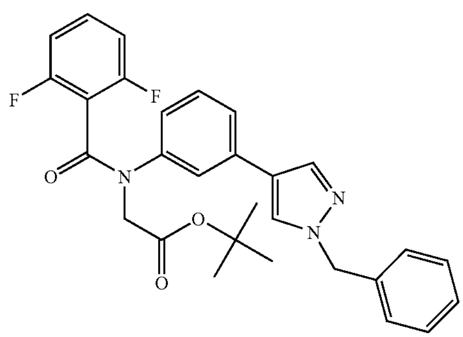 | 504.2 |
| 173 | 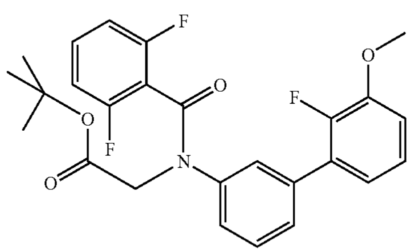 | 472.2 |
| 174 | 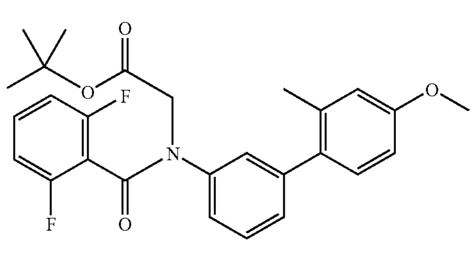 | 468.2 |

TABLE 2-continued

| Compound number | Structure | MS (m/z) (M + 1)+ |
|---|---|---|
| 175 | 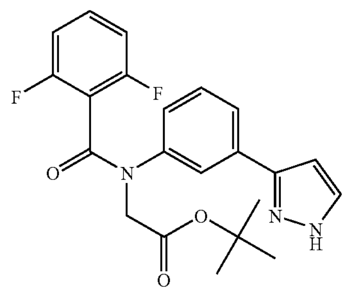 | 414.2 |
| 176 | 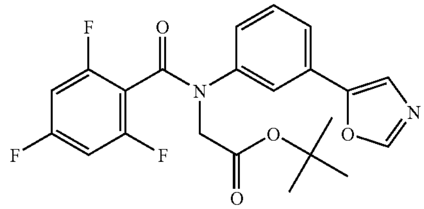 | 433.1 |
| 177 | 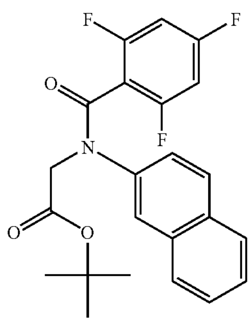 | 416.1 |
| 178 | 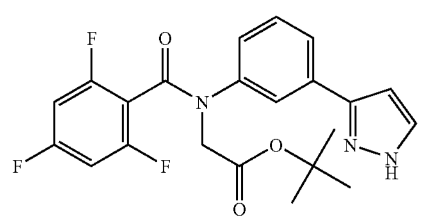 | 432.1 |
| 179 | 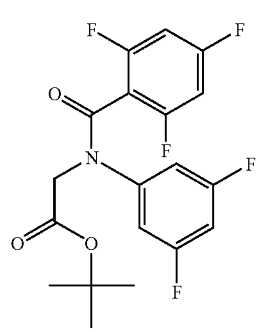 | 402.1 |

TABLE 2-continued

| Compound number | Structure | MS (m/z) (M + 1)+ |
|---|---|---|
| 180 | 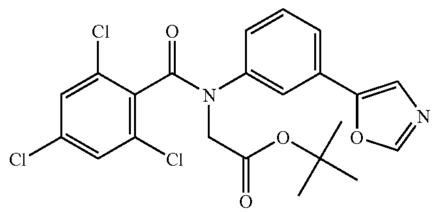 | 481.0 |
| 181 | 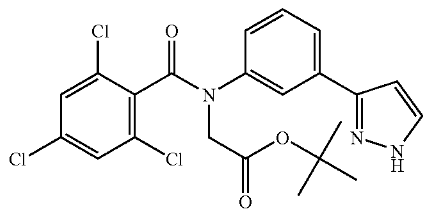 | 480.0 |
| 182 | 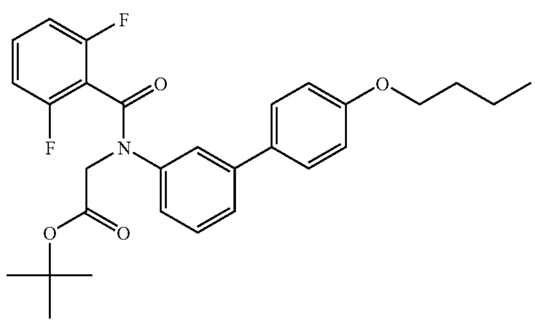 | 518.2 (M + 23)+ |
| 183 | 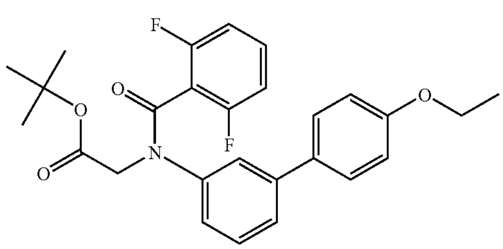 | 468.2 |
| 184 | 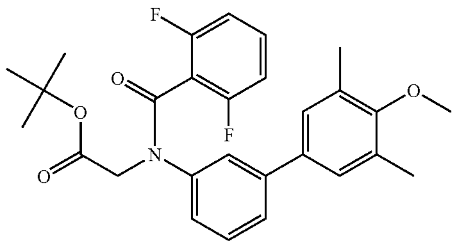 | 482.2 |

TABLE 2-continued

| Compound number | Structure | MS (m/z) (M + 1)+ |
|---|---|---|
| 185 | 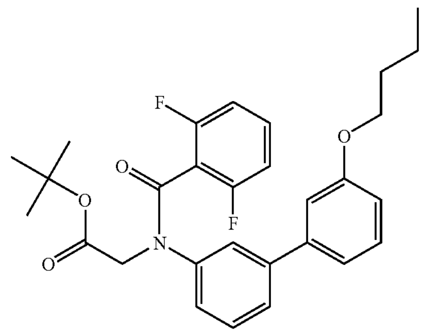 | 518.2 (M + 23)+ |
| 186 | 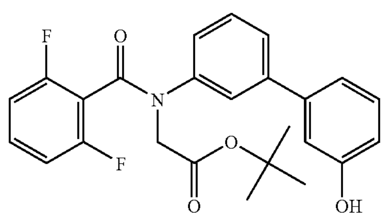 | 440.2 |
| 187 | 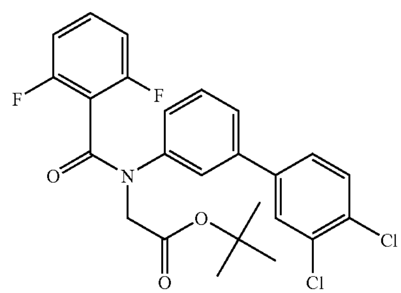 | 492.1 |
| 188 | 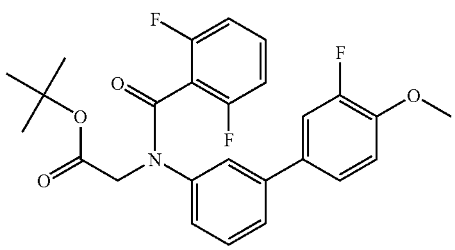 | 416.1 (M − 55)+ |
| 189 | 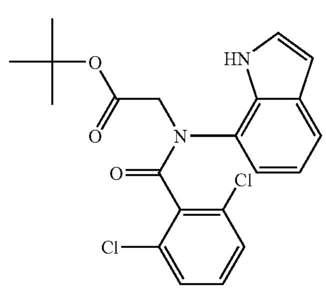 | 419.1 |

TABLE 2-continued

| Compound number | Structure | MS (m/z) (M + 1)+ |
|---|---|---|
| 190 | 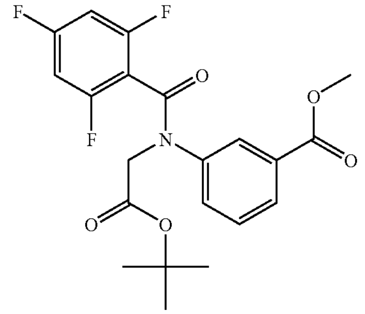 | 424.1 |
| 191 | 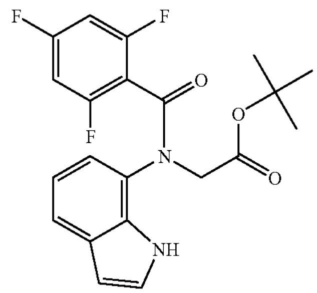 | 405.1 |
| 192 | 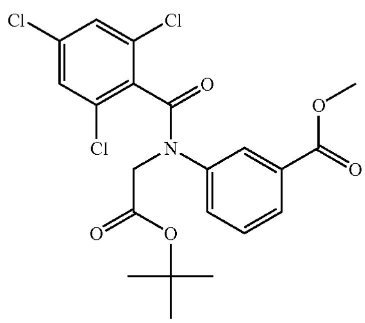 | 472.0 |
| 193 | 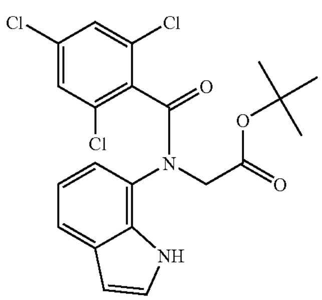 | 453.0 |
| 194 | 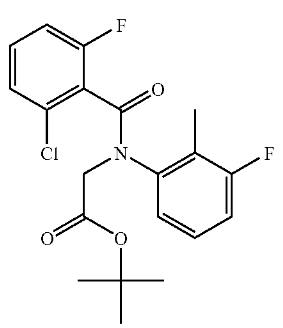 | 396.1 |

TABLE 2-continued

| Compound number | Structure | MS (m/z) (M + 1)+ |
|---|---|---|
| 195 | 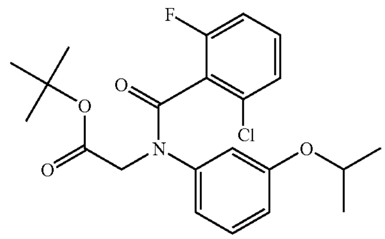 | 422.1 |
| 196 | 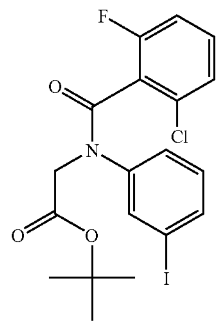 | 490.0 |
| 197 | 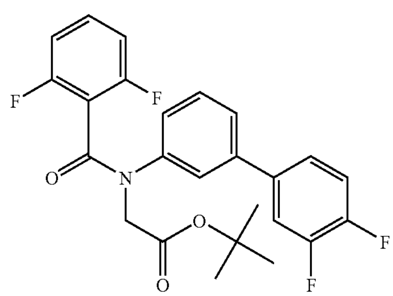 | 482.2 (M + 23)+ |
| 198 | 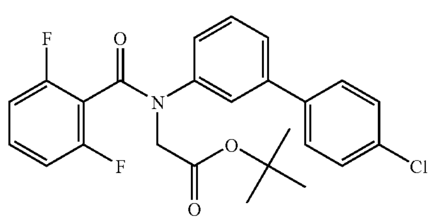 | 480.1 (M + 23)+ |
| 199 | 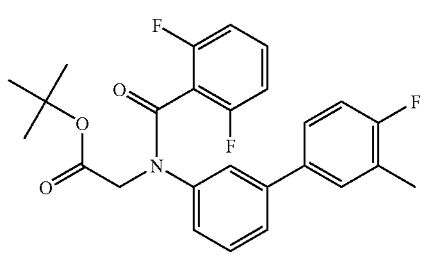 | 456.2 |

TABLE 2-continued

| Compound number | Structure | MS (m/z) (M + 1)+ |
| --- | --- | --- |
| 200 | 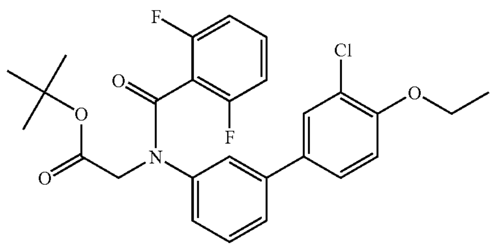 | 524.2 (M + 23)+ |
| 201 | 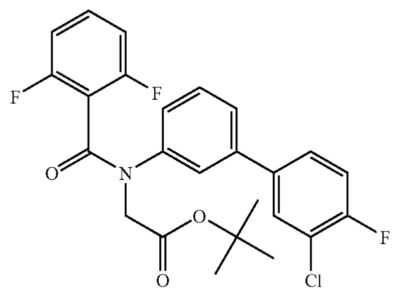 | 498.2 (M + 23)+ |
| 202 | 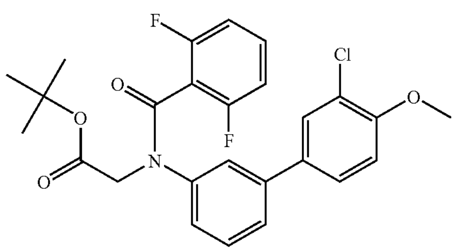 | 510.1 (M + 23)+ |
| 203 | 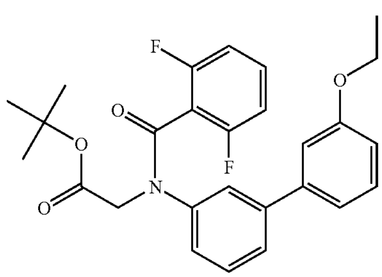 | 468.2 |
| 204 | 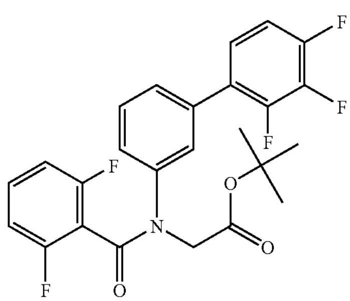 | 500.1 (M + 23)+ |

TABLE 2-continued

| Compound number | Structure | MS (m/z) (M + 1)+ |
|---|---|---|
| 205 | 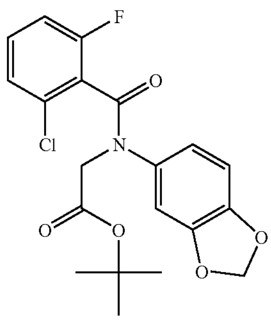 | 408.1 |
| 206 | 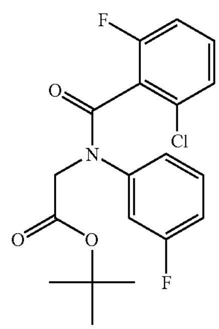 | 382.1 |
| 207 | 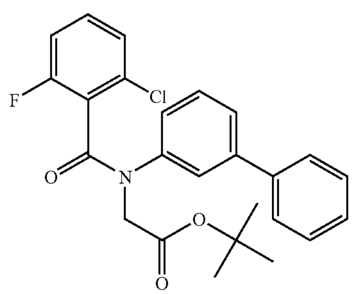 | 440.1 |
| 208 | 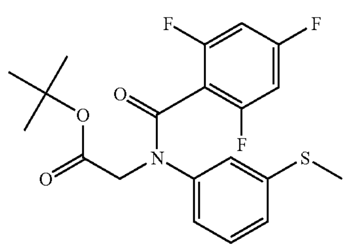 | 412.1 |
| 209 | 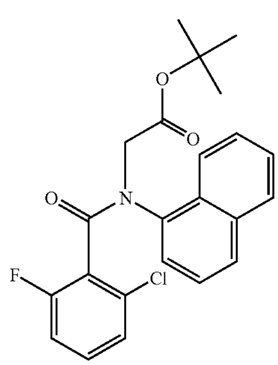 | 414.1 |

TABLE 2-continued

| Compound number | Structure | MS (m/z) (M + 1)+ |
|---|---|---|
| 210 | 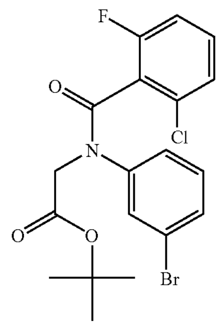 | 442.0 |
| 211 | 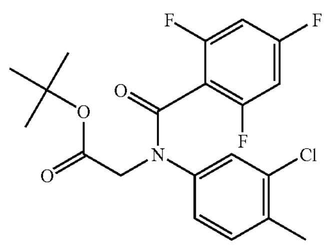 | 414.1 |
| 212 | 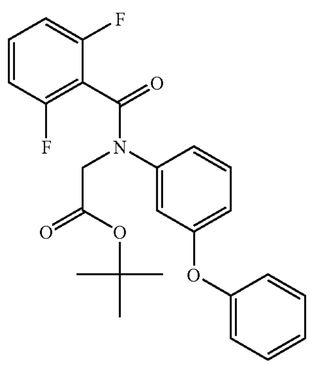 | 440.1 |
| 213 | 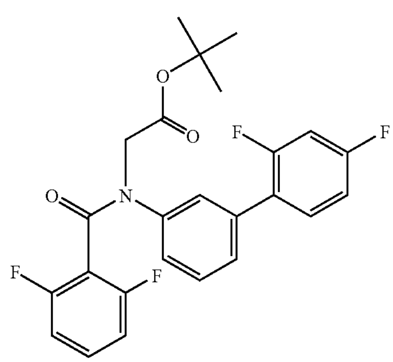 | 460.2 |

TABLE 2-continued

| Compound number | Structure | MS (m/z) (M + 1)+ |
|---|---|---|
| 214 | 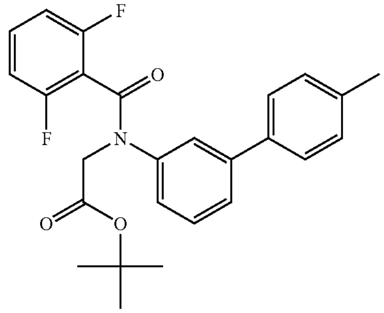 | 437.9 |
| 215 | 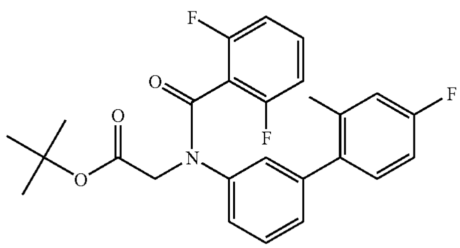 | 478.2 (M + 23)+ |
| 216 | 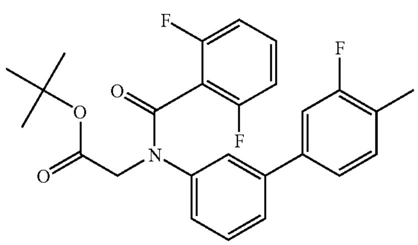 | 478.2 (M + 23)+ |
| 217 | 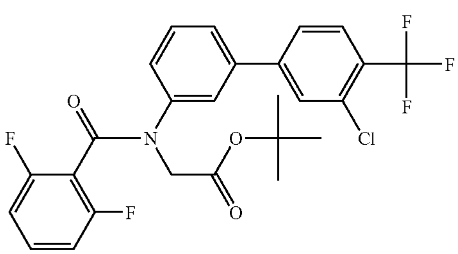 | 470.1 (M − 55)+ |
| 218 | 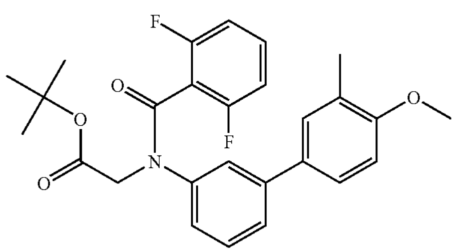 | 490.2 (M + 23)+ |

TABLE 2-continued

| Compound number | Structure | MS (m/z) (M + 1)+ |
|---|---|---|
| 219 | 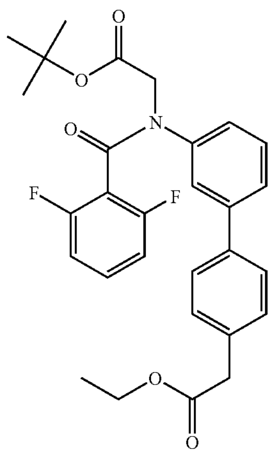 | 510.2 |
| 220 | 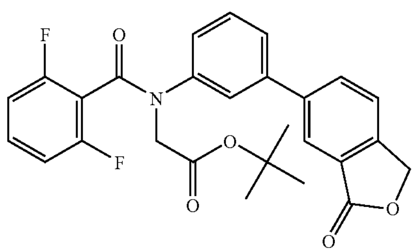 | 424.3 (M − 55)+ |
| 221 | 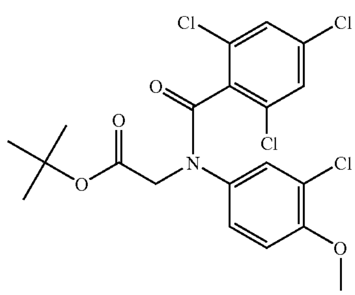 | 478.0 |
| 222 | 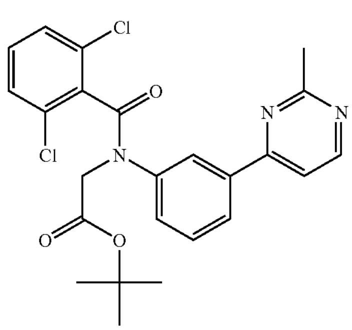 | 472.1 |

TABLE 2-continued

| Compound number | Structure | MS (m/z) (M + 1)+ |
|---|---|---|
| 223 | 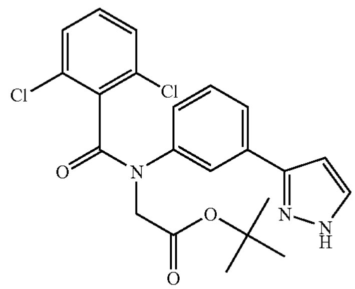 | 446.1 |
| 224 | 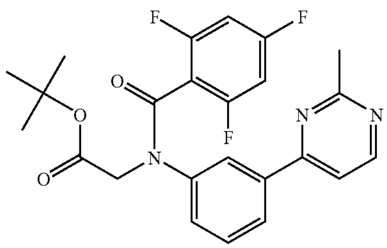 | 458.1 |
| 225 | 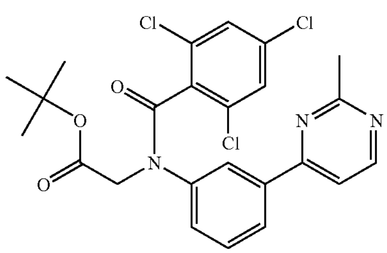 | 506.1 |
| 226 | 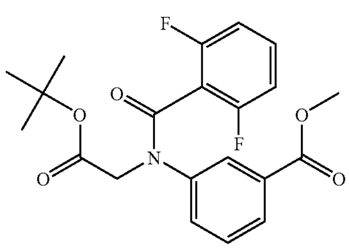 | 406.2 |
| 227 | 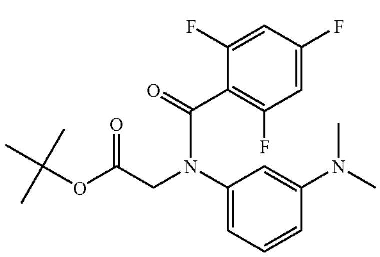 | 409.2 |

TABLE 2-continued

| Compound number | Structure | MS (m/z) (M + 1)+ |
|---|---|---|
| 228 | 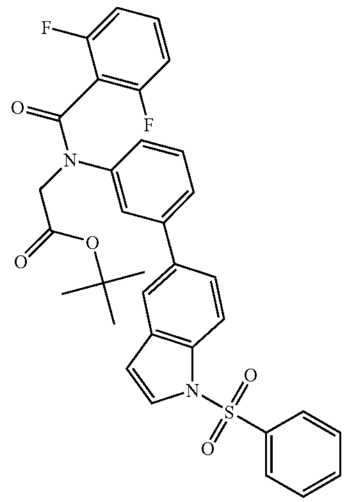 | 603.2 |
| 229 | 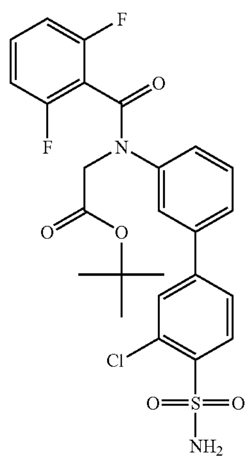 | 481.2 (M − 55)+ |
| 230 | 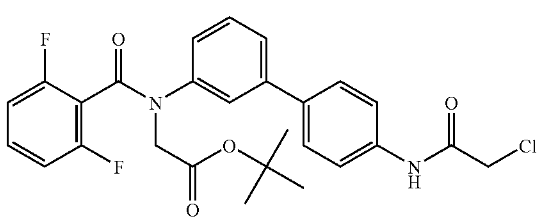 | 515.2 |
| 231 | 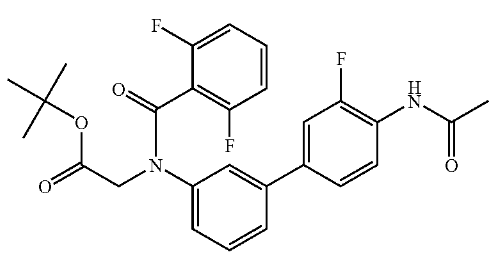 | 443.3 (M − 55)+ |

TABLE 2-continued

| Compound number | Structure | MS (m/z) (M + 1)+ |
|---|---|---|
| 232 | 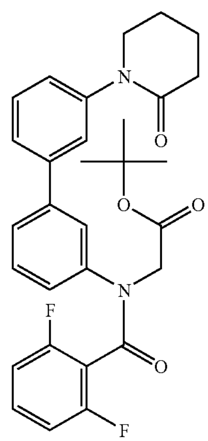 | 521.0 |
| 233 | 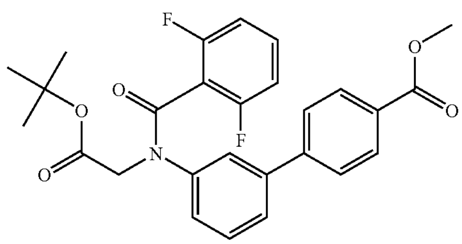 | 482.2 |
| 234 | 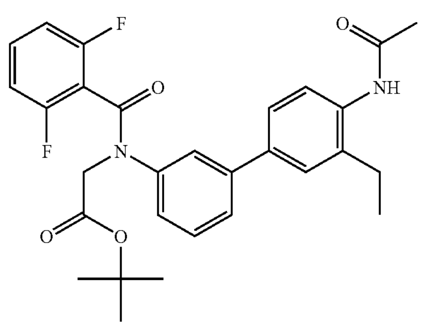 | 453.3 (M − 55)+ |
| 235 | 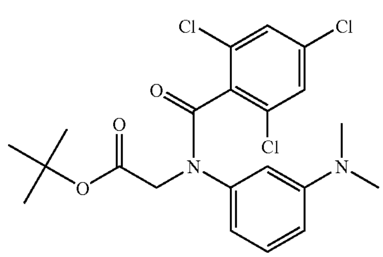 | 457.1 |

TABLE 2-continued

| Compound number | Structure | MS (m/z) (M + 1)+ |
|---|---|---|
| 236 | 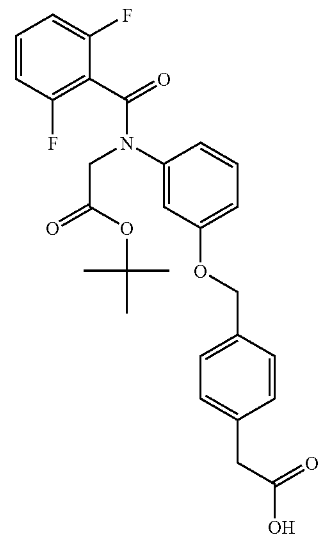 | 512.1 |
| 237 | 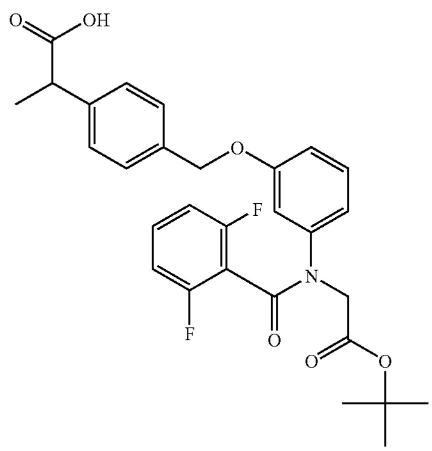 | 526.2 |
| 238 | 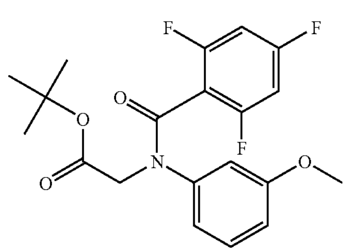 | 396.1 |
| 239 | 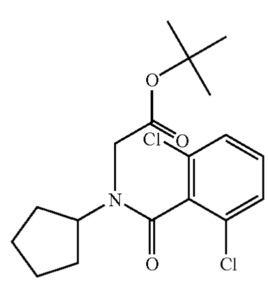 | 372.1 |

TABLE 2-continued

| Compound number | Structure | MS (m/z) (M + 1)+ |
|---|---|---|
| 240 | 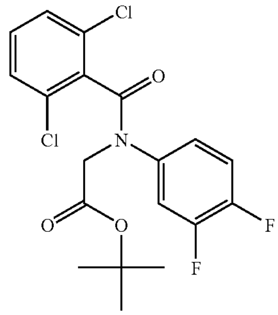 | 416.0 |
| 241 | 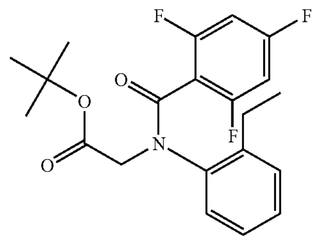 | 416.1 (M + 23)+ |
| 242 | 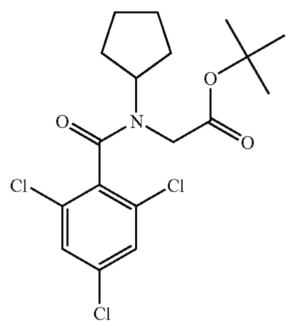 | 406.0 |
| 243 | 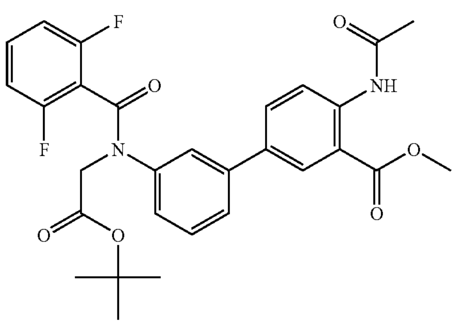 | 539.1 |
| 244 | 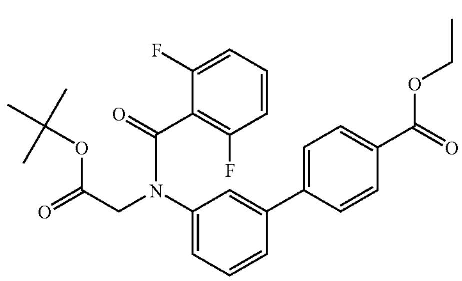 | 496.2 |

TABLE 2-continued

| Compound number | Structure | MS (m/z) (M + 1)+ |
|---|---|---|
| 245 | 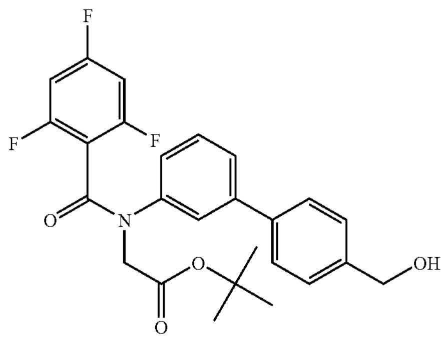 | 494.2 (M + 23)+ |
| 246 | 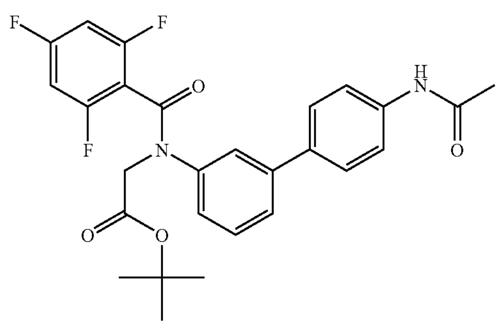 | 443.1 (M − 55)+ |
| 247 | 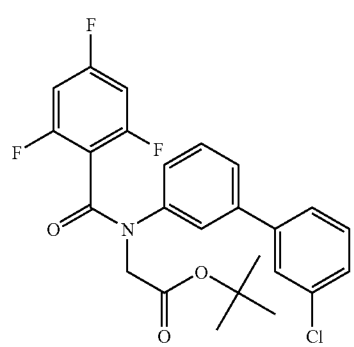 | 498.1 (M + 23)+ |
| 248 | 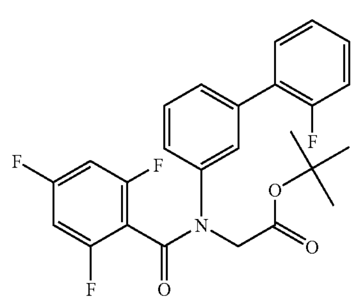 | 482.1 (M + 23)+ |

TABLE 2-continued

| Compound number | Structure | MS (m/z) (M + 1)+ |
|---|---|---|
| 249 | 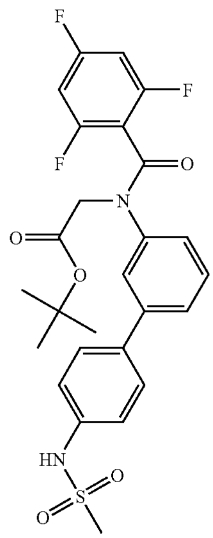 | 479.0 (M − 55)+ |
| 250 | 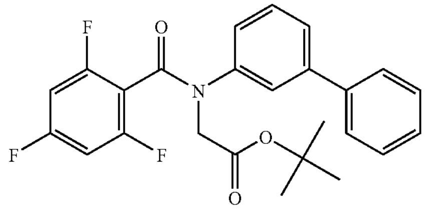 | 464.1 (M + 23)+ |
| 251 | 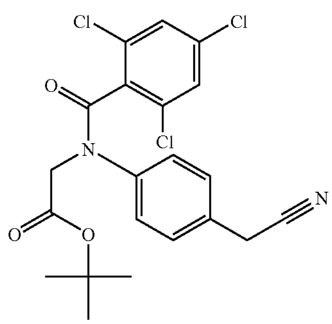 | 453.0 |
| 252 | 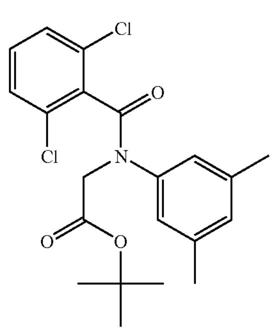 | 408.0 |

TABLE 2-continued

| Compound number | Structure | MS (m/z) (M + 1)+ |
|---|---|---|
| 253 | 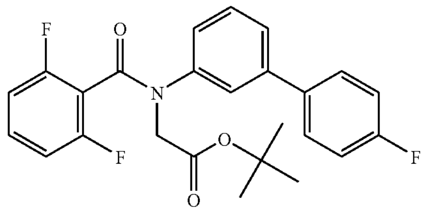 | 442.1 |
| 254 | 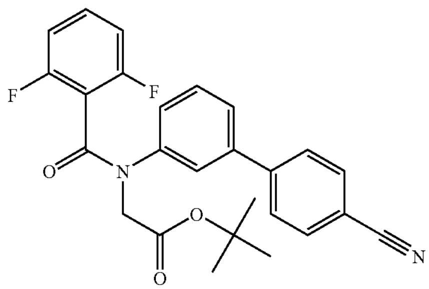 | 449.1 |
| 255 | 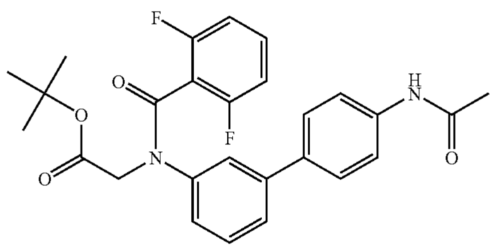 | 425.0 (M − 56)+ |
| 256 | 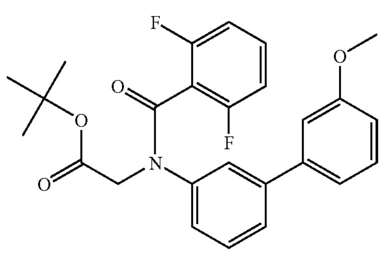 | 476.1 (M + 23)+ |
| 257 | 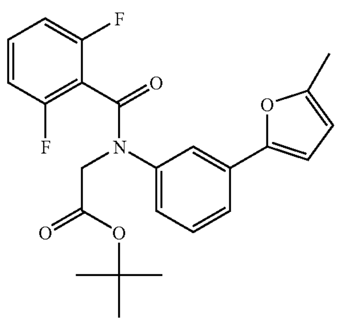 | 428.0 |

TABLE 2-continued

| Compound number | Structure | MS (m/z) (M + 1)+ |
|---|---|---|
| 258 | 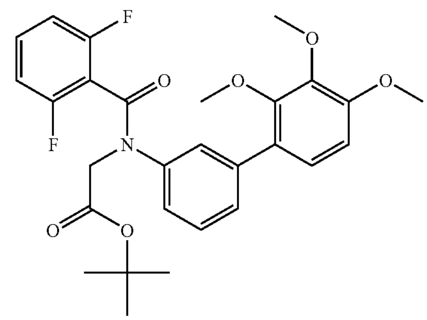 | 514.2 |
| 259 | 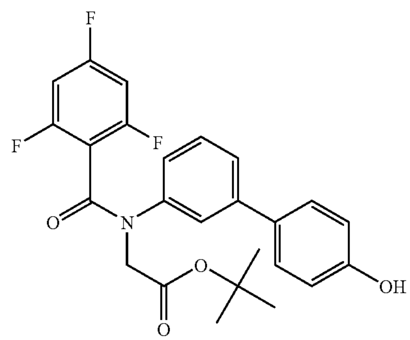 | 402.1 (M − 55)+ |
| 260 | 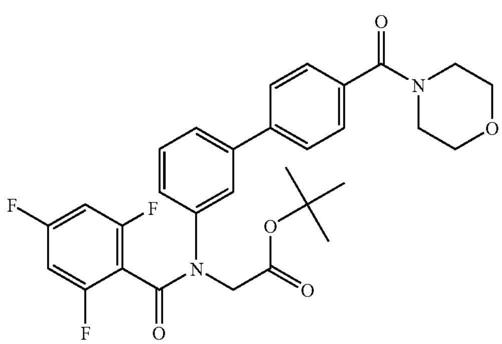 | 555.2 |
| 261 | 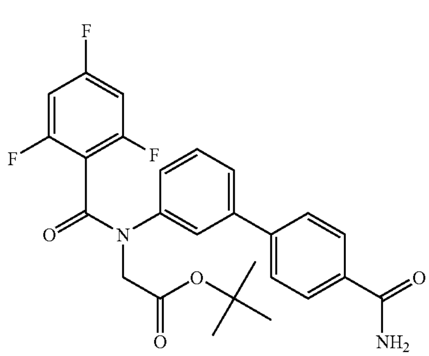 | 485.1 |

TABLE 2-continued
| Compound number | Structure | MS (m/z) (M + 1)+ |
|---|---|---|
| 262 | 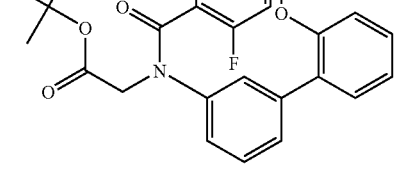 | 494.1 (M + 23)+ |
| 263 | 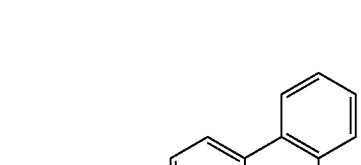 | 498.1 (M + 23)+ |
| 264 | 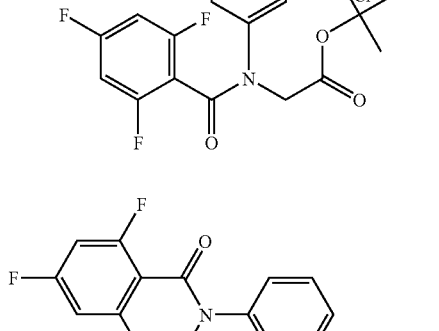 | 525.2 |
| 265 | 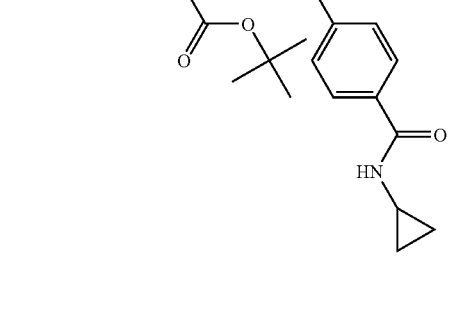 | 497.1 (M − 55)+ |

TABLE 2-continued

| Compound number | Structure | MS (m/z) (M + 1)+ |
|---|---|---|
| 266 | 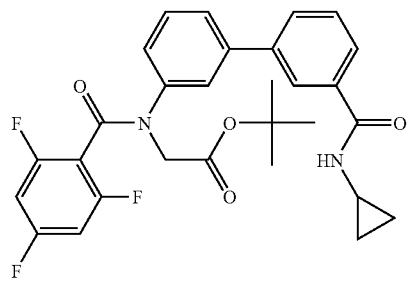 | 469.1 (M − 55)+ |
| 267 | 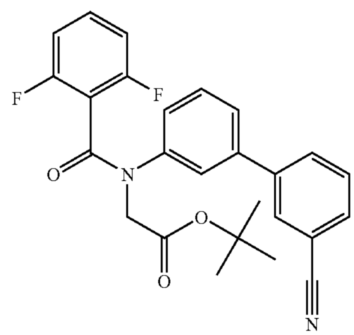 | 449.1 |
| 268 | 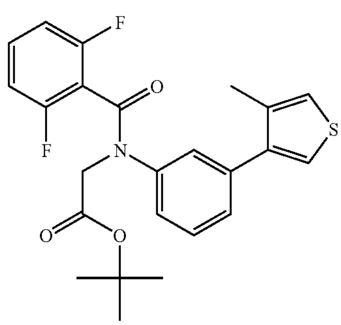 | 444.1 |
| 269 | 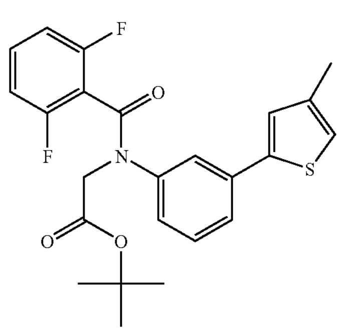 | 444.1 |

TABLE 2-continued

| Compound number | Structure | MS (m/z) (M + 1)+ |
|---|---|---|
| 270 | 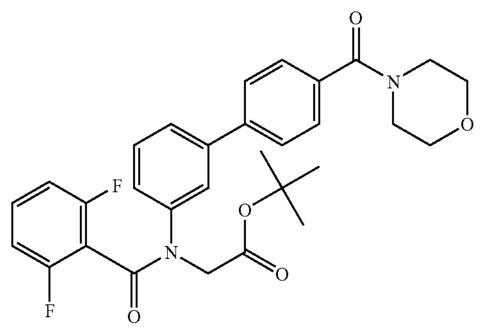 | 537.2 |
| 271 | 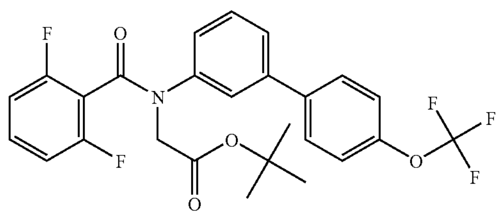 | 508.1 |
| 272 | 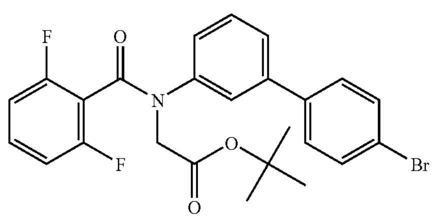 | 502.0 |
| 273 | 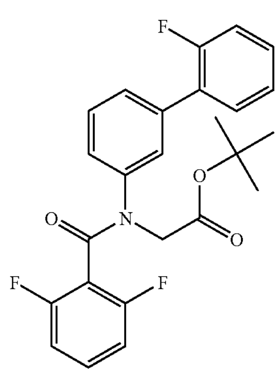 | 442.1 |
| 274 | 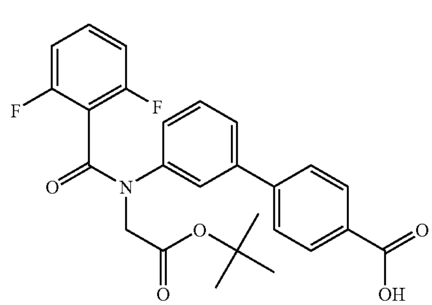 | 490.1 (M + 23)+ |

TABLE 2-continued

| Compound number | Structure | MS (m/z) (M + 1)+ |
|---|---|---|
| 275 | 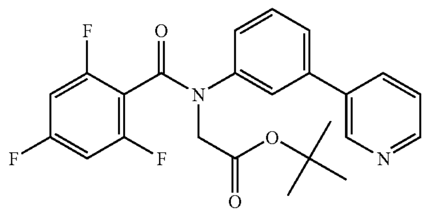 | 443.1 |
| 276 | 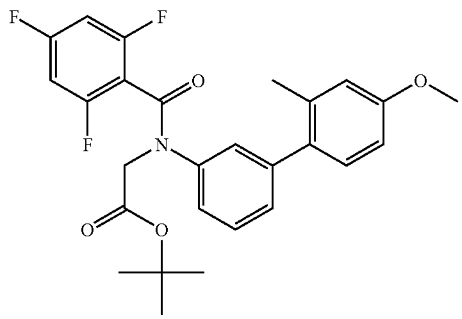 | 508.1 (M + 23)+ |
| 277 | 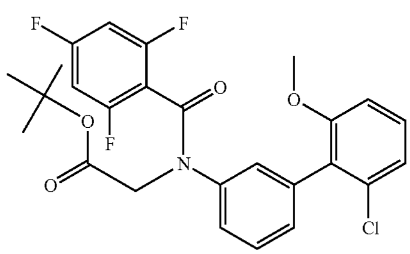 | 450.0 (M − 55)+ |
| 278 | 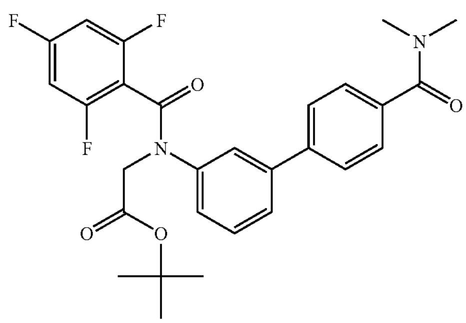 | 513.2 |
| 279 | 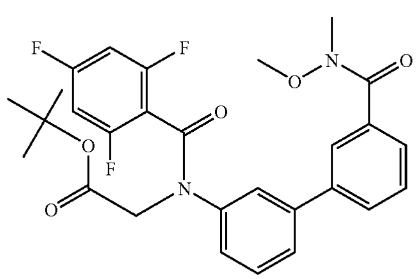 | 473.1 (M − 55)+ |

TABLE 2-continued

| Compound number | Structure | MS (m/z) (M + 1)+ |
|---|---|---|
| 280 | 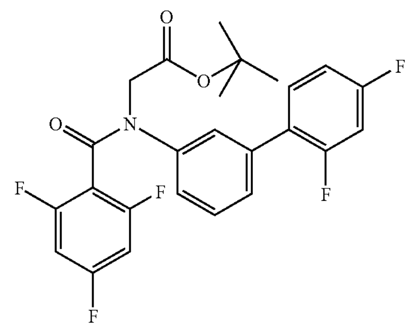 | 500.1 (M + 23)+ |
| 281 | 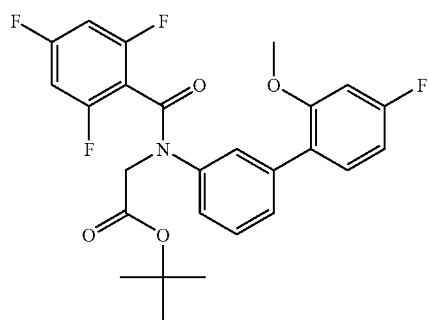 | 512.2 (M + 23)+ |
| 282 | 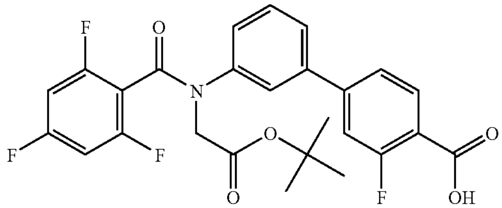 | 526.1 (M + 23)+ |
| 283 | 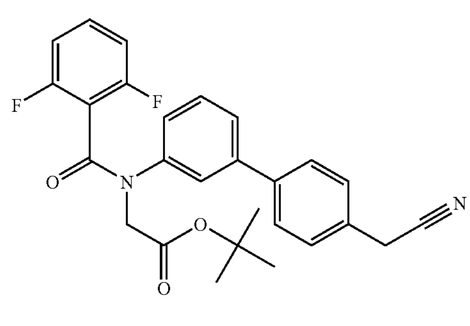 | 485.1 (M + 23)+ |

TABLE 2-continued

| Compound number | Structure | MS (m/z) (M + 1)+ |
|---|---|---|
| 284 | 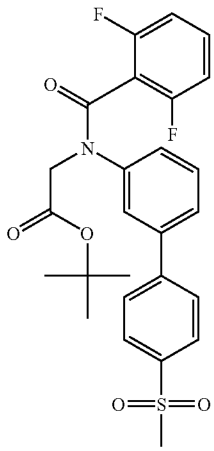 | 502.1 |
| 285 | 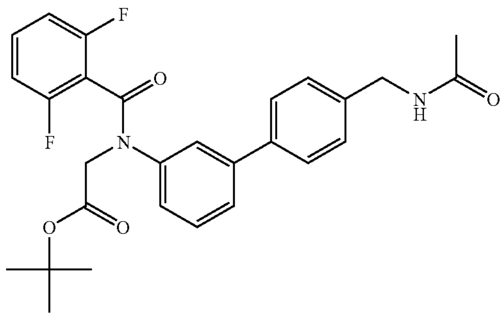 | 495.2 |
| 286 | 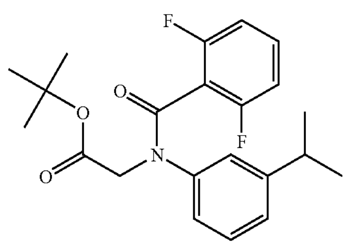 | 390.1 |
| 287 | 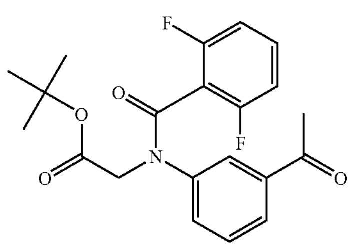 | 390.1 |
| 288 | 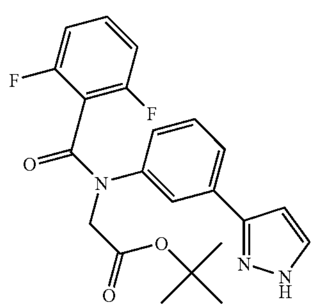 | 414.1 |

TABLE 2-continued

| Compound number | Structure | MS (m/z) (M + 1)+ |
|---|---|---|
| 289 | 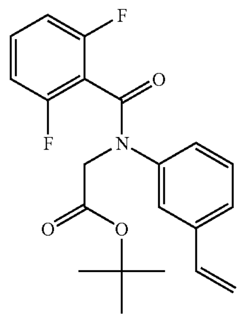 | 374.1 |
| 290 | 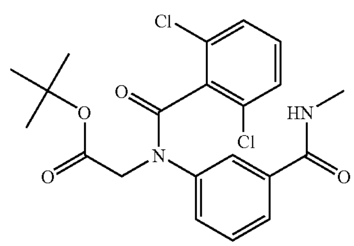 | 437.7 |
| 291 | 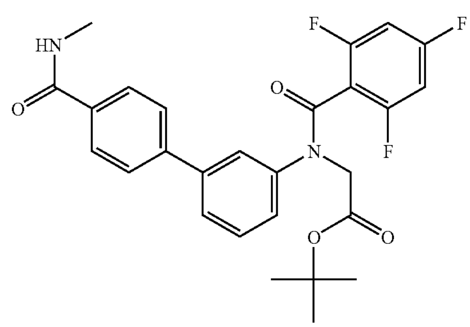 | 499.2 |
| 292 | 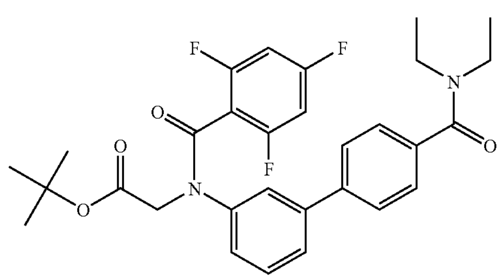 | 541.2 |
| 293 | 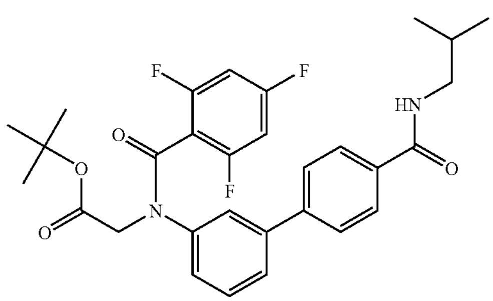 | 541.2 |

TABLE 2-continued

| Compound number | Structure | MS (m/z) (M + 1)+ |
|---|---|---|
| 294 | 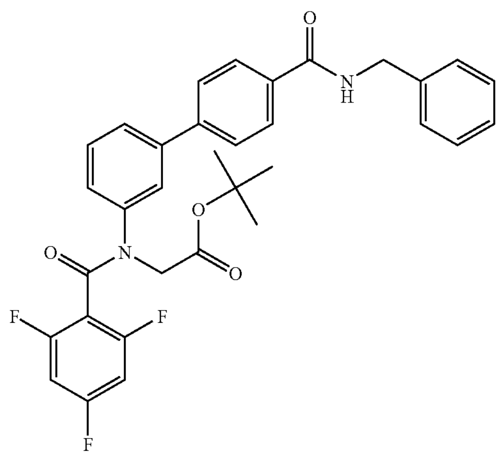 | 575.2 |
| 295 | 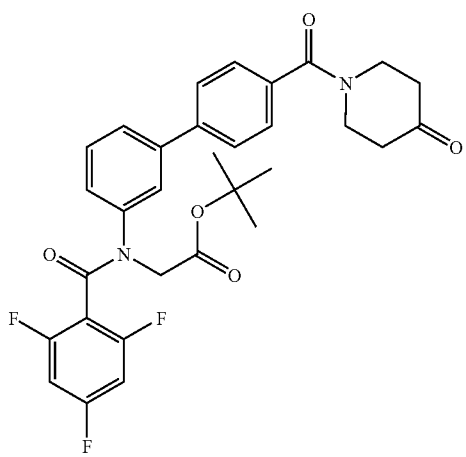 | 567.2 |
| 296 | 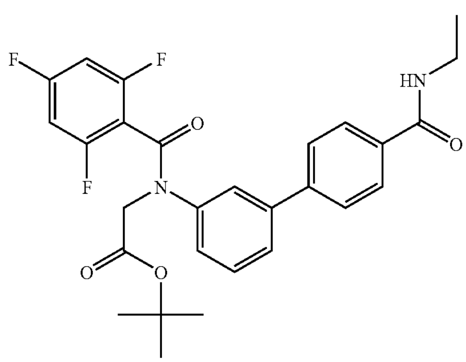 | 513.2 |
| 297 | 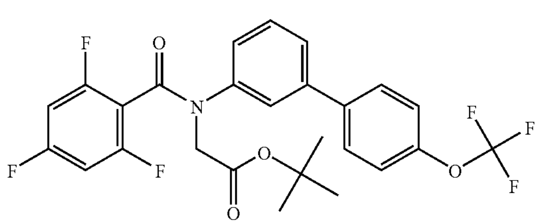 | 548.1 (M + 23)+ |

TABLE 2-continued

| Compound number | Structure | MS (m/z) (M + 1)+ |
| --- | --- | --- |
| 298 | 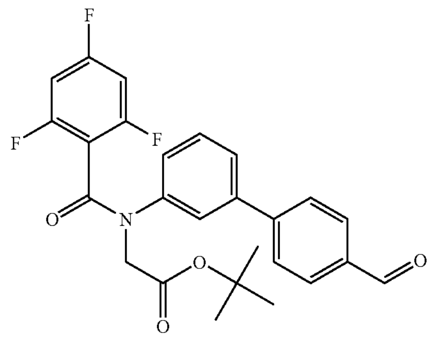 | 492.1 (M + 23)+ |
| 299 | 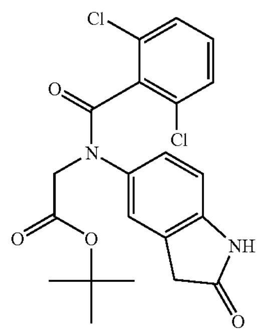 | 435.1 |
| 300 | 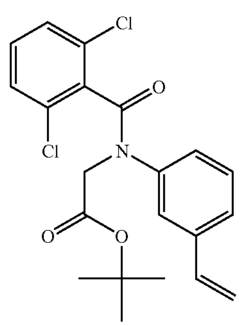 | 406.0 |
| 301 | 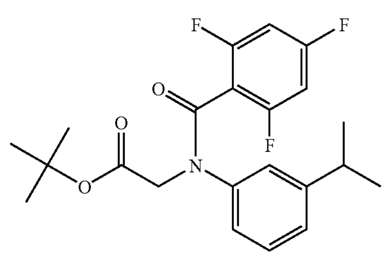 | 408.1 |
| 302 | 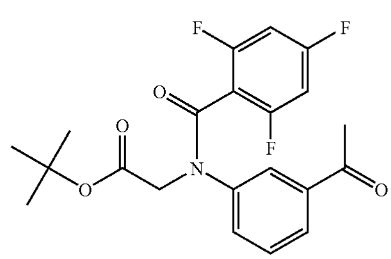 | 352.1 (M − 56)+ |

TABLE 2-continued

| Compound number | Structure | MS (m/z) (M + 1)+ |
|---|---|---|
| 303 | 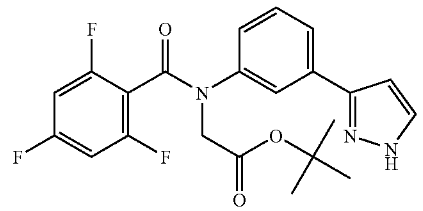 | 432.1 |
| 304 | 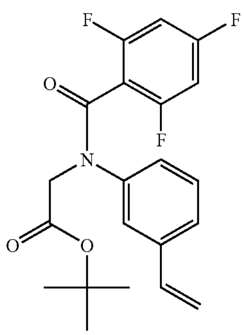 | 392.1 |
| 305 | 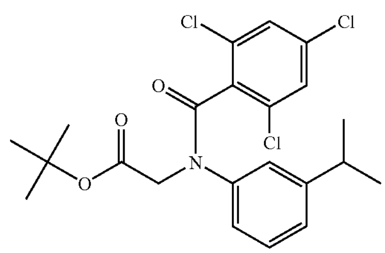 | 456.0 |
| 306 | 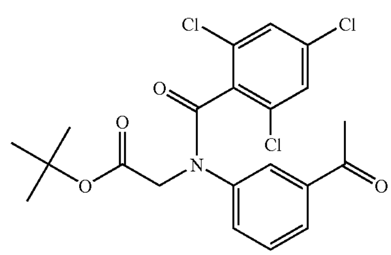 | 456.0 |
| 307 | 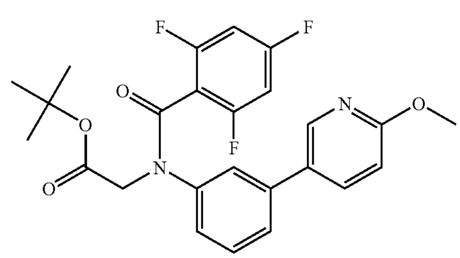 | 473.2 |
| 308 | 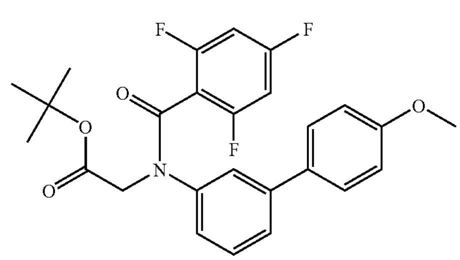 | 494.1 (M + 23)+ |

TABLE 2-continued

| Compound number | Structure | MS (m/z) (M + 1)+ |
|---|---|---|
| 309 | 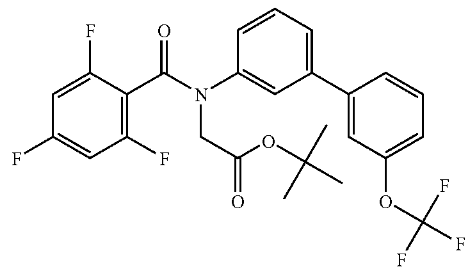 | 548.1 (M + 23)+ |
| 310 | 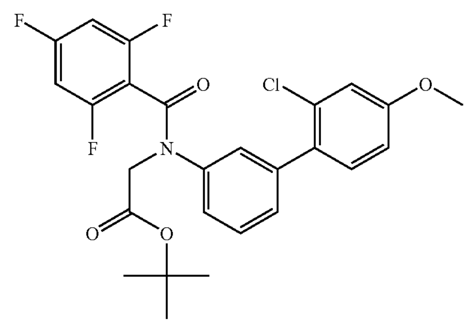 | 528.1 (M + 23)+ |
| 311 | 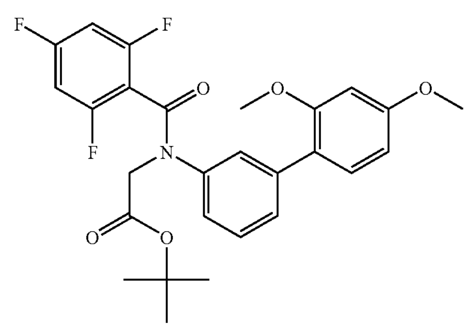 | 446.1 (M − 55)+ |
| 312 | 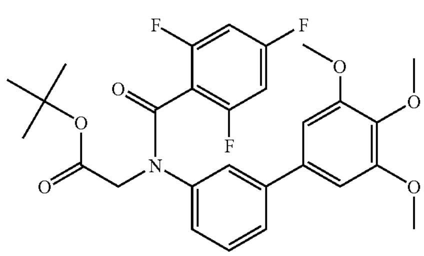 | 476.1 (M − 55)+ |
| 313 | 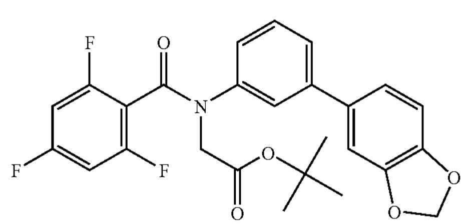 | 508.1 (M + 23)+ |

TABLE 2-continued

| Compound number | Structure | MS (m/z) (M + 1)+ |
|---|---|---|
| 314 | 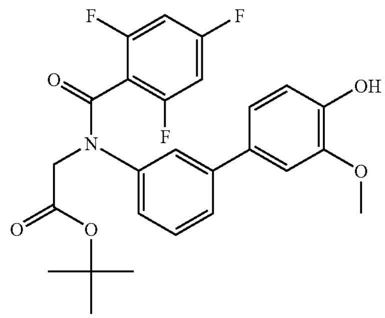 | 432.0 (M − 55)+ |
| 315 | 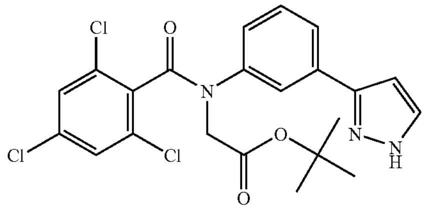 | 480.0 |
| 316 | 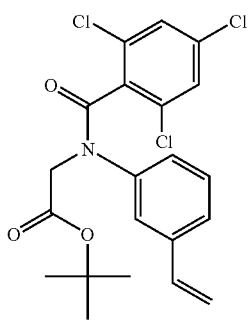 | 440.0 |
| 317 | 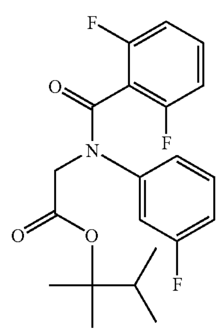 | 416.1 (M + 23)+ |
| 318 | 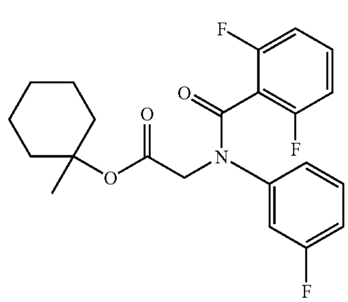 | 428.1 (M + 23)+ |

TABLE 2-continued

| Compound number | Structure | MS (m/z) (M + 1)+ |
|---|---|---|
| 319 | 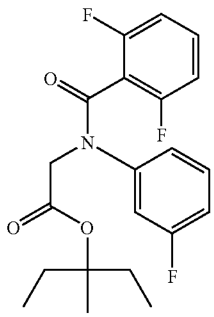 | 416.1 (M + 23)+ |
| 320 | 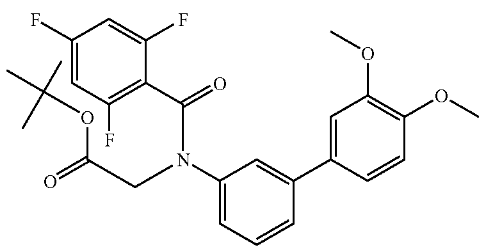 | 446.1 (M − 55)+ |
| 321 | 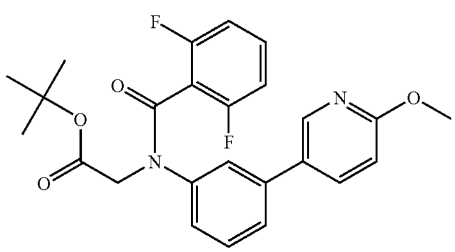 | 455.1 |
| 322 | 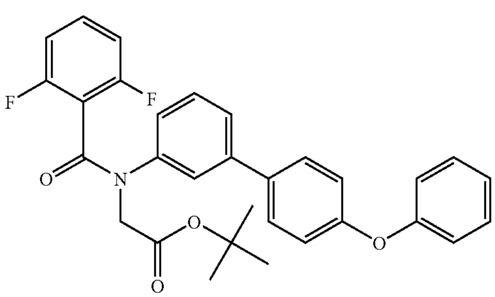 | 460.1 (M − 55)+ |
| 323 | 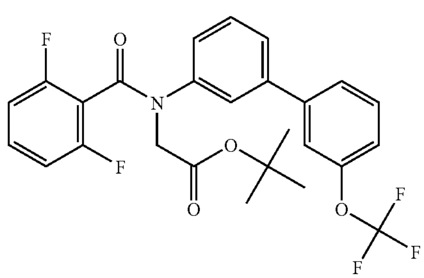 | 530.1 (M + 23)+ |

TABLE 2-continued

| Compound number | Structure | MS (m/z) (M + 1)+ |
|---|---|---|
| 324 | 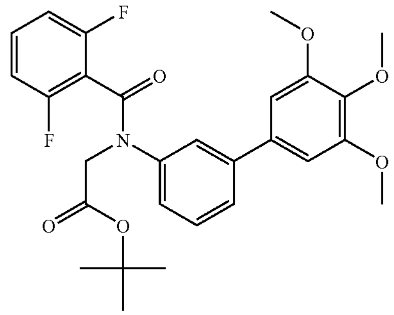 | 458.1 (M − 55)+ |
| 325 | 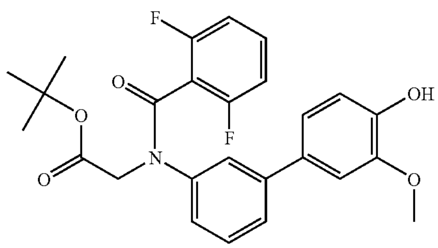 | 414.1 (M − 55)+ |
| 326 | 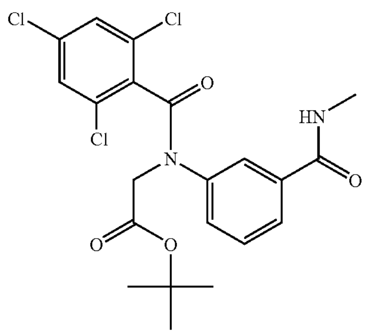 | 493.0 (M + 23)+ |

Assay 1—Transcriptional Assay

Transfection assays are used to assess the ability of compounds of the invention to modulate the transcriptional activity of the LXRs. Briefly, expression vectors for chimeric proteins containing the DNA binding domain of yeast GAL4 fused to the ligand-binding domain (LBD) of either LXRα or LXRβ are introduced via transient transfection into mammalian cells, together with a reporter plasmid where the luciferase gene is under the control of a GAL4 binding site. Upon exposure to an LXR modulator, LXR transcriptional activity varies, and this can be monitored by changes in luciferase levels. If transfected cells are exposed to an LXR agonist, LXR-dependent transcriptional activity increases and luciferase levels rise.

293T human embryonic kidney cells ($8\times10^6$) are seeded in a 175 cm$^2$ flask 2 days prior to the start of the experiment in 10% FBS, 1% Penicillin/Streptomycin/Fungizome, DMEM Media. The transfection mixture for chimeric proteins is prepared using GAL4-LXR LBD expression plasmid (4 µg), UAS-luciferase reporter plasmid (5 µg), Fugene (3:1 ratio; 27 µL) and serum-free media (210 µL). The transfection mixture is incubated for 20 minutes at room temperature. The cells are harvested by washing with PBS (30 mL) and then dissociated using trypsin (0.05%; 3 mL). The trypsin is inactivated by the addition of assay media (DMEM, lipoprotein-deficient fetal bovine serum (5%), statin (e.g. lovastatin 7.5 µM), and mevalonic acid (100 µM)) (10 mL). The cells are counted using a 1:10 dilution and the concentration of cells adjusted to 160,000 cells/mL. The cells are mixed with the transfection mixture (10 mL of cells per 250 µl of transfection mixture) and are further incubated for 30 minutes at room temperature with periodic mixing by inversion. Cells (50 µl/well) are then plated into 384 white, solid-bottom, TC-treated plates. The cells are further incubated at 37° C., 5.0% $CO_2$ for 24 hours. A 12-point series of dilutions (half-log serial dilutions) are prepared for each test compound in DMSO with a starting concentration of compound of 1 µM. Test compound (500 nl) is added to each well of cells in the assay plate and the cells are incubated at 37° C., 5.0% $CO_2$ for 24 hours. The cell lysis/luciferase assay buffer Bright-Glo™ (25%; 25 µl; Promega), is added to each well. After a further incubation for 5 minutes at room temperature, the luciferase activity is measured.

Raw luminescence values are normalized by dividing them by the value of the DMSO control present on each plate. Normalized data is visualized using XLfit3 and dose-response curves are fitted using a 4-parameter logistic model or sigmoidal single-site dose-response equation (equation 205 in XLfit3.05). EC50 is defined as the concentration at which the compound elicits a response that is half way between the maximum and minimum values. Relative efficacy (or percent efficacy) is calculated by comparison of the response elicited by the compound with the maximum value obtained for the known LXR modulator (3-{3-[(2-Chloro-3-trifluoromethyl-benzyl)-(2,2-diphenyl-ethyl)-amino]-propoxy}-phenyl)-acetic acid.

Assay2—FRET Co-Activator Recruitment Assay

A FRET assay is used to assess the ability of a compound of the invention to bind directly to the LXR ligand-binding domain (LBD) and promote the recruitment of proteins that potentiate the transcriptional activity of LXRs (e.g. co-activators). This cell-free assay uses a recombinant fusion protein composed of the LXR LBD and a tag (e.g. GST, His, FLAG) that simplifies its purification, and a synthetic biotinylated peptide derived from the nuclear receptor interacting domain of a transcriptional co-activator protein, such as steroid receptor co-activator 1 (SRC-1). In one format, the tagged LBD fusion protein can be labeled using an antibody against the LBD tag coupled to europium (e.g. EU-labeled anti-GST antibody), and the co-activator peptide can be labeled with allophycocyanin (APC) coupled to streptavidin. In the presence of an agonist for LXR, the co-activator peptide is recruited to the LXR LBD, bringing the EU and APC moieties in close proximity. Upon excitation of the complex with light at 340 nM, EU absorbs and transfers energy to the APC moiety resulting in emission at 665 nm. If there is no energy transfer (indicating lack of EU-APC proximity), EU emits at 615 nm. Thus the ratio of the 665 to 615 nm light emitted gives an indication of the strength of co-activator peptide recruitment, and thus of agonist binding to the LXR LBD.

Fusion proteins, amino acids 205-447 (Genbank NM_005693) for LXRα and amino acids 203-461 (NM_007121 for β) for LXRβ, were cloned in-frame at the Sal1 and Not1 sites of pGEX4T-3 (27-4583-03 Amersham Pharmacia Biotech). A biotinylated peptide sequence was derived from SRC-1 (amino acids 676 to 700): biotin-CPSSHSSLTERH-KILHRLLQEGSPSC-OH.

A master mix is prepared (5 nM GST-LXR-LBD, 5 nM Biotinylated SRC-1 peptide, 10 nM APC-Streptavidin (Prozyme Phycolink streptavidin APC, PJ25S), and 5n MEU-Anti-GST Antibody) in FRET buffer (50 mM Tris pH 7.5, 50 mM KCl 1 mM DTT, 0.1% BSA). To each well of a 384 well plate, 20 µL of this master mix is added. Final FRET reaction: 5 nM fusion protein, 5 nM SRC-1 peptide, 10 nM APC-Streptavidin, 5 nm EU-Anti-GST Antibody (PerkinElmer AD0064). Test compounds are diluted in half-log, 12-point serial dilutions in DMSO, starting at 1 mM and 100 mL of compound is transferred to the master mix for a final concentration of 5 µM-28 pM in the assay wells. Plates are incubated at room temperature for 3 hours and fluorescence resonance energy transfer read. Results are expressed as the ratio of APC fluorescence to EU fluorescence times one thousand.

The ratio of 665 nm to 615 nm is multiplied by a factor of 1000 to simplify data analysis. DMSO values are subtracted from ratios to account for background. Data is visualized using XLfit3 and dose-response curves are fitted using a 4-parameter logistic model or sigmoidal single-site dose-response equation (equation 205 in XLfit3.05). EC50 is defined as the concentration at which the compound elicits a response that is half way between the maximum and minimum values. Relative efficacy (or percent efficacy) is calcu-lated by comparison of the response elicited by the compound with the maximum value obtained for a reference LXR modulator.

Compounds of Formula I, in free form or in pharmaceutically acceptable salt form, exhibit valuable pharmacological properties, for example, as indicated by the in vitro tests described in this application. Compounds of the invention have EC50 between 0.001 µM and 1.5 µM and % Efficacy between 20% and 150% in the transcriptional assay for LXRβ. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound selected from:

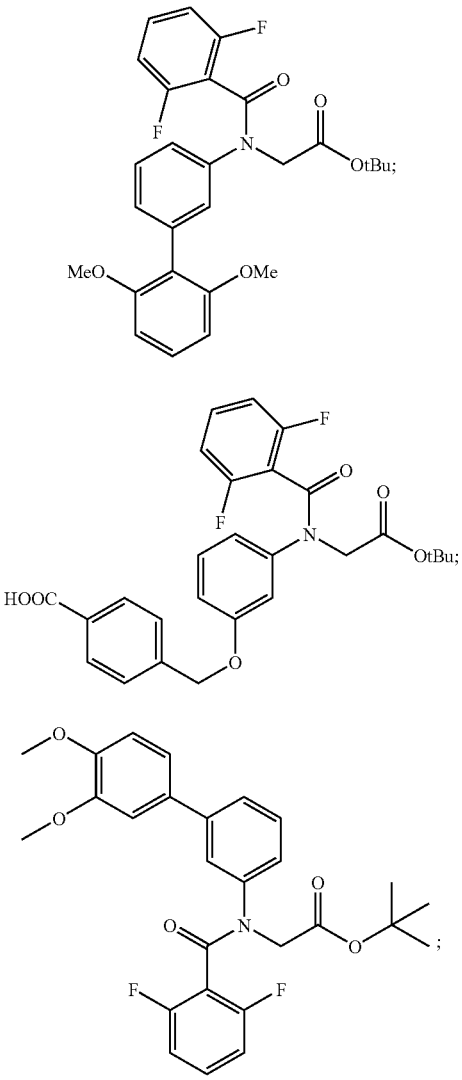

-continued
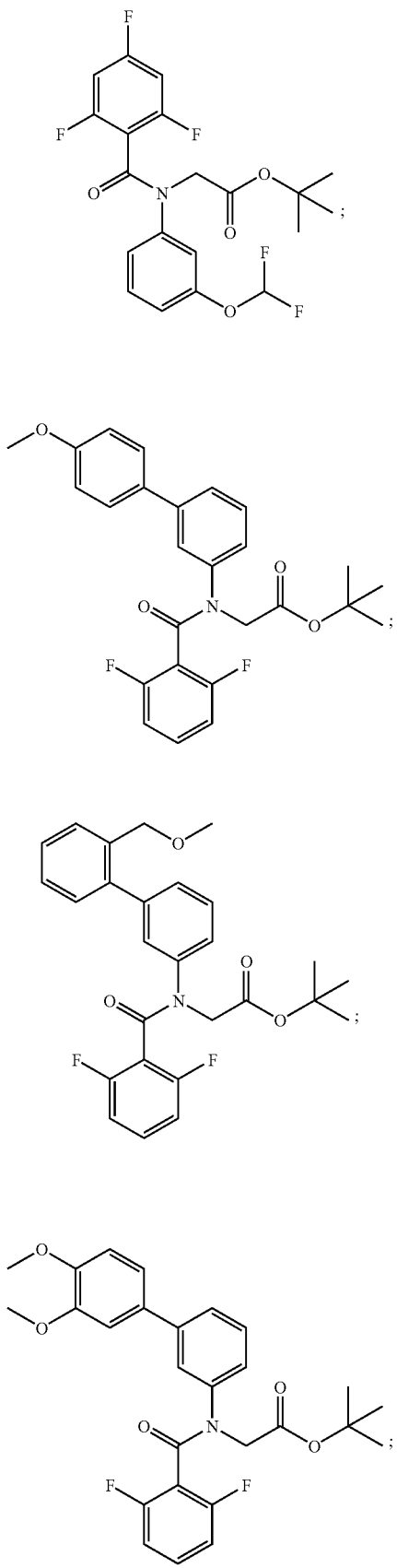
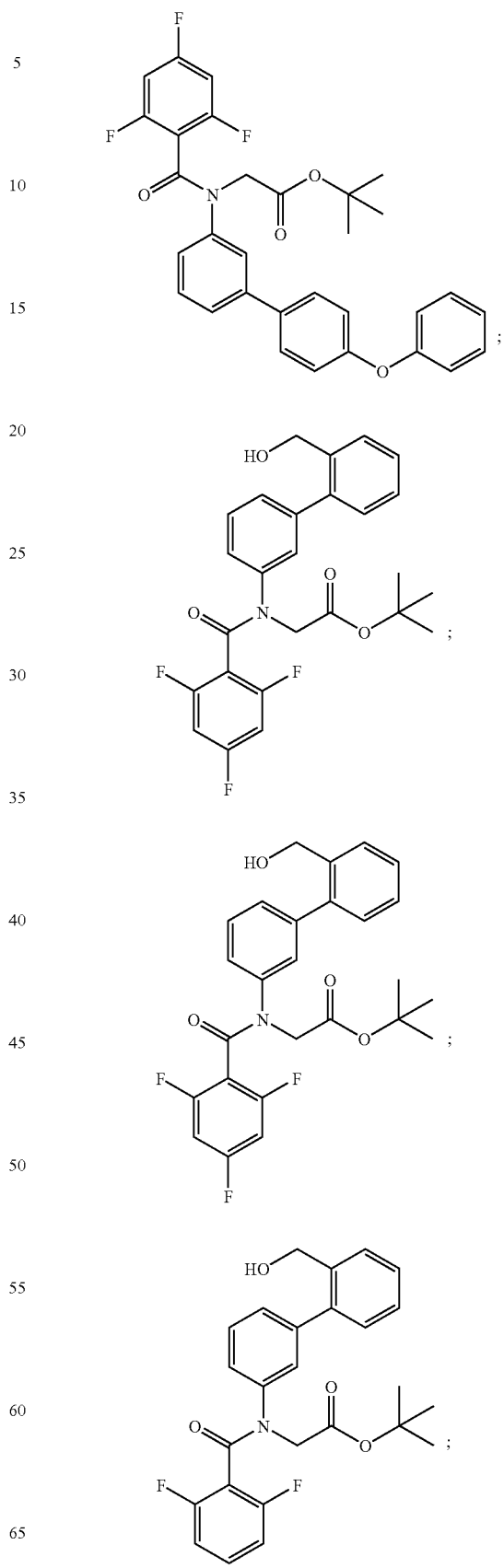

161
-continued
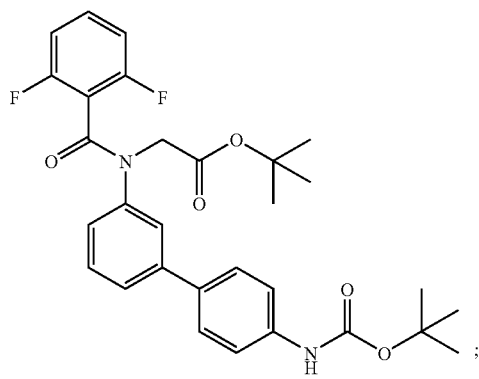
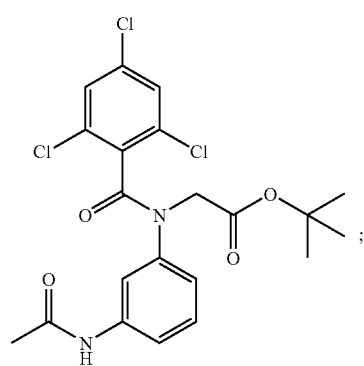
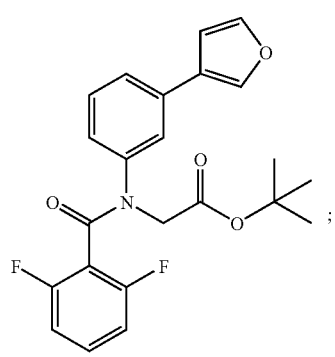
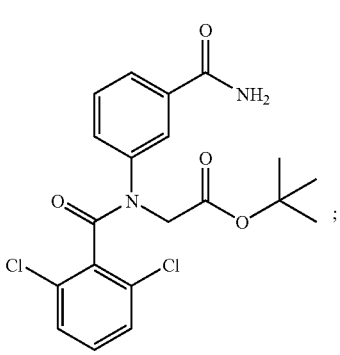
162
-continued
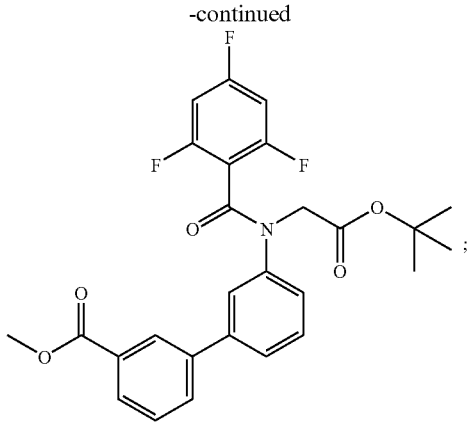
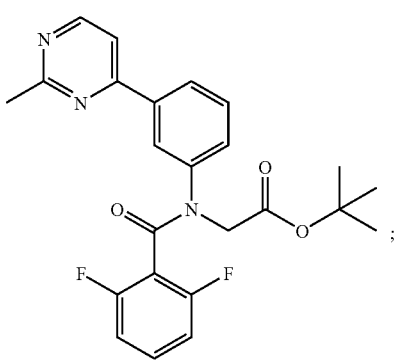
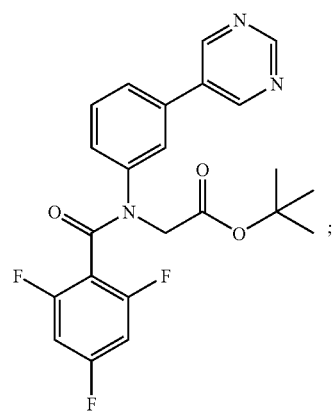
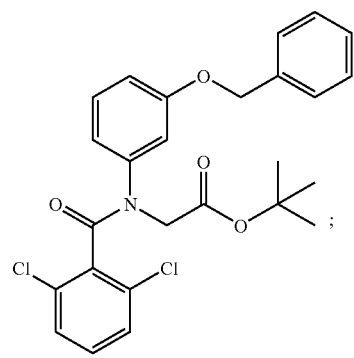

-continued
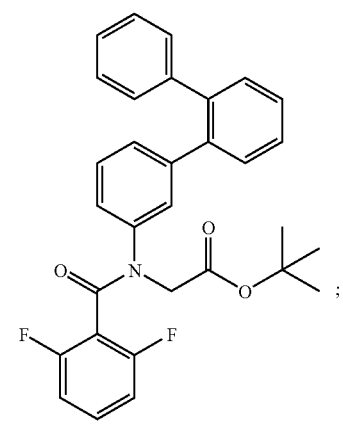
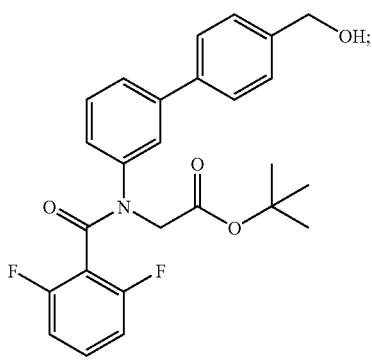
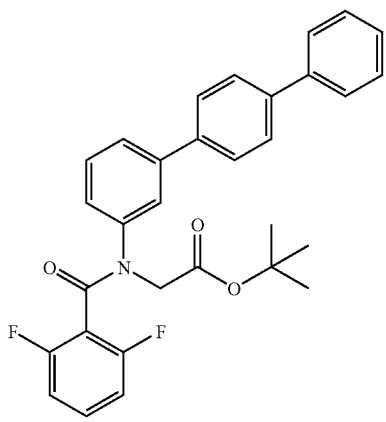
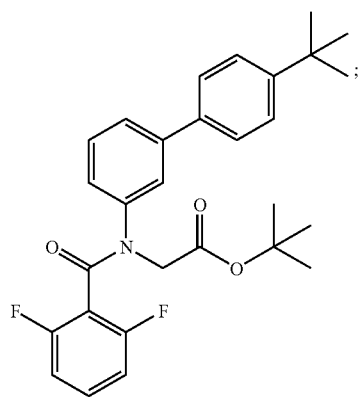
-continued
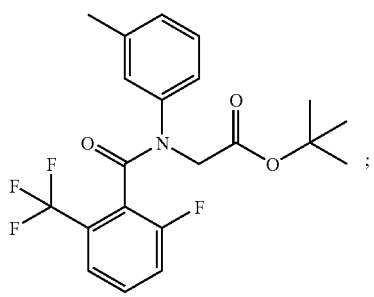
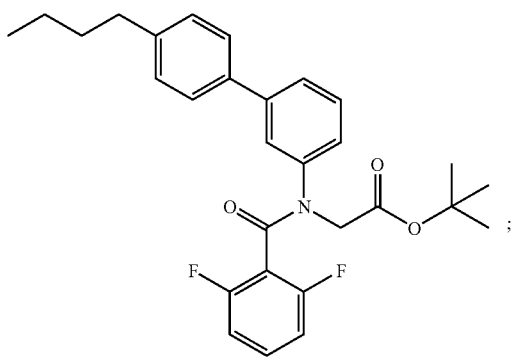
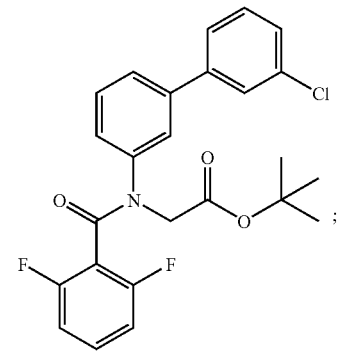
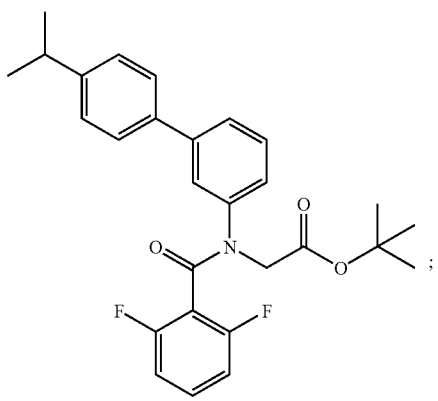

165
-continued
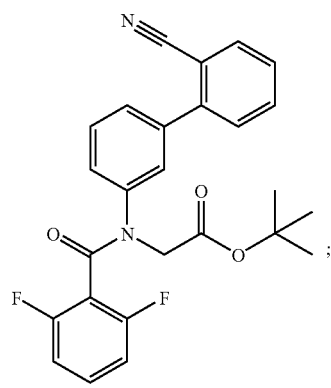
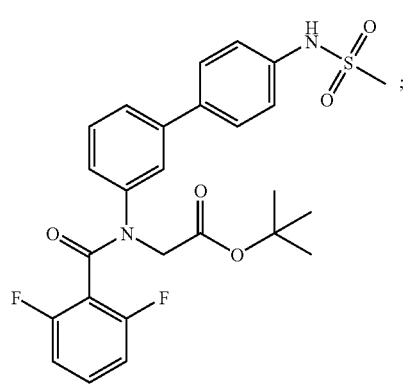
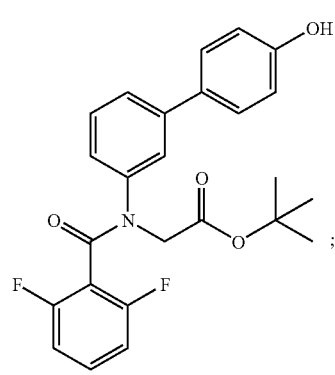
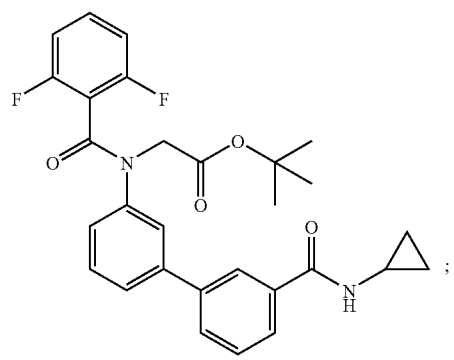
166
-continued
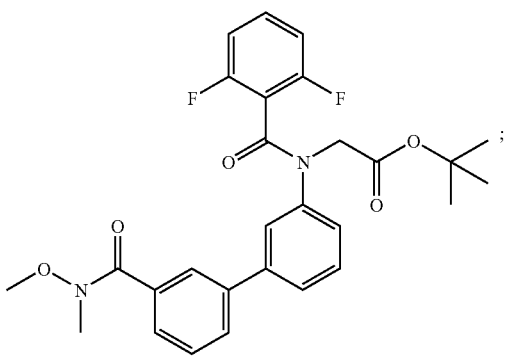
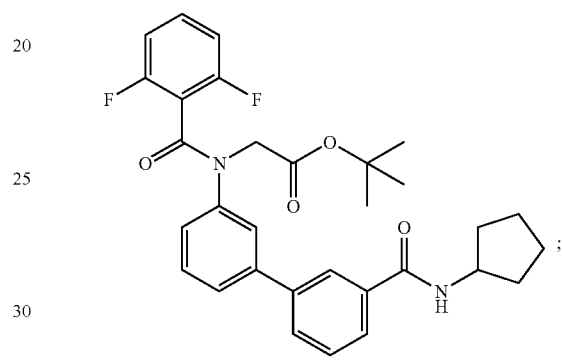
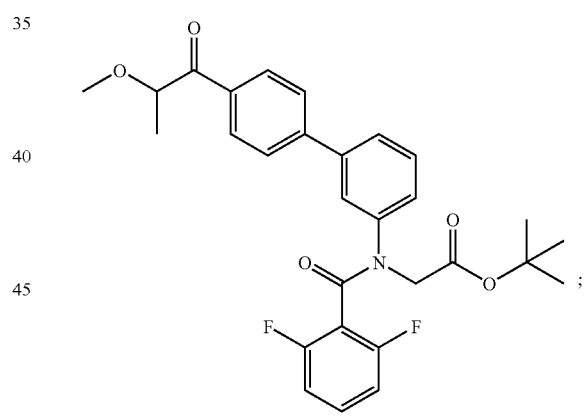
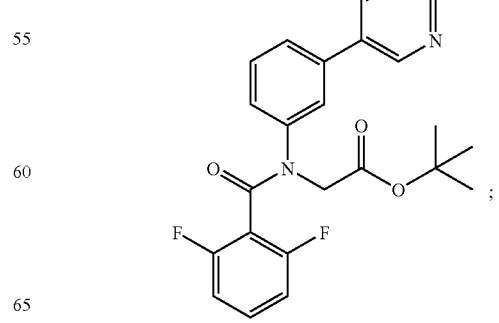

167
-continued
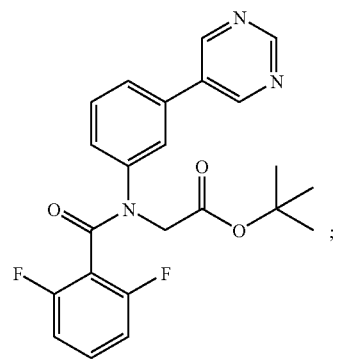
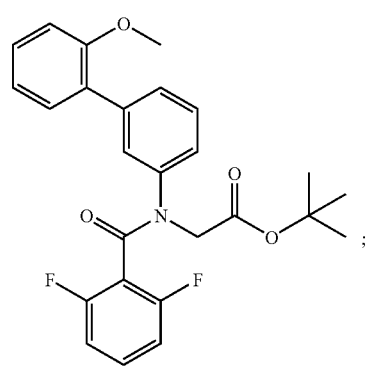
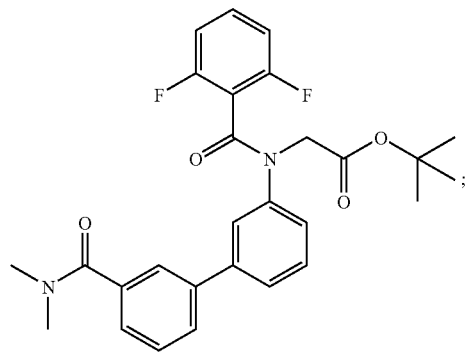
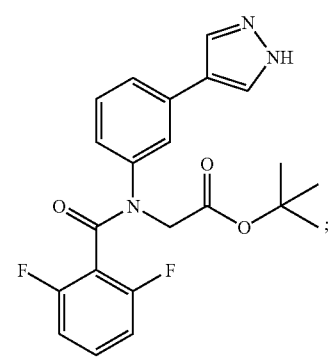
168
-continued
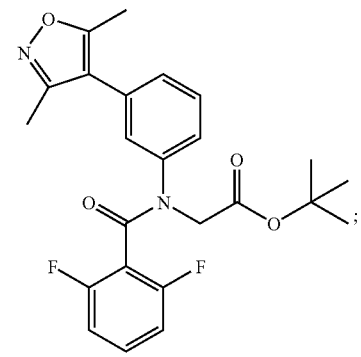
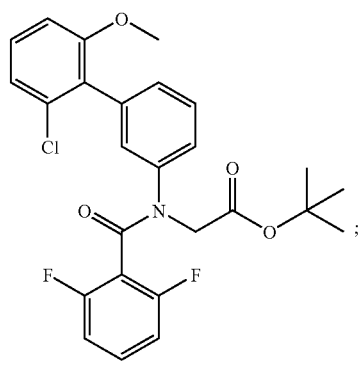
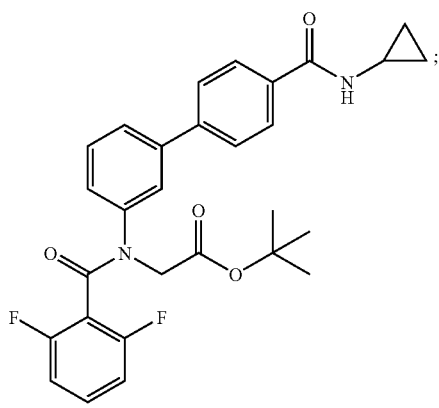
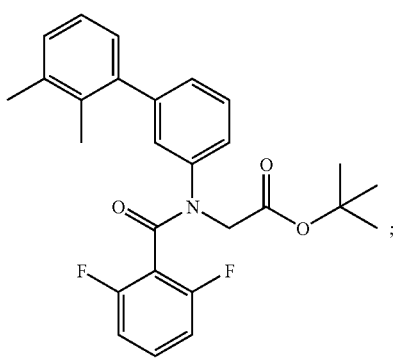

-continued
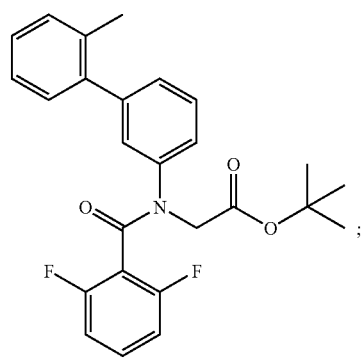
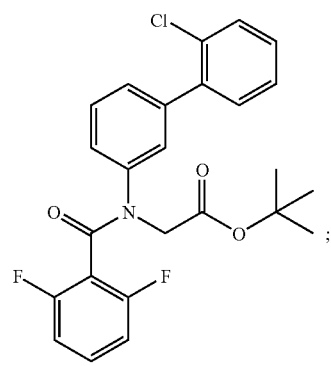
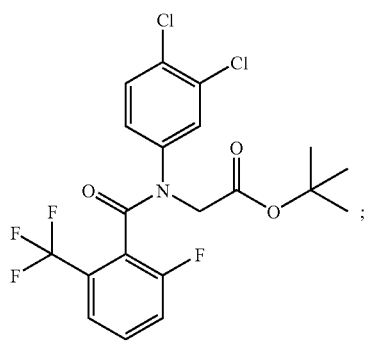
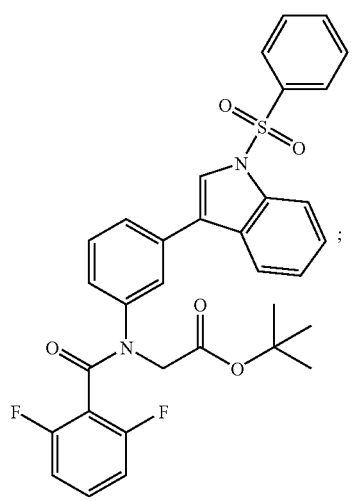
-continued
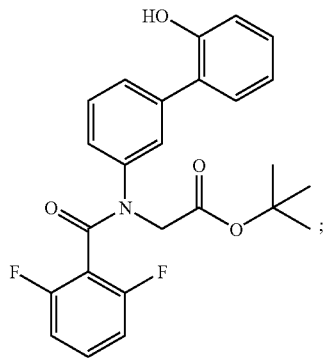
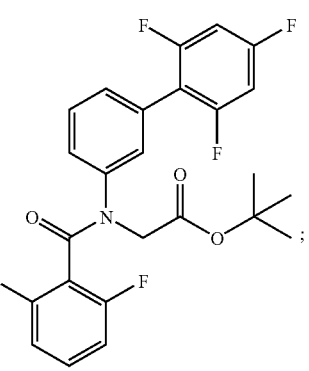
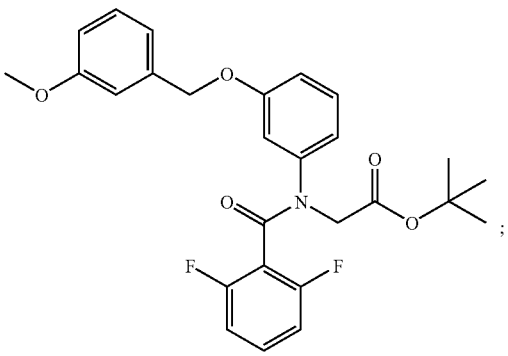
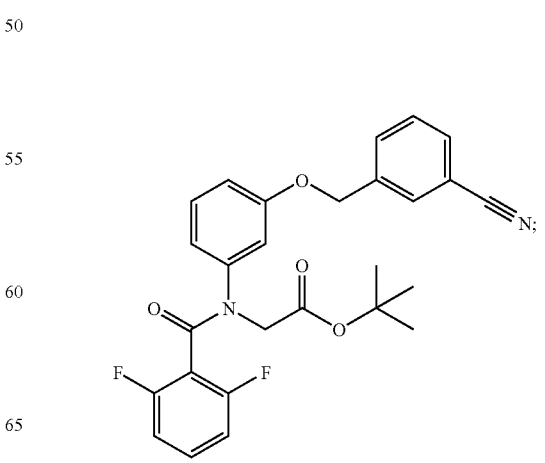

171
-continued
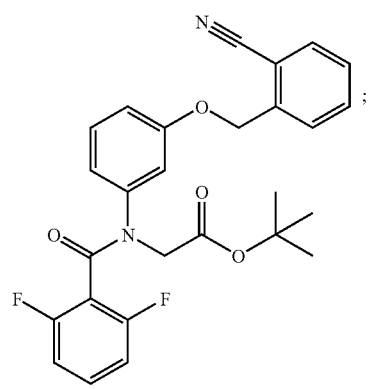
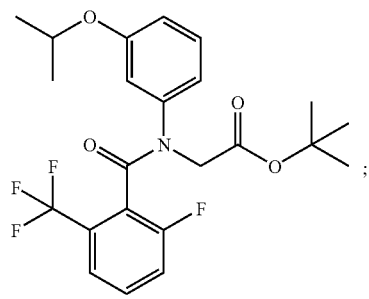
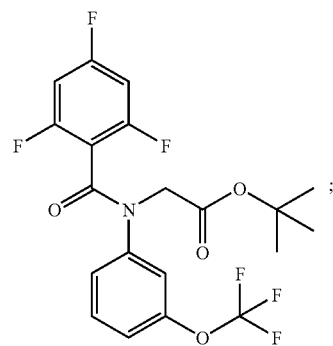
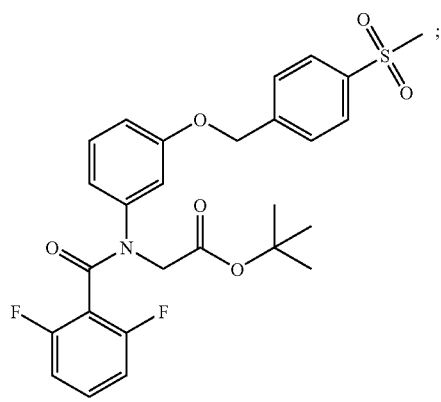
172
-continued
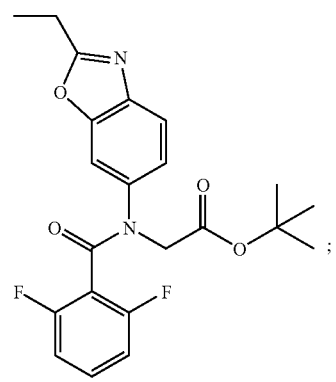
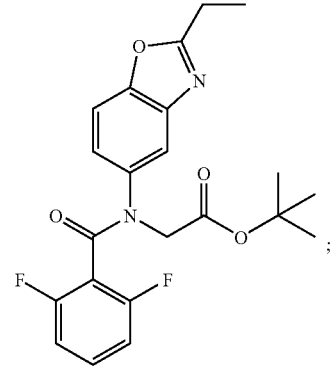
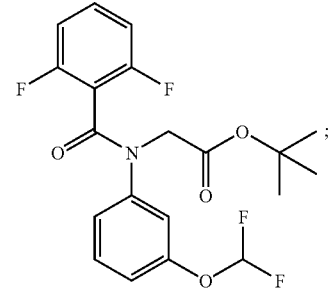

173
-continued
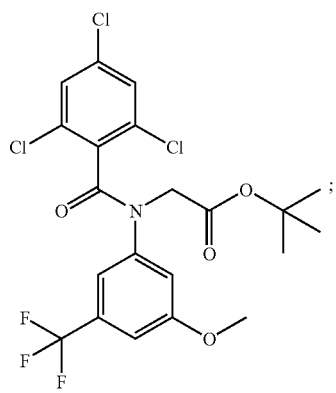
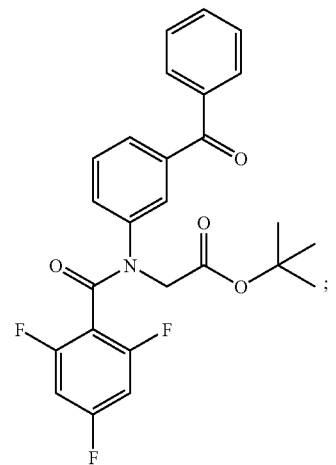
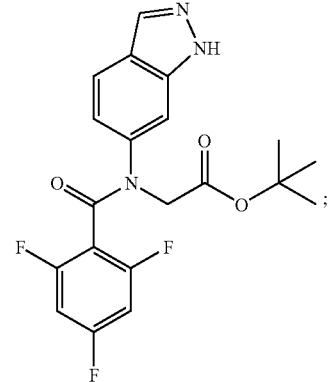
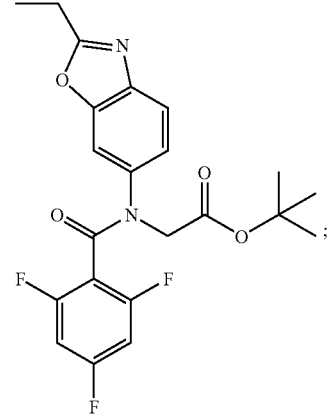
174
-continued
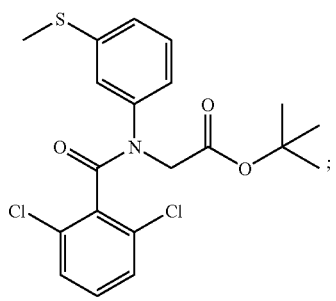
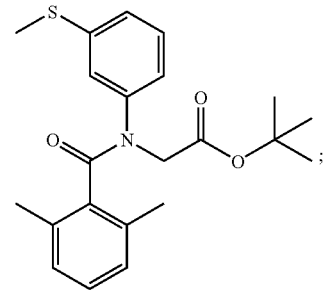
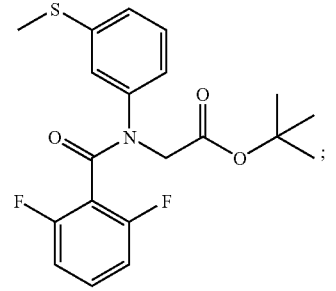
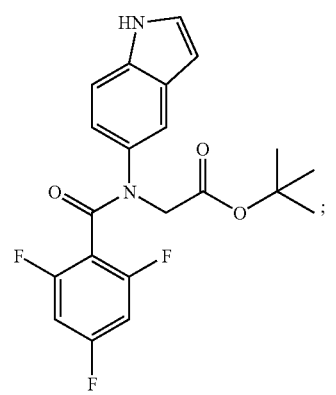
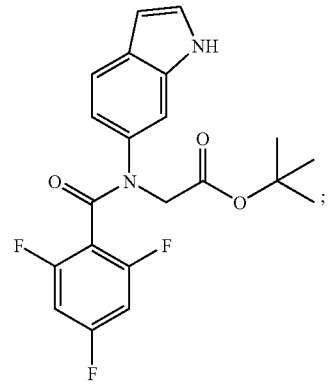

-continued
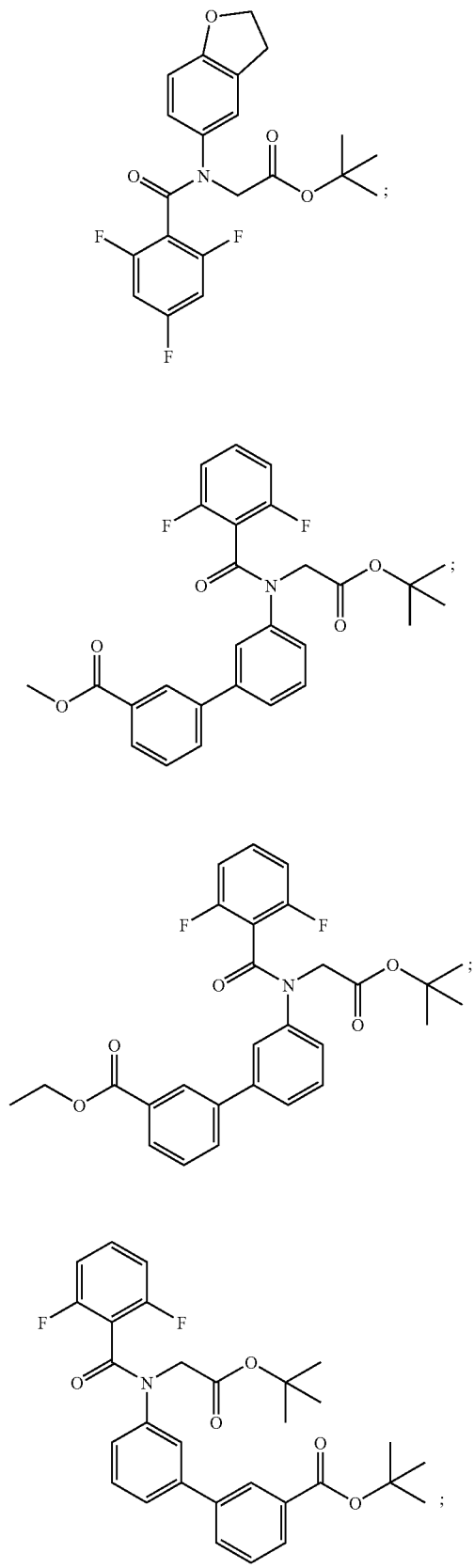
-continued
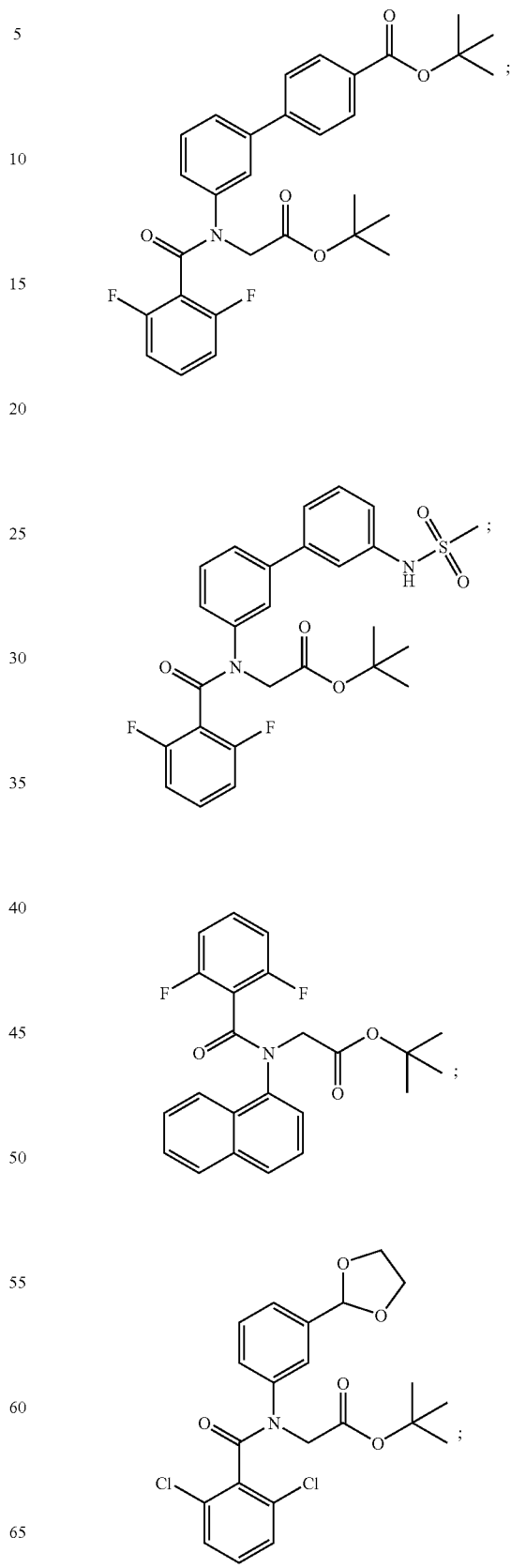

-continued
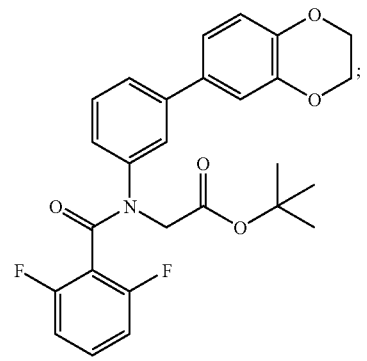
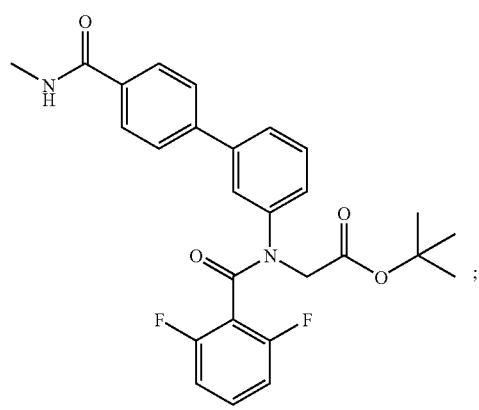
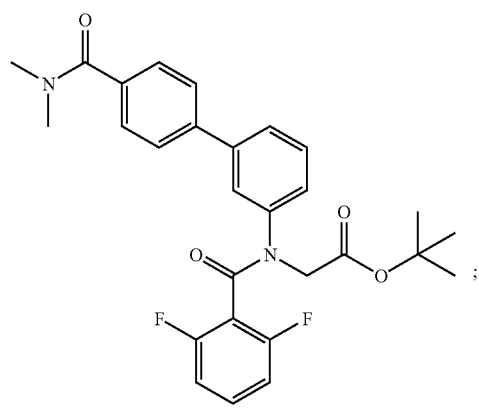
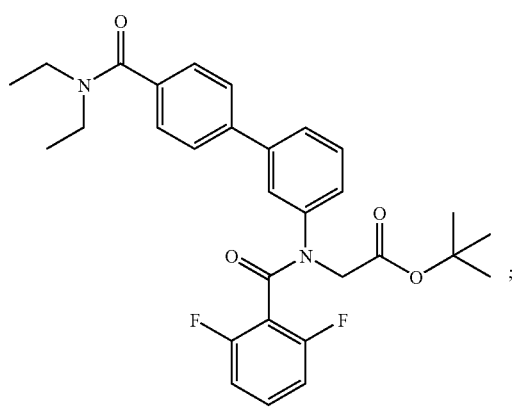
-continued
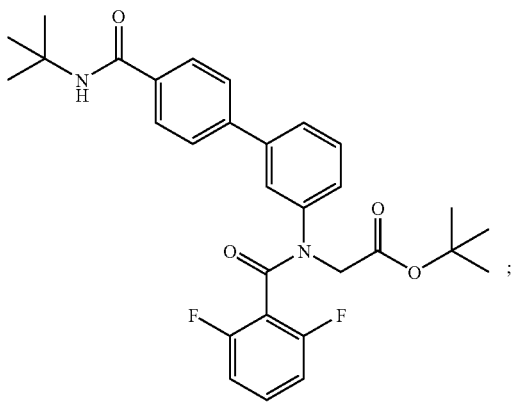
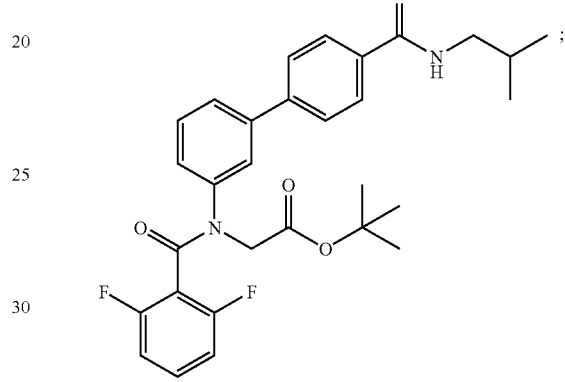
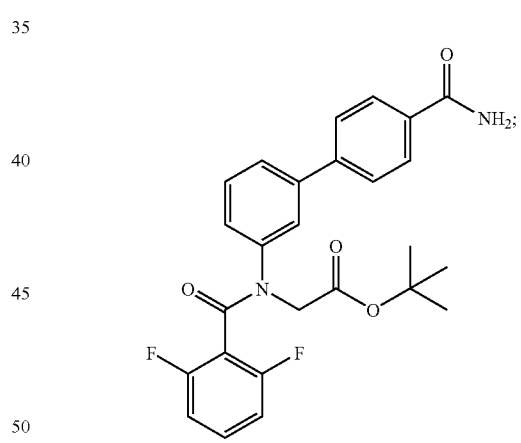
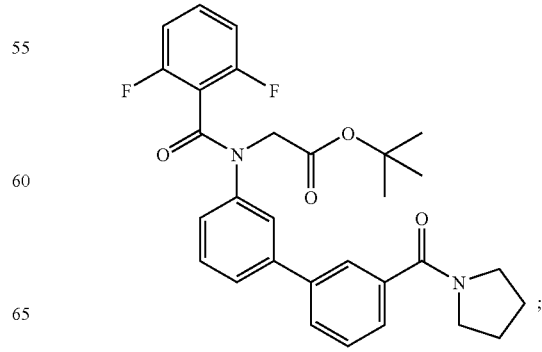

-continued
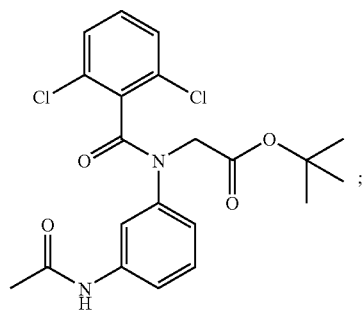
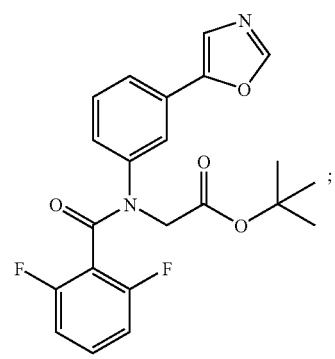
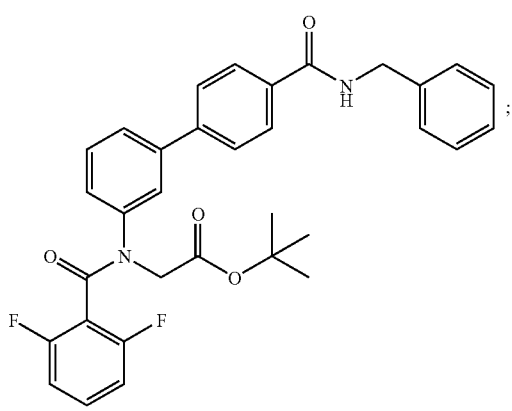
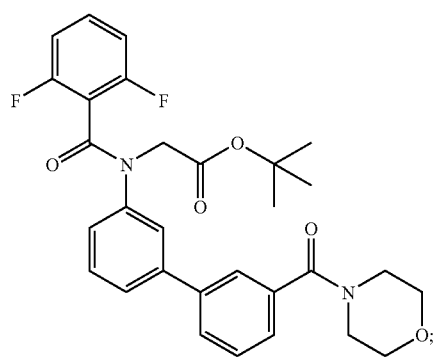
-continued
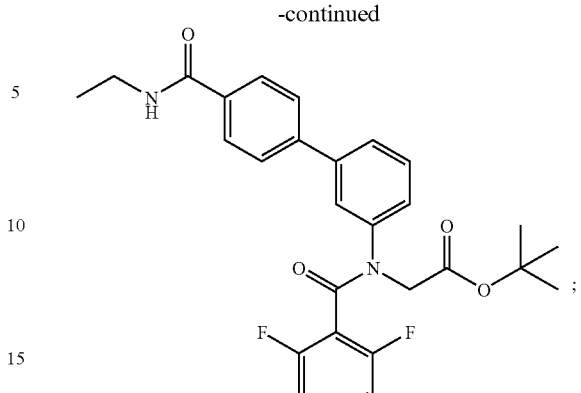
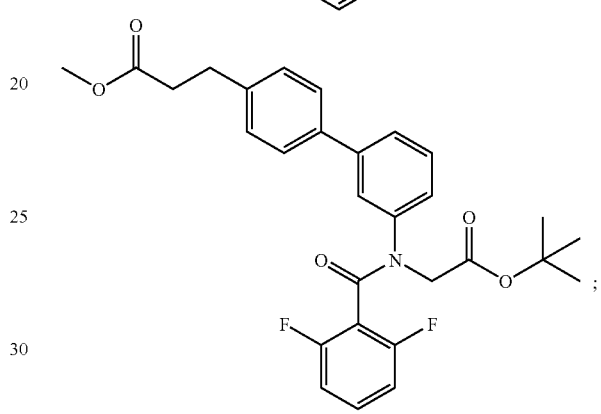
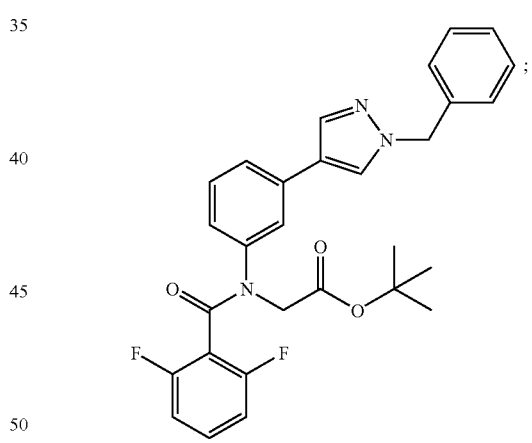
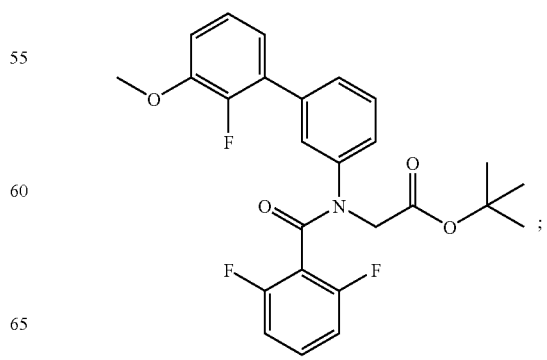

181
-continued
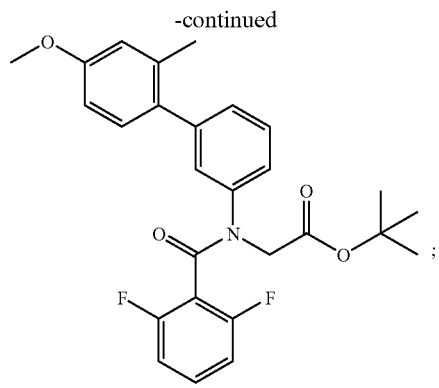
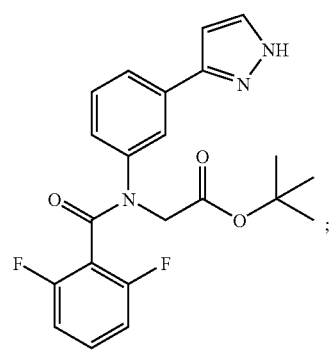
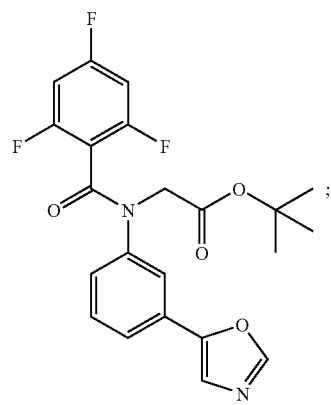
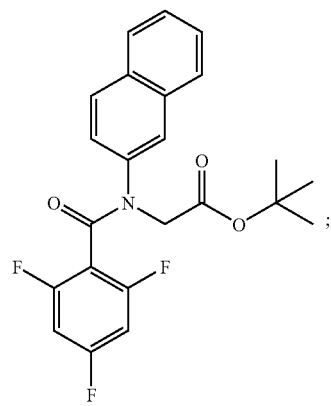
182
-continued
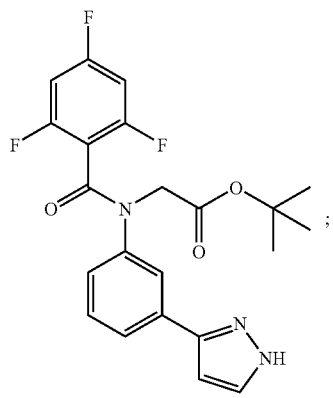
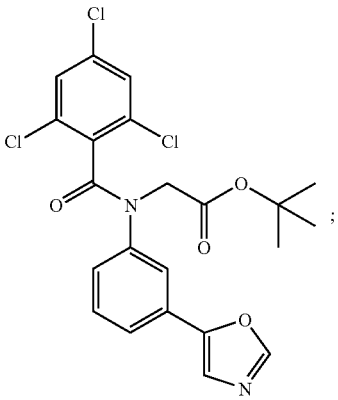
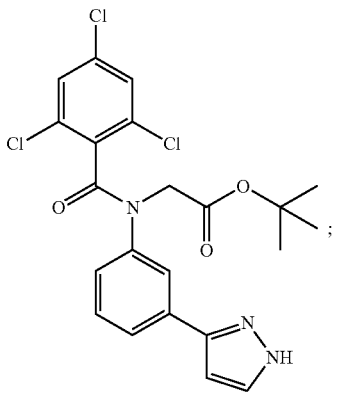
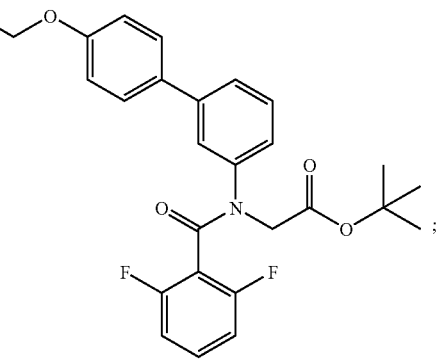

-continued
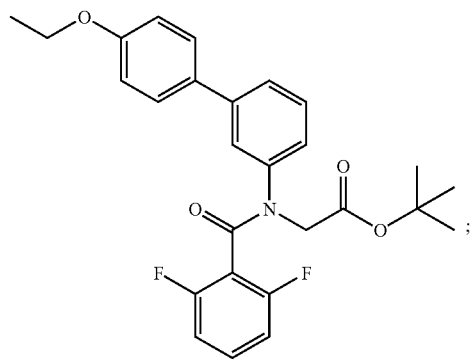
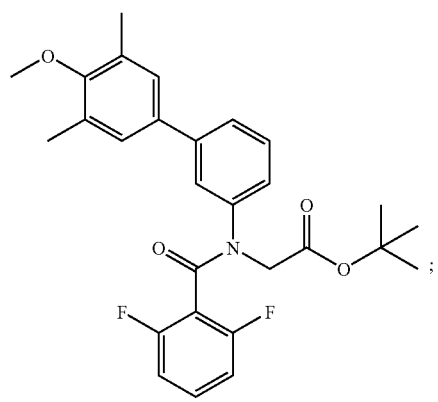
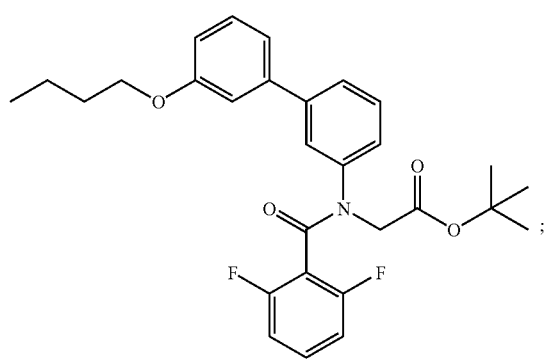
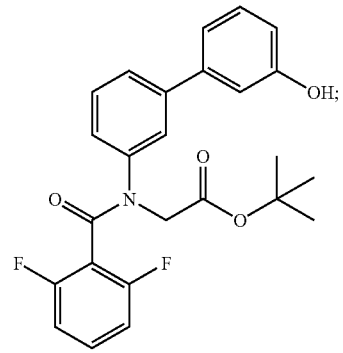
-continued
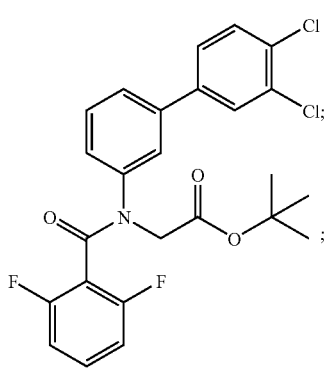
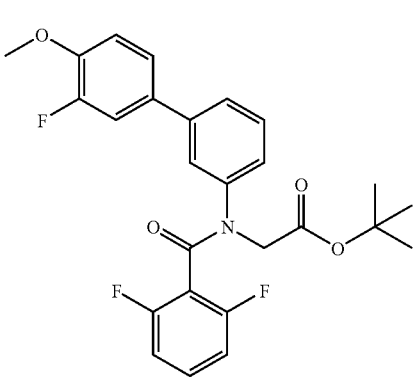
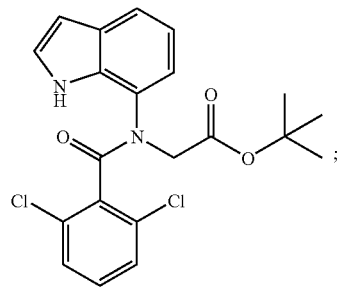
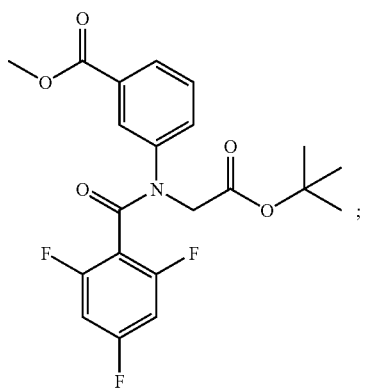

185
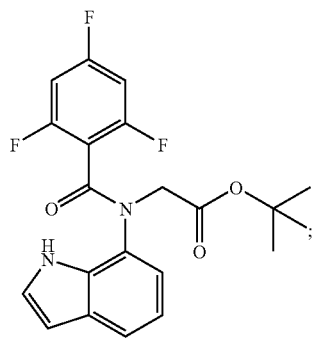
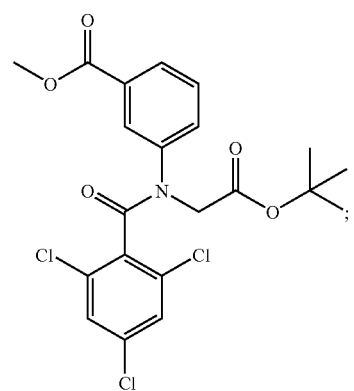
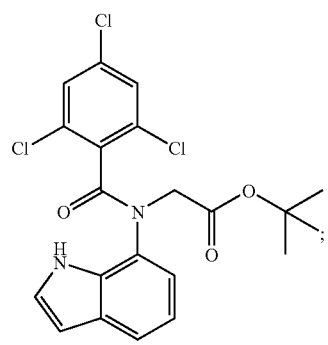
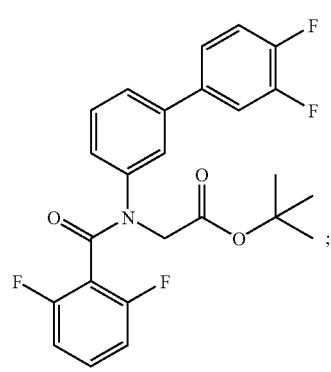
186
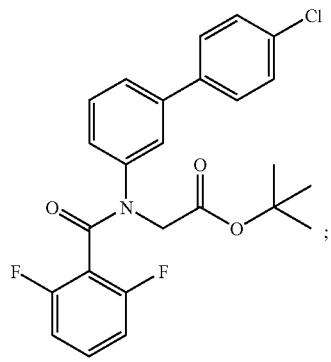
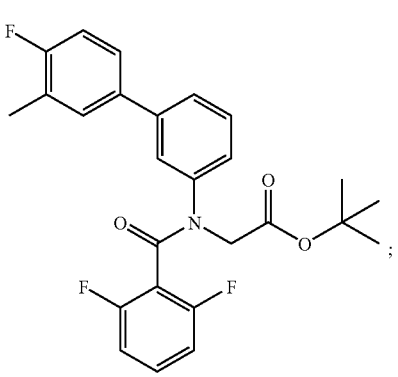
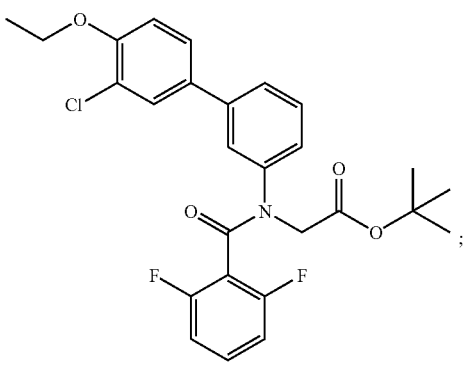
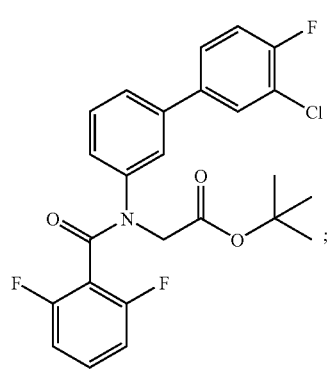

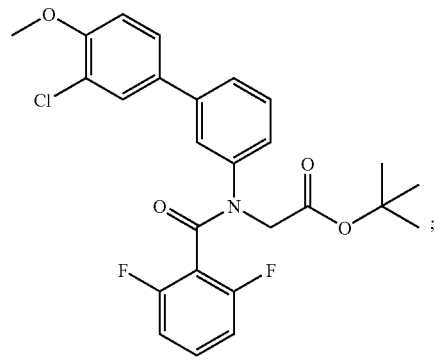
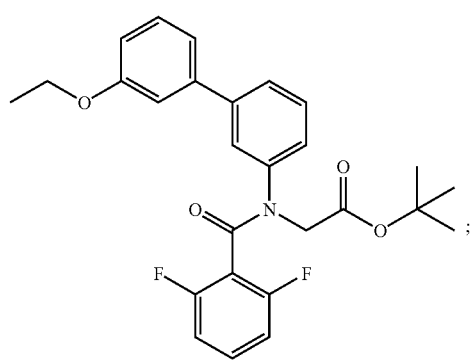
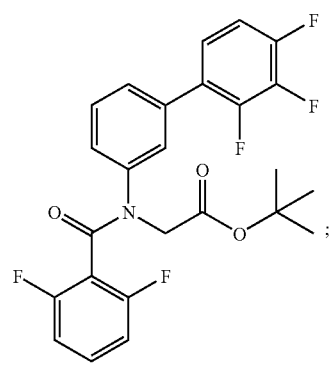
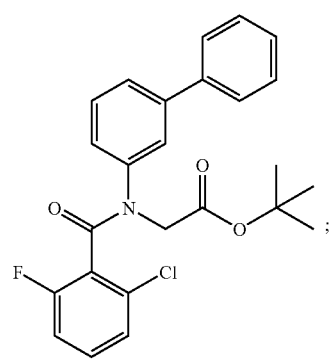
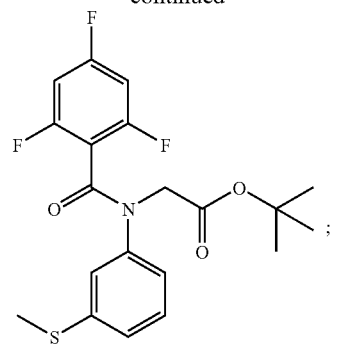
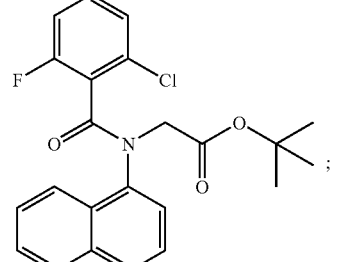
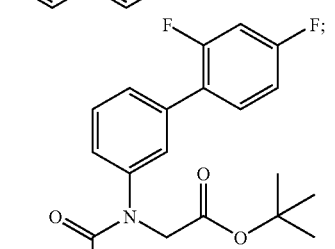
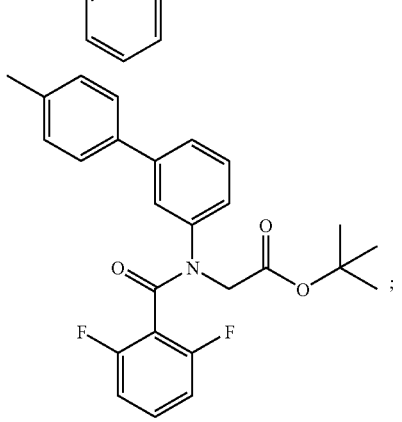
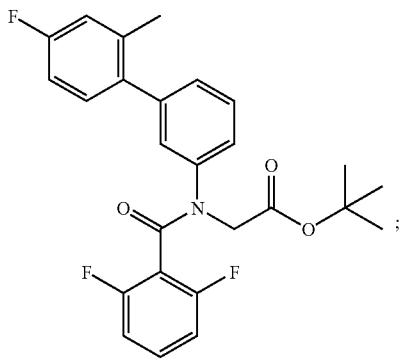

189
-continued
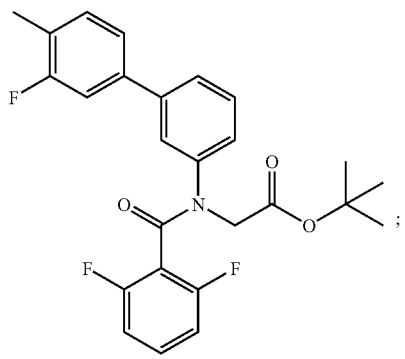
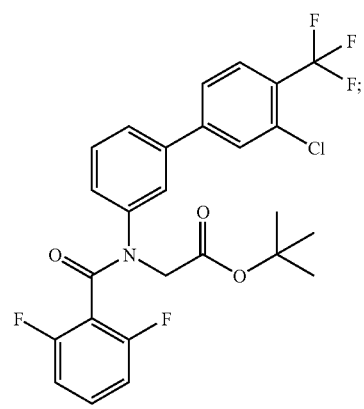
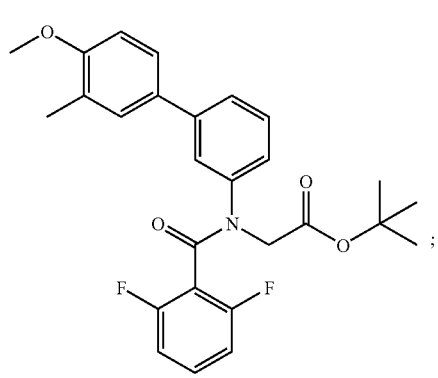
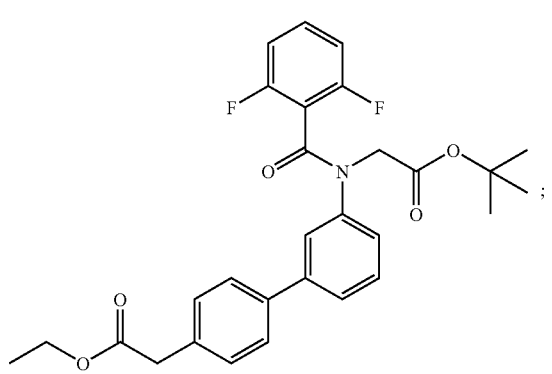
190
-continued
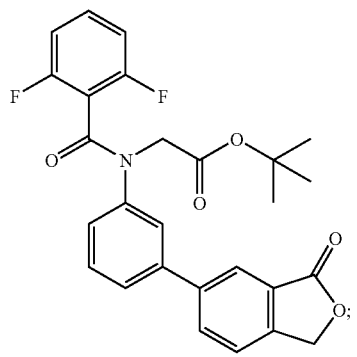
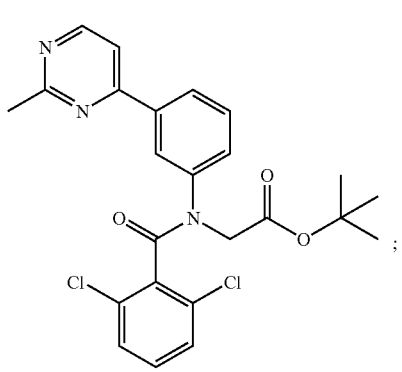
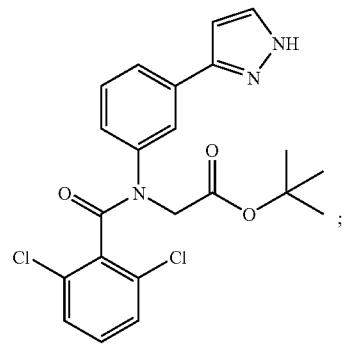
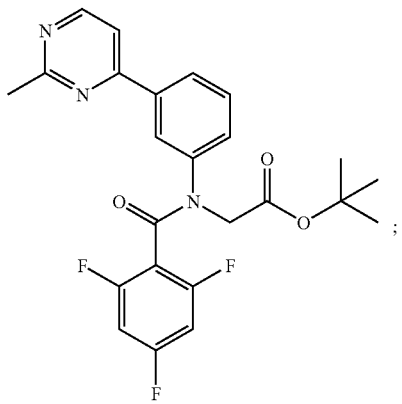

191
-continued
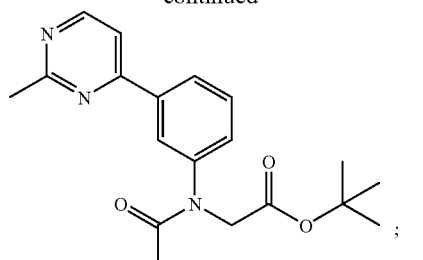
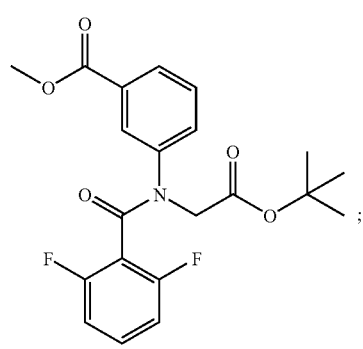
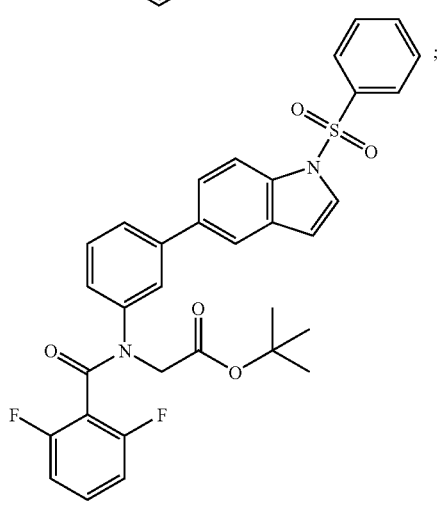
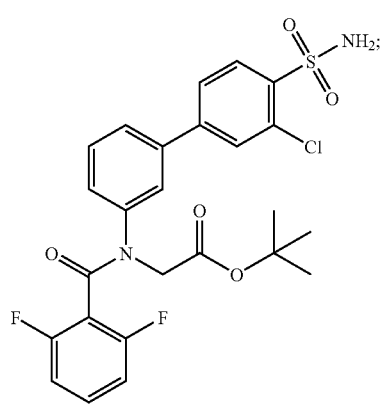
192
-continued
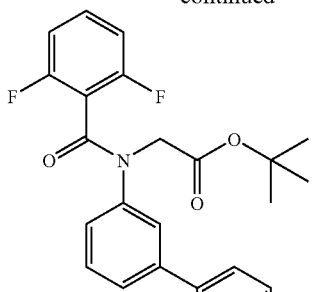
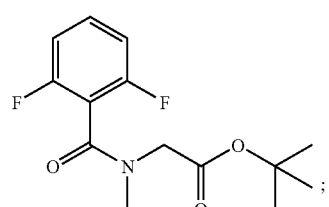
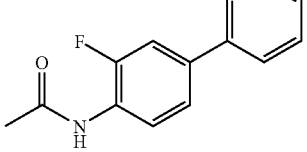
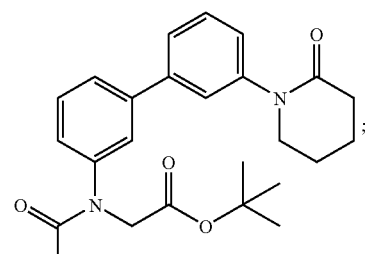
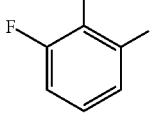
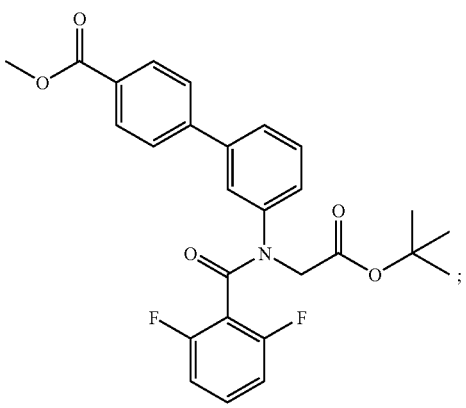

193
-continued
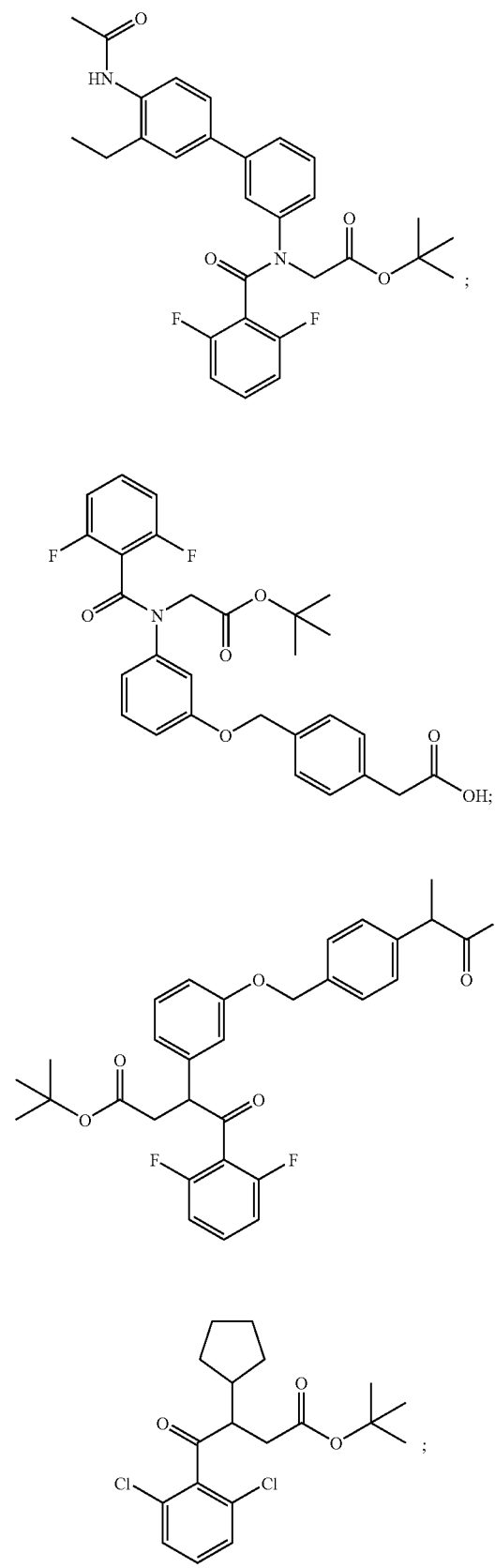
194
-continued
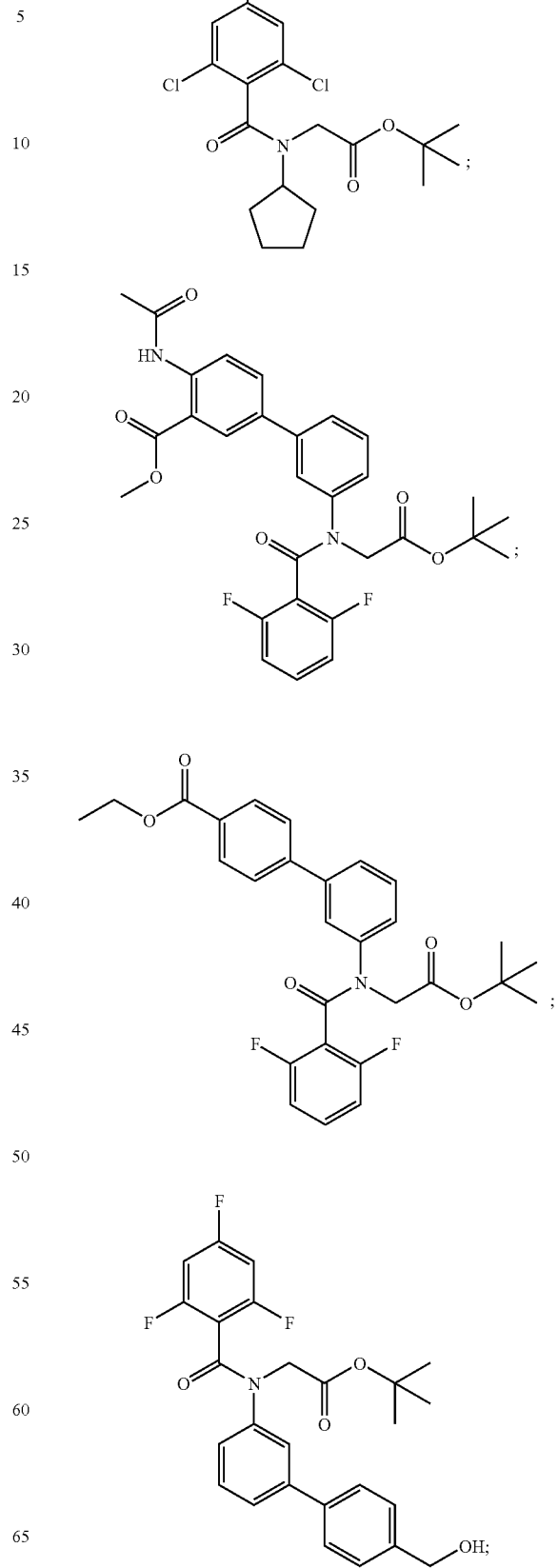

195
-continued
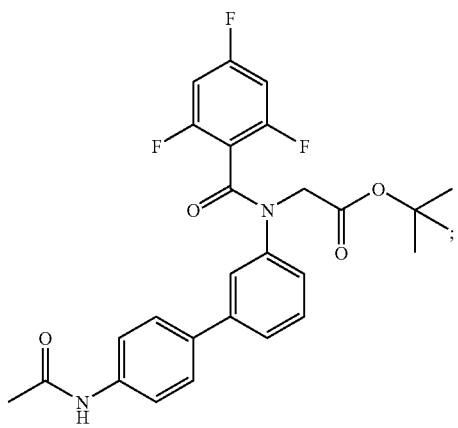
196
-continued
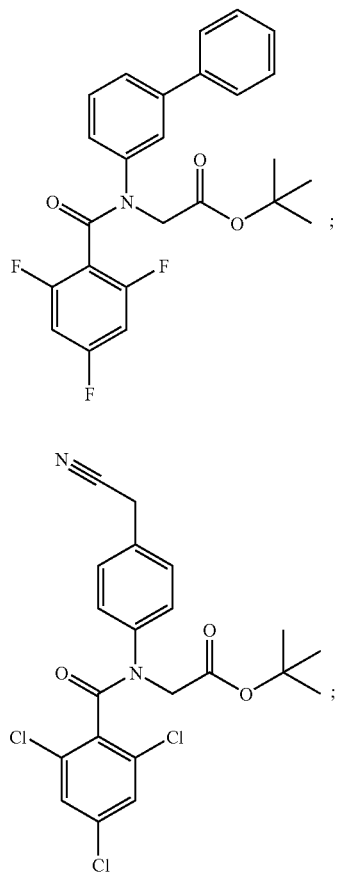

197
-continued
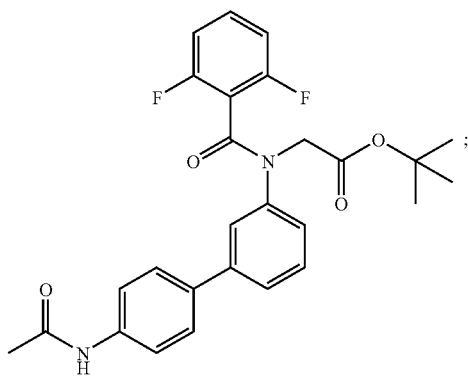
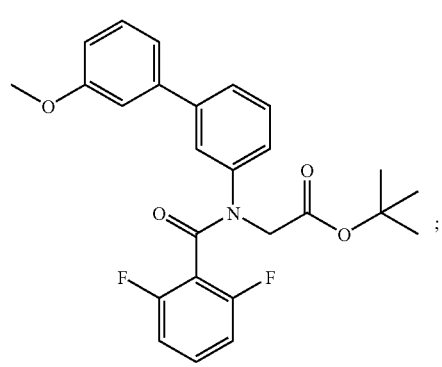
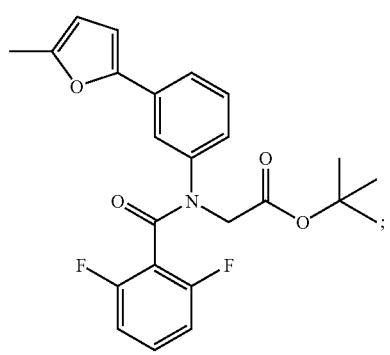
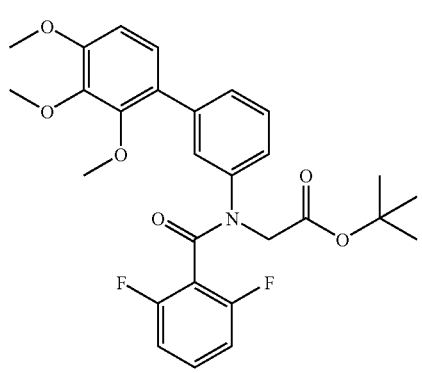
198
-continued
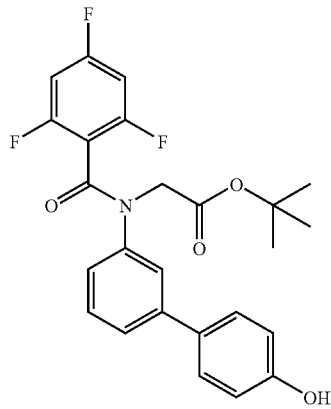
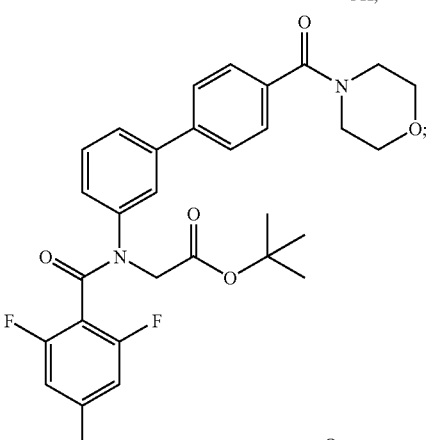
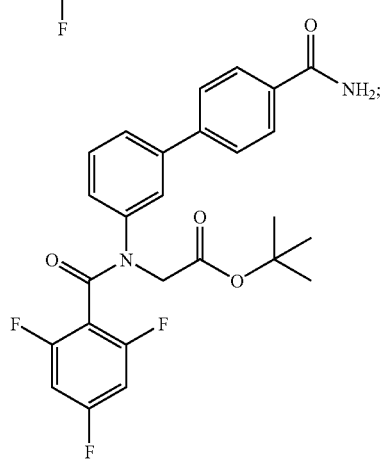
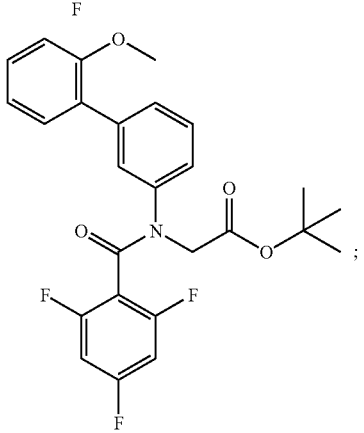

199
-continued
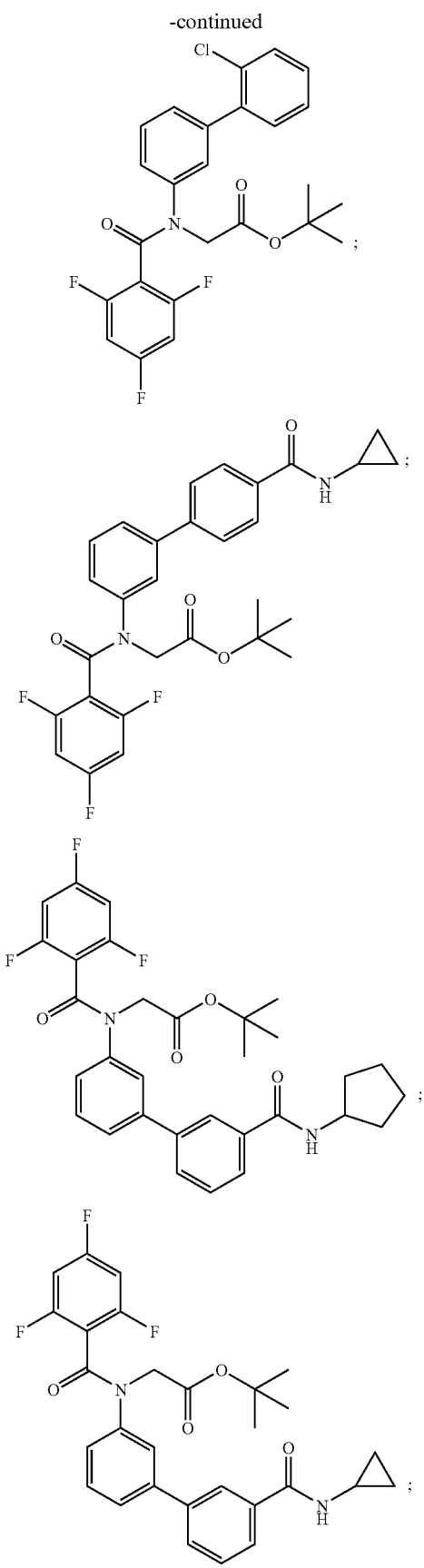
200
-continued
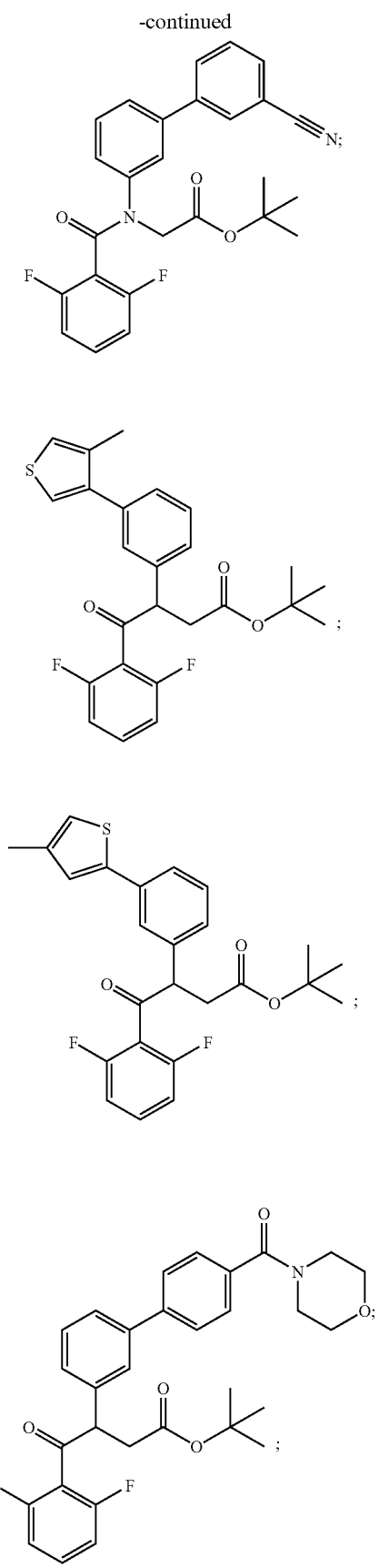

201
-continued
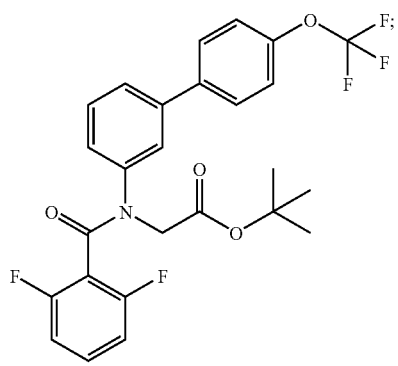
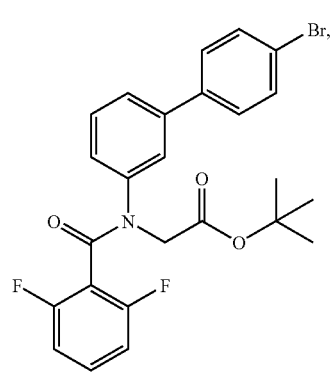
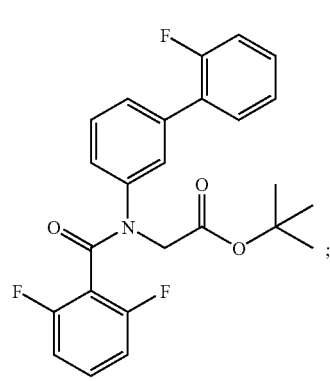
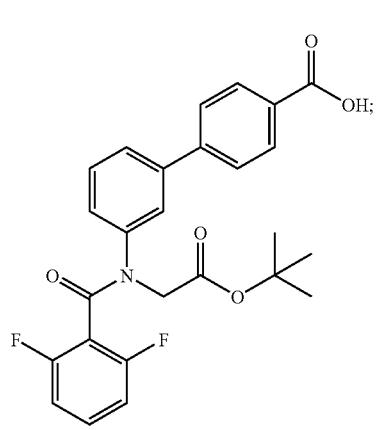
202
-continued
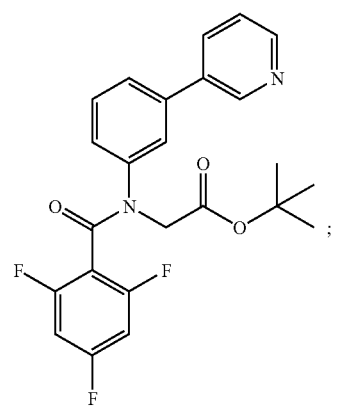
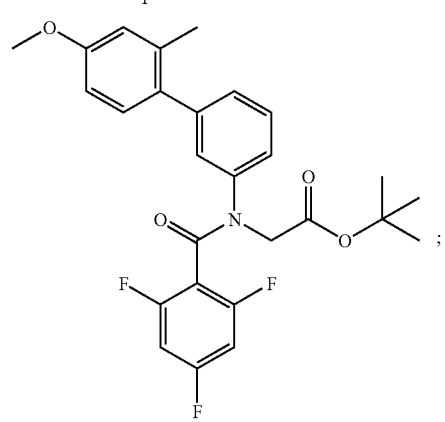
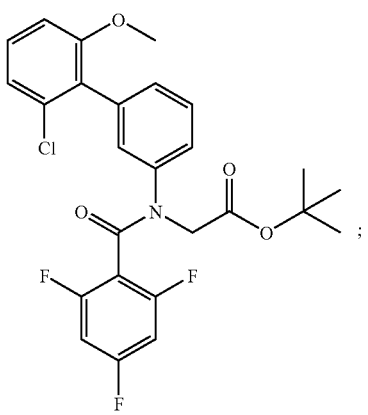
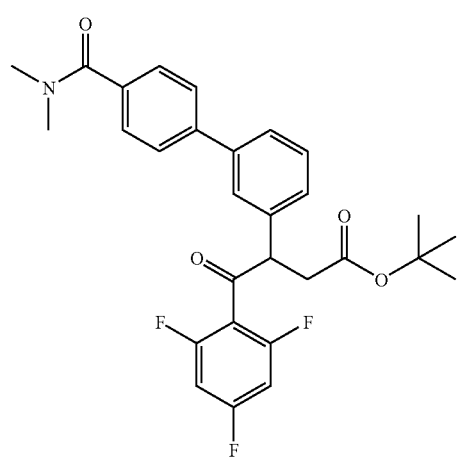

203
-continued
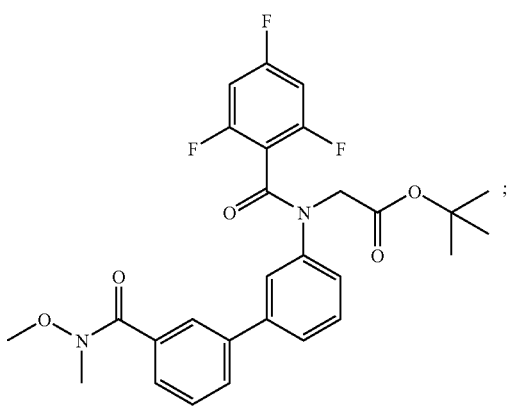
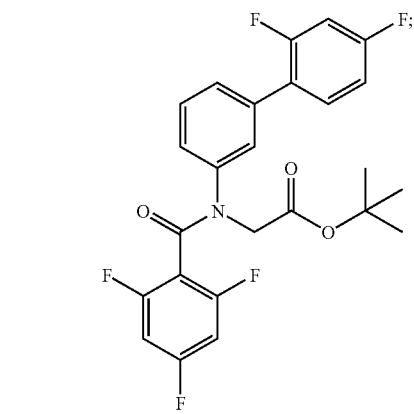
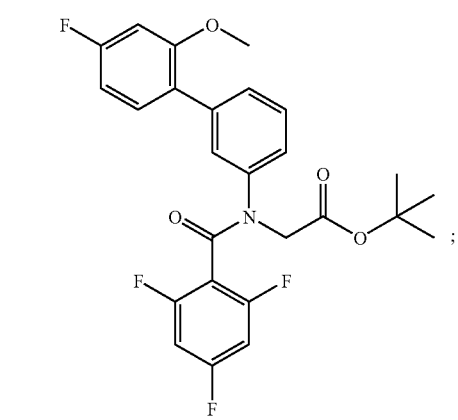
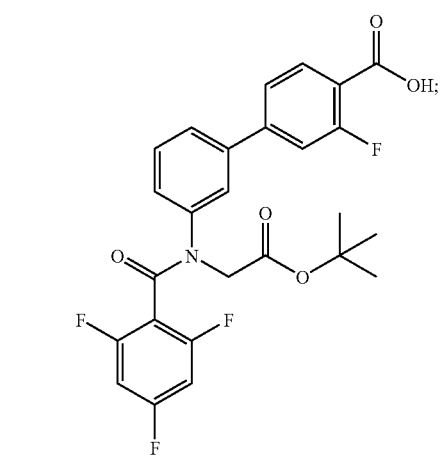
204
-continued
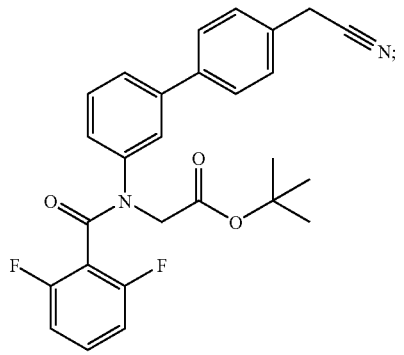
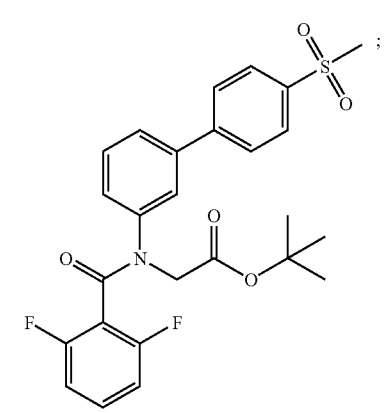
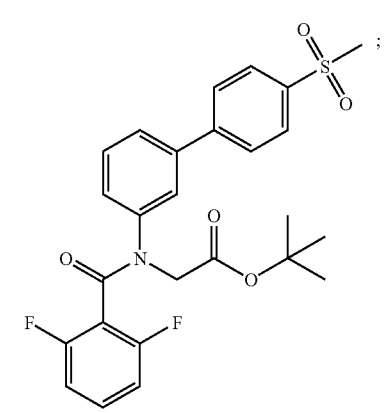
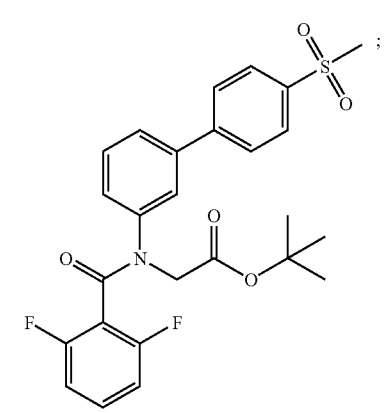

205
-continued
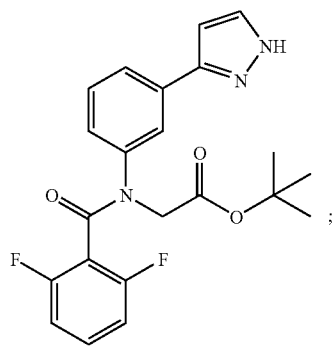
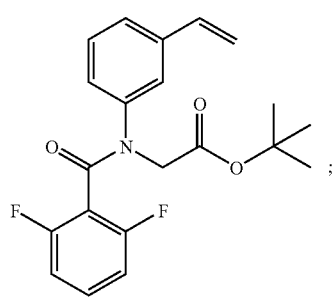
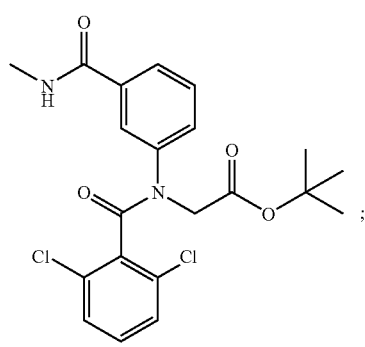
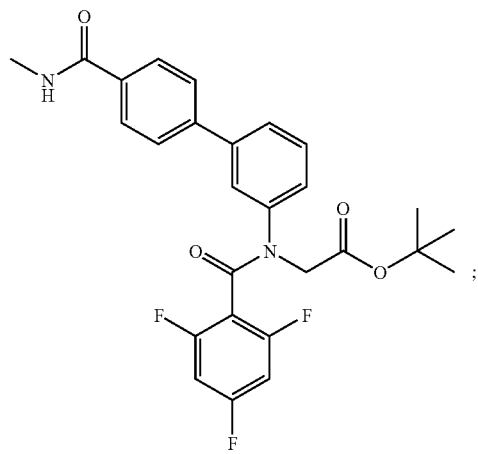
206
-continued
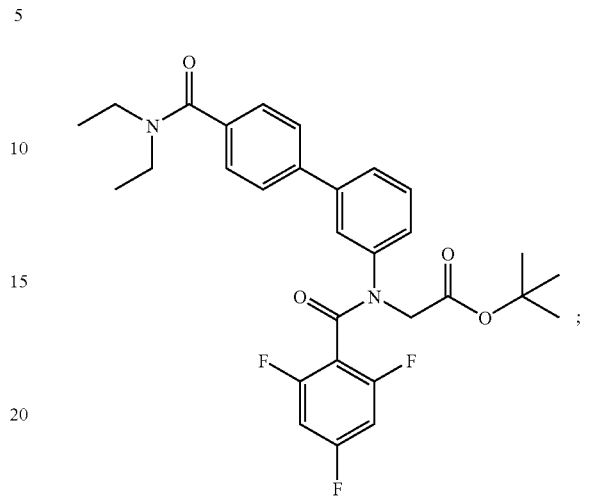
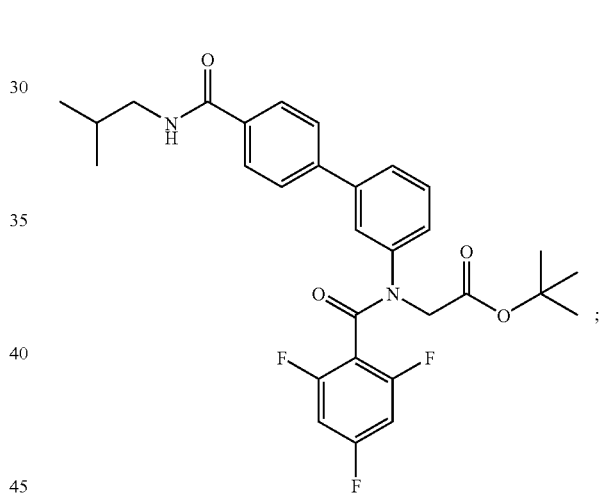
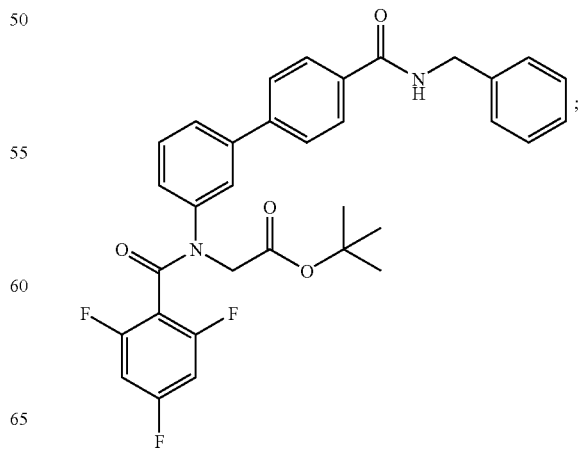

207
-continued
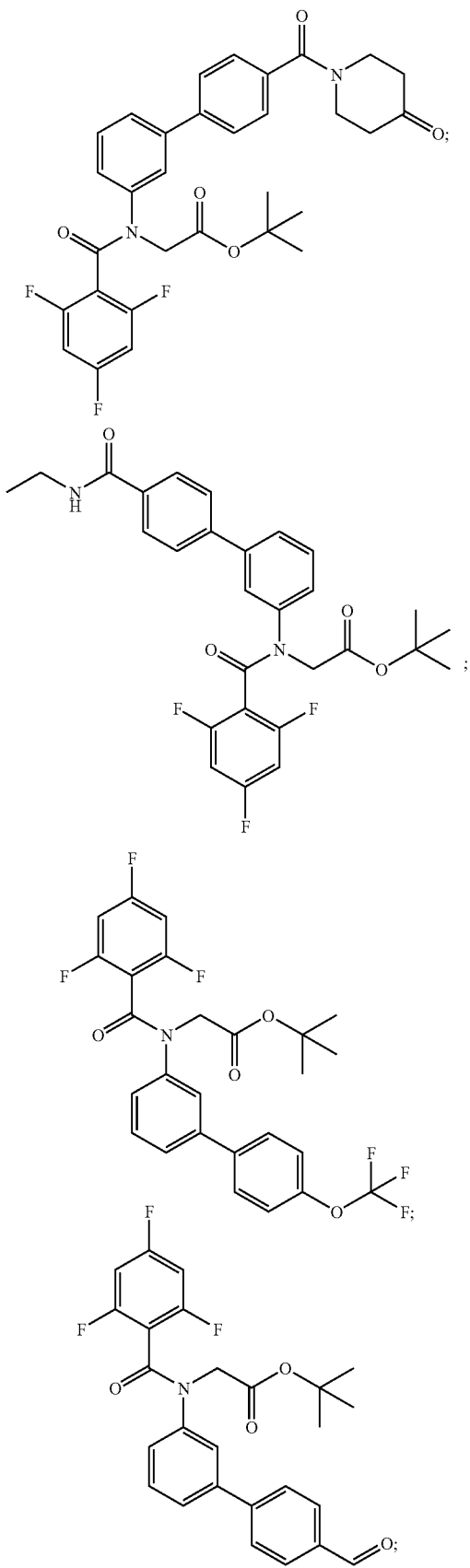
208
-continued
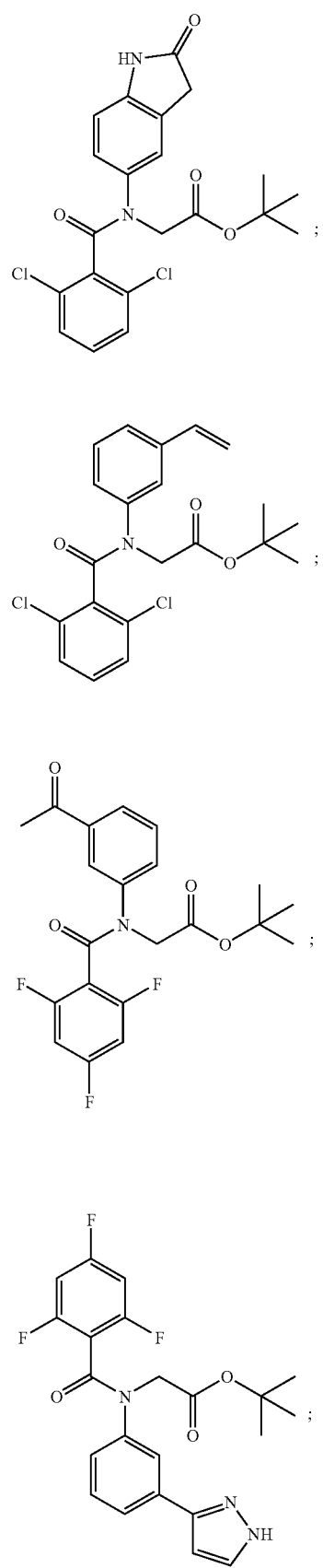

209
-continued
210
-continued
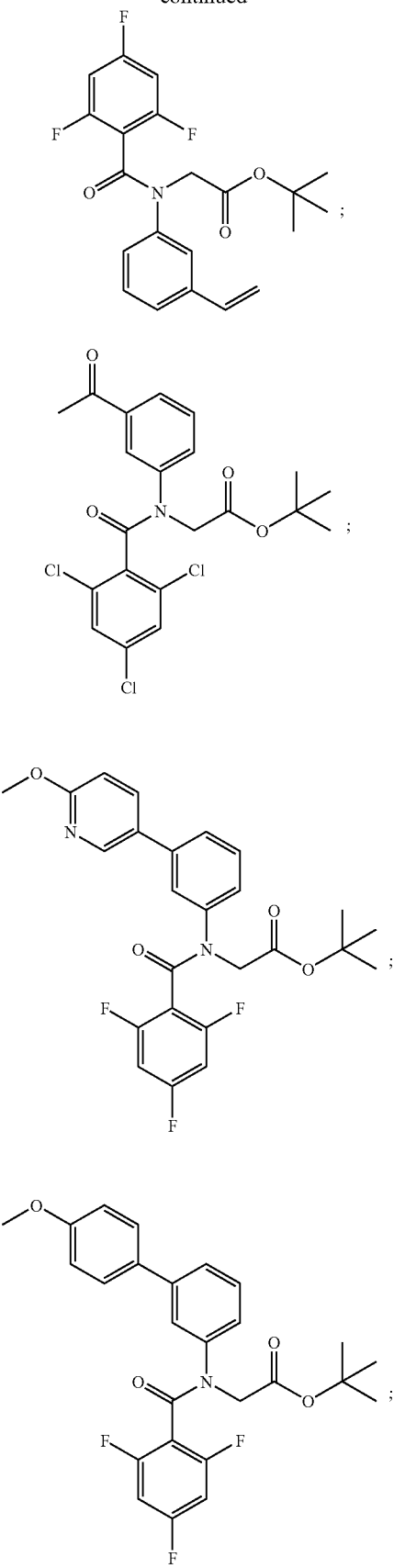
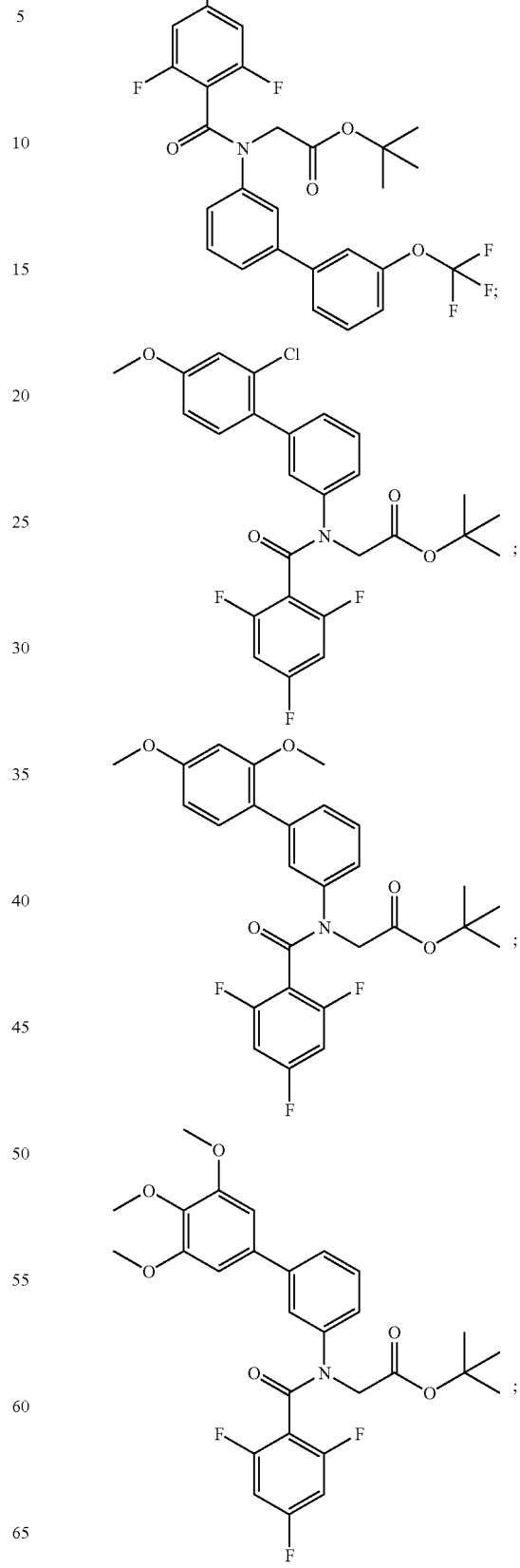

-continued
211
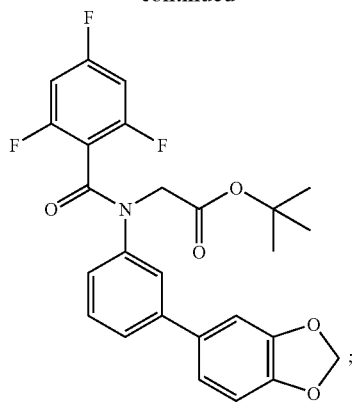
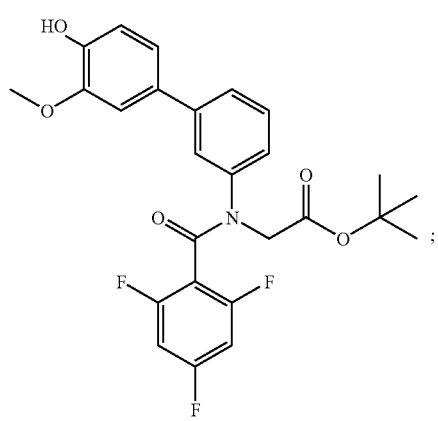
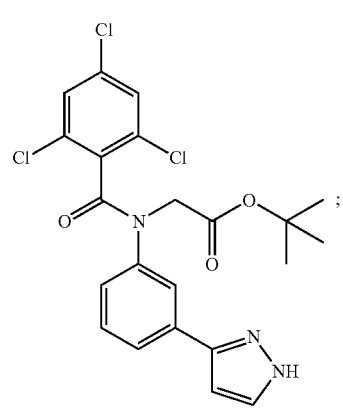
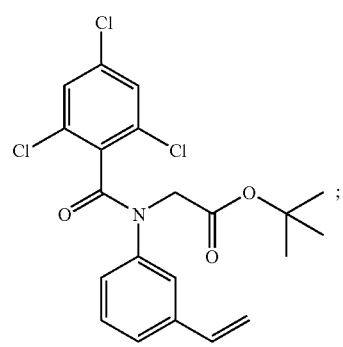
-continued
212
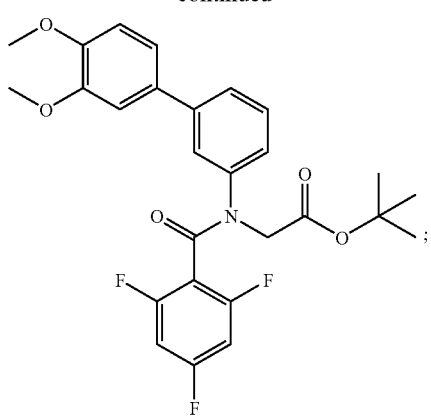
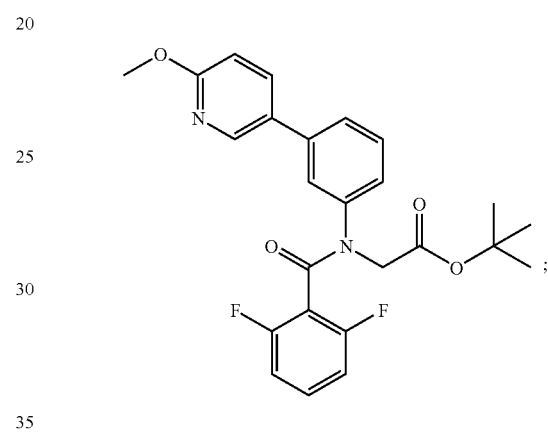
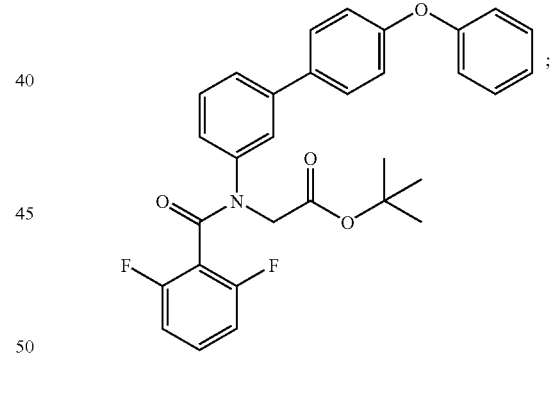
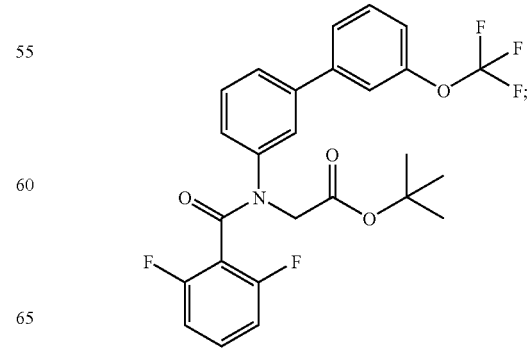

-continued

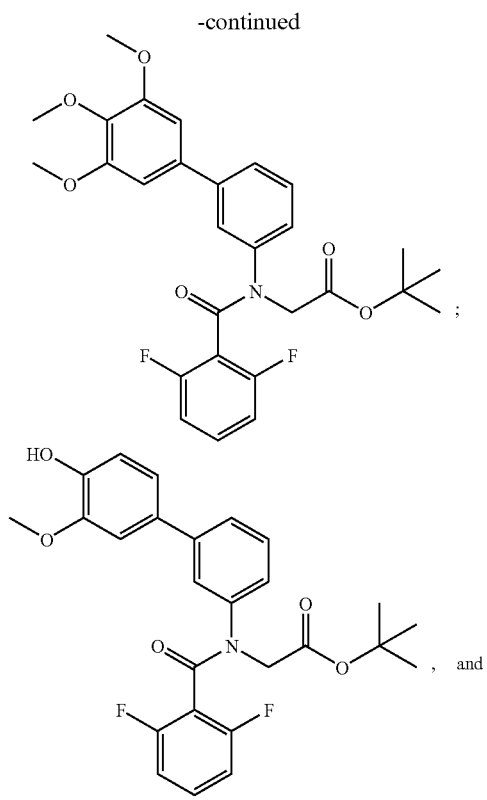

, and

-continued

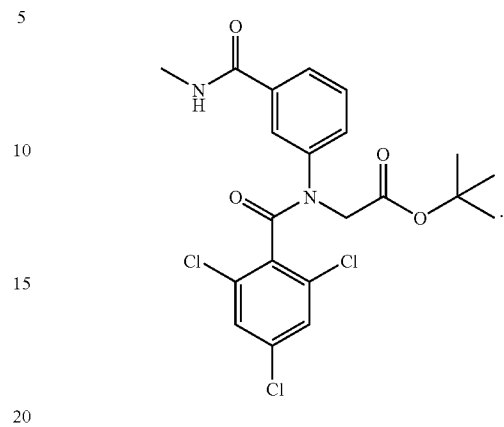

2. A pharmaceutical composition comprising a therapeutically effective amount of a compound of claim 1, or pharmaceutically acceptable salt thereof, in combination with a pharmaceutically acceptable excipient.

3. A method for modulation of LXR activity, which method comprises administering to an animal an effective amount of a compound of claim 1.

* * * * *